US010117755B2

(12) United States Patent
Emerick et al.

(10) Patent No.: US 10,117,755 B2
(45) Date of Patent: Nov. 6, 2018

(54) MULTIPLE SPINDLE ADJUSTABLE INTERBODY FUSION DEVICES AND METHODS OF USE

(71) Applicant: BIOSPINE, LLC, Columbia City, IN (US)

(72) Inventors: Brian G. Emerick, Columbia City, IN (US); Ross R. Nichols, North Webster, IN (US); Daniel D. Refai, Atlanta, GA (US); Heidi Stamets, Monroeville, IN (US); Larry D. Sutton, Columbia City, IN (US); Brent Walter, Huntington, IN (US)

(73) Assignee: BioSpine, LLC, Columbia City, IN (US)

( * ) Notice: Subject to any disclaimer, the term of this patent is extended or adjusted under 35 U.S.C. 154(b) by 643 days.

(21) Appl. No.: 14/394,700

(22) PCT Filed: Mar. 15, 2013

(86) PCT No.: PCT/US2013/032166
§ 371 (c)(1),
(2) Date: Oct. 15, 2014

(87) PCT Pub. No.: WO2013/158294
PCT Pub. Date: Oct. 24, 2013

(65) Prior Publication Data
US 2015/0094814 A1    Apr. 2, 2015

Related U.S. Application Data

(60) Provisional application No. 61/756,171, filed on Jan. 24, 2013, provisional application No. 61/730,347, (Continued)

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/442* (2013.01); *A61F 2/447* (2013.01); *A61F 2/4465* (2013.01);
(Continued)

(58) Field of Classification Search
CPC ............ A61F 2/442; A61F 2002/30579; A61F 2002/30616; A61F 2002/30843;
(Continued)

(56) References Cited

U.S. PATENT DOCUMENTS 6,562,074 B2 * 5/2003 Gerbec ................. A61F 2/4455
                                                623/17.15
7,708,779 B2 * 5/2010 Edie .......................... A61F 2/44
                                                623/17.11
(Continued)

FOREIGN PATENT DOCUMENTS

EP         2838452 A1    2/2015

OTHER PUBLICATIONS

International Search Report and Written Opinion for PCT/US2013/032166, dated Jul. 10, 2013; ISA/KR.
(Continued)

*Primary Examiner* — Zade Coley
*Assistant Examiner* — Jessica Weiss
(74) *Attorney, Agent, or Firm* — Heslin Rothenberg Farley & Mesiti P.C.

(57) ABSTRACT

An interbody fusion device includes a base member, a top member, and an expansion mechanism for moving the top member relative to the base member. The expansion mechanism may include a connector drive rod assembly, a gear, a threaded rod, and a support means. The gear ring is coupled to the threaded rod and is rotatable. The expansion mechanism may also include at least one load head coupled to the threaded rod. An alternative interbody fusion device is also
(Continued)

disclosed and includes a bottom member, a superior member, and an expansion mechanism for moving the superior member relative to the bottom member. The expansion mechanism includes a first expansion assembly for moving a first end of the superior member relative to the bottom member, a second expansion assembly for moving a second end of the superior member relative to the bottom member, and a connector drive rod assembly.

21 Claims, 32 Drawing Sheets

Related U.S. Application Data filed on Nov. 27, 2012, provisional application No. 61/652,606, filed on May 29, 2012, provisional application No. 61/624,814, filed on Apr. 16, 2012.

(51) Int. Cl.
*A61F 2/30* (2006.01)
*A61F 2/28* (2006.01)

(52) U.S. Cl.
CPC ..... *A61F 2/4611* (2013.01); *A61F 2002/2835* (2013.01); *A61F 2002/304* (2013.01); *A61F 2002/3052* (2013.01); *A61F 2002/3055* (2013.01); *A61F 2002/3084* (2013.01); *A61F 2002/3093* (2013.01); *A61F 2002/30331* (2013.01); *A61F 2002/30365* (2013.01); *A61F 2002/30383* (2013.01); *A61F 2002/30398* (2013.01); *A61F 2002/30401* (2013.01); *A61F 2002/30405* (2013.01); *A61F 2002/30444* (2013.01); *A61F 2002/30471* (2013.01); *A61F 2002/30504* (2013.01); *A61F 2002/30523* (2013.01); *A61F 2002/30525* (2013.01); *A61F 2002/30538* (2013.01); *A61F 2002/30556* (2013.01); *A61F 2002/30579* (2013.01); *A61F 2002/30594* (2013.01); *A61F 2002/30596* (2013.01); *A61F 2002/30598* (2013.01); *A61F 2002/30601* (2013.01); *A61F 2002/30604* (2013.01); *A61F 2002/30607* (2013.01); *A61F 2002/30616* (2013.01); *A61F 2002/30626* (2013.01); *A61F 2002/30632* (2013.01); *A61F 2002/30785* (2013.01); *A61F 2002/30904* (2013.01); *A61F 2002/4475* (2013.01); *A61F 2310/00017* (2013.01); *A61F 2310/00023* (2013.01); *A61F 2310/00359* (2013.01)

(58) Field of Classification Search
CPC .... A61F 2002/4475; A61F 2002/30411; A61F 2002/30484
USPC .......................................... 623/17.11–17.16
See application file for complete search history.

(56) References Cited

U.S. PATENT DOCUMENTS

| | | | |
|---|---|---|---|
| 2003/0130739 A1* | 7/2003 | Gerbec | A61F 2/4455 623/17.15 |
| 2004/0167626 A1* | 8/2004 | Geremakis | A61F 2/4425 623/17.15 |
| 2006/0100710 A1 | 5/2006 | Gutlin et al. | |
| 2006/0235389 A1* | 10/2006 | Albert | A61B 17/7032 128/898 |
| 2006/0293755 A1* | 12/2006 | Lindner | A61F 2/442 623/17.15 |
| 2007/0191954 A1 | 8/2007 | Hansell et al. | |
| 2010/0057204 A1* | 3/2010 | Kadaba | A61F 2/44 623/17.12 |
| 2010/0179655 A1* | 7/2010 | Hansell | A61F 2/44 623/17.11 |
| 2011/0130835 A1 | 6/2011 | Ashley et al. | |
| 2011/0160861 A1 | 6/2011 | Jimenez et al. | |
| 2011/0172716 A1 | 7/2011 | Glerum | |
| 2011/0251692 A1 | 10/2011 | McLaughlin et al. | |
| 2011/0257751 A1 | 10/2011 | Sherman et al. | |
| 2011/0282453 A1* | 11/2011 | Greenhalgh | A61B 17/8858 623/17.16 |
| 2012/0310350 A1* | 12/2012 | Farris | A61F 2/4425 623/17.16 |
| 2014/0288652 A1* | 9/2014 | Boehm | A61F 2/4465 623/17.15 |
| 2015/0025634 A1* | 1/2015 | Boehm | A61F 2/4425 623/17.15 |

OTHER PUBLICATIONS

"European Application Serial No. 13777545.8, Extended European Search Report dated Nov. 2, 2015", 6 pgs.
"European Application Serial No. 13777545.8, Response filed May 27, 2016 to Extended European Search Report dated Nov. 2, 2015", 8 pgs.
"International Application Serial No. PCT/US2013/032166, International Preliminary Report on Patentability dated Oct. 30, 2014", 12 pgs.

* cited by examiner

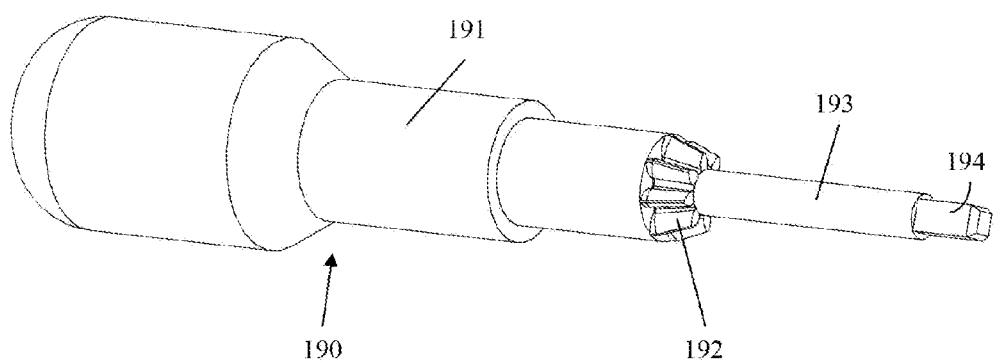
FIG. 11
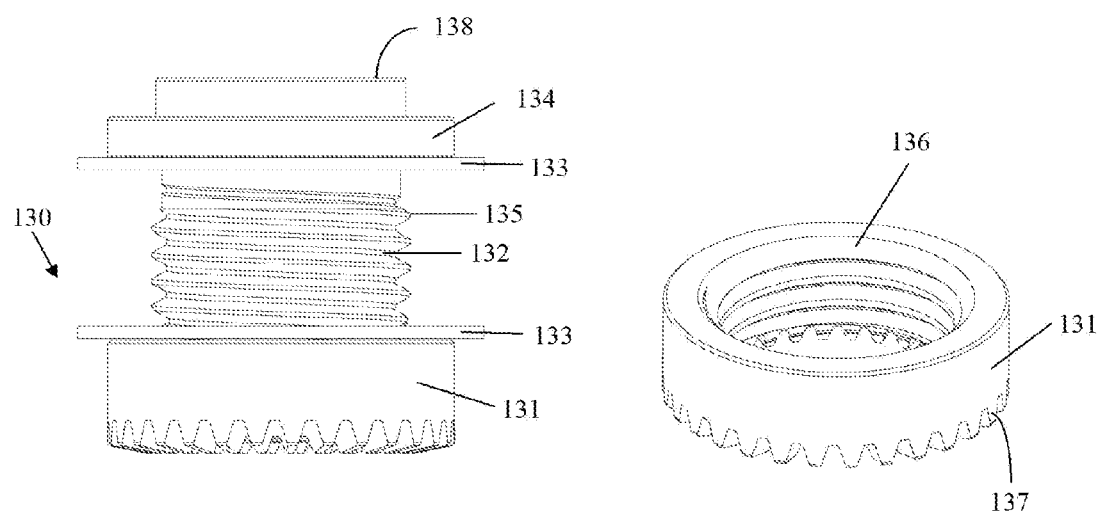
FIG. 12
FIG. 13

MULTIPLE SPINDLE ADJUSTABLE INTERBODY FUSION DEVICES AND METHODS OF USE

CROSS-REFERENCE TO RELATED APPLICATIONS

This application is a 371 U.S. National Stage of International Application No. PCT/US2013/032166, filed Mar. 15, 2013, which claims priority benefit under 35 U.S.C. § 119(e) of U.S. provisional application Nos. 61/624,814 filed Apr. 16, 2012, 61/652,606 filed May 29, 2012, 61/730,347 filed Nov. 27, 2012, and 61/756,171 filed Jan. 24, 2013. The entire disclosures of the above applications are incorporated by reference herein.

TECHNICAL FIELD

The present invention relates generally to general surgery, orthopaedic and neurosurgical implants used for insertion within a space between hard tissue structures, and more specifically, but not exclusively, concerns devices implanted between bones to replace resected, fractured or diseased structures and to maintain or reestablish proper spacing between two bones.

BACKGROUND OF THE INVENTION

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY OF THE INVENTION

Advancement of the state of interbody fusion implants and the surgical management relating to the clinical presentation of damaged tissue structures within the body is believed desirable. Several examples of embodiments of the invention used to treat patients suffering from either diseased or damaged disc or other tissue structures include at least one moveable member coupled to a base member with a modular tool for actuating the moveable member.

The present invention provides in one aspect, an interbody fusion device having a base member, a top member and an expansion mechanism for moving the top member relative to the base member.

The present invention provides in another aspect, an interbody fusion device with a bottom member, a superior member, an expansion mechanism for moving the superior member relative to the bottom member. The expansion mechanism including at least one expansion assembly for moving an end of the superior member relative to the bottom member.

The present invention provides in another aspect, a surgical method for maintaining a space between two vertebral bodies in a spine, the method may include the step of obtaining a medical device having a base member, a top member, and an expansion mechanism for moving the top member relative to the base member. The method may include the step of inserting and coupling an expansion tool into an opening within the medical device and also slidingly inserting the medical device into a space between two vertebral bodies. The method may include the further step of rotating the expansion tool to move the top member in a direction either away from or towards the base member, respectively.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 11 is a perspective view of the expansion tool, in accordance with an aspect of the present invention;

FIG. 12 is a side view of one expansion assembly, in accordance with an aspect of the present invention;

FIG. 13 is a superior perspective view of the gear ring of the expansion assembly, in accordance with an aspect of the present invention;

DETAILED DESCRIPTION FOR CARRYING OUT THE INVENTION

Generally stated, disclosed herein are various embodiments of an interbody fusion implant or interbody device that typically includes a top member, a base member, at least one expansion mechanism or assembly that may comprise a connector drive rod or connector drive rod assembly, a threaded rod member or a threaded rod, at least one gear ring member, cylindrical gear member, or spiral gear member, and a support means. Further, the interbody device may include an extendable/retractable member and an expansion tool. The extendable/retractable member extends typically in a vertical direction, although it may also expand horizontally. As used herein, the terms "interbody fusion device", "device", "interbody device," "TLIF device" and "implant" may be used interchangeable as they essentially describe the same type of device. Further, the corresponding expansion tool used for expansion and contraction of the interbody device may be referred to as "tool" or "instrument." Finally, described herein is a surgical method for using the interbody fusion device to maintain a space between two vertebral bodies within a patient suffering from a diseased or damaged disc or spinal column.

Figure 1:
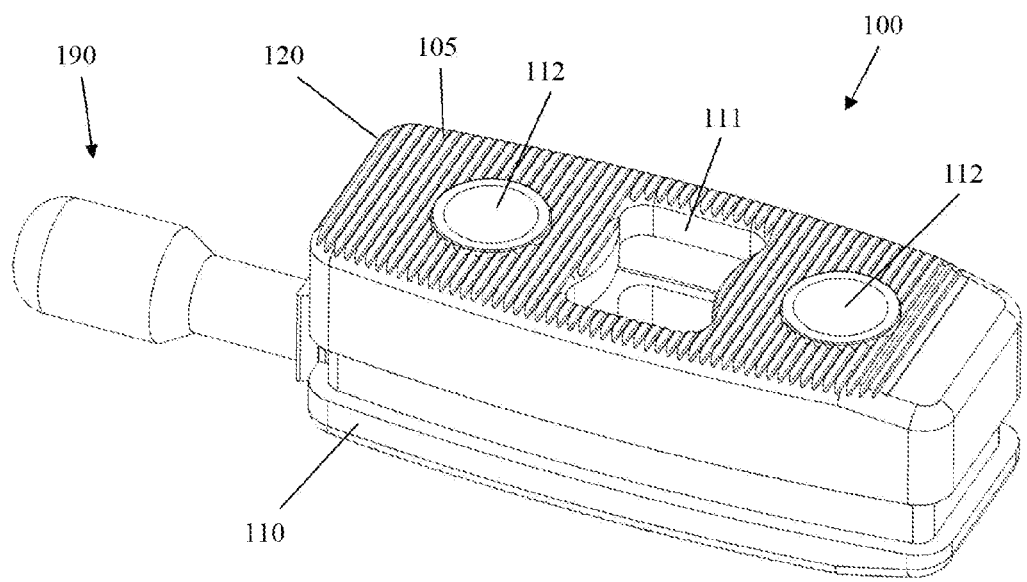
FIG. 1 is a perspective view of one embodiment of a unilateral, vertical expandable interbody fusion device, in accordance with an aspect of the present invention.
Figure 14:
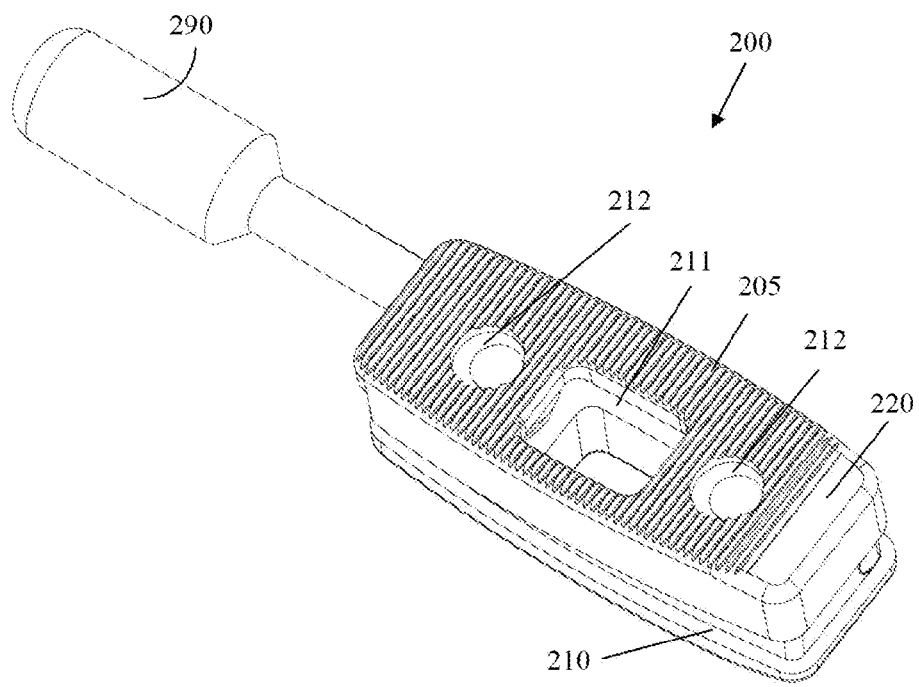
FIG. 14 is a perspective view of an alternative embodiment of a unilateral, vertical expandable interbody fusion device, in accordance with an aspect of the present invention.
Figure 26:
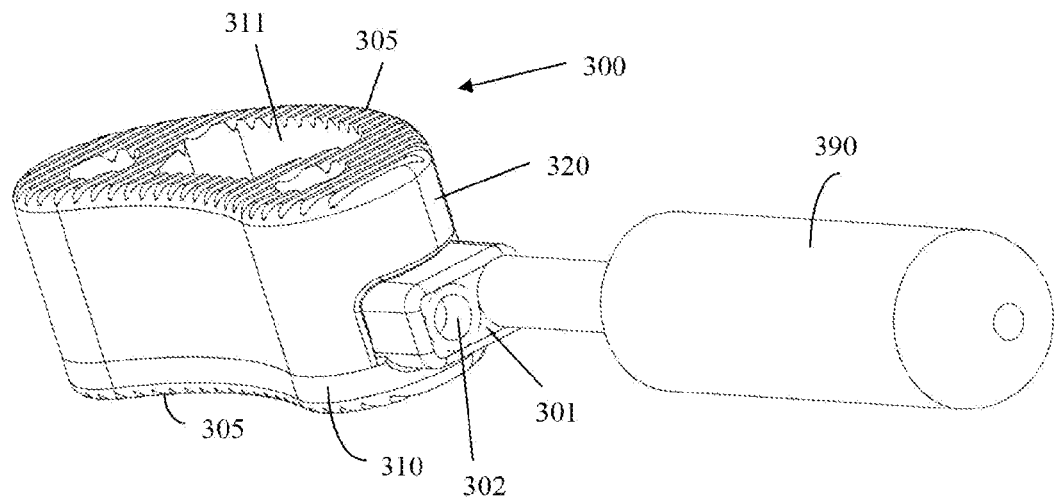
FIG. 26 is a perspective view of a further alternative embodiment of a unilateral, vertical expandable interbody fusion device, in accordance with an aspect of the present invention.
Figure 38:
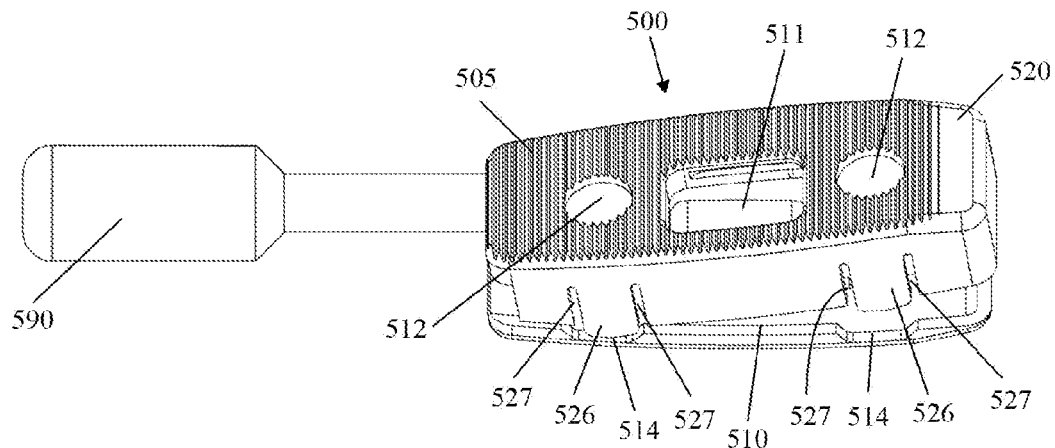
FIG. 38 is an anterior perspective view of a further embodiment of a unilateral, vertical expandable interbody fusion device with one superior end in an extended position and a second superior end in a retracted position, in accordance with an aspect of the present invention.
Figure 48:
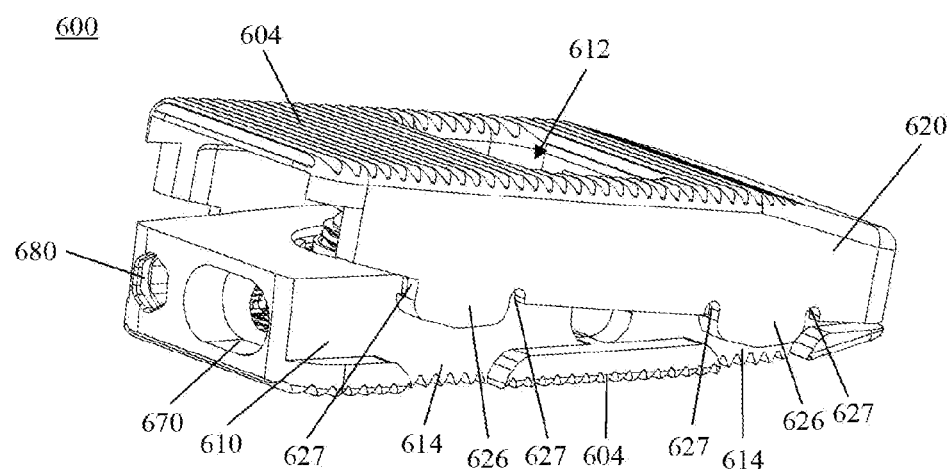
FIG. 48 is a lateral perspective view of yet another embodiment of a unilateral, vertical expandable interbody fusion device with one superior end in an extended position and a second superior end in a retracted position, in accordance with an aspect of the present invention.
Figure 57:
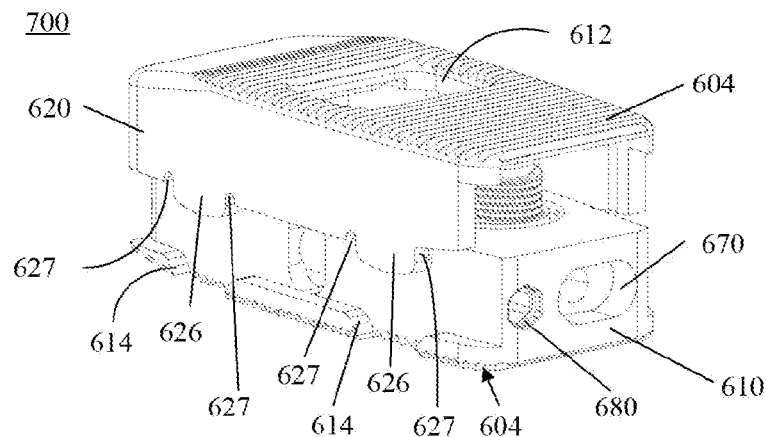
FIG. 57 is a lateral perspective view of another embodiment of a unilateral, vertical expandable interbody fusion device with the top member in a fully extended position, in accordance with an aspect of the present invention.
Figure 61:
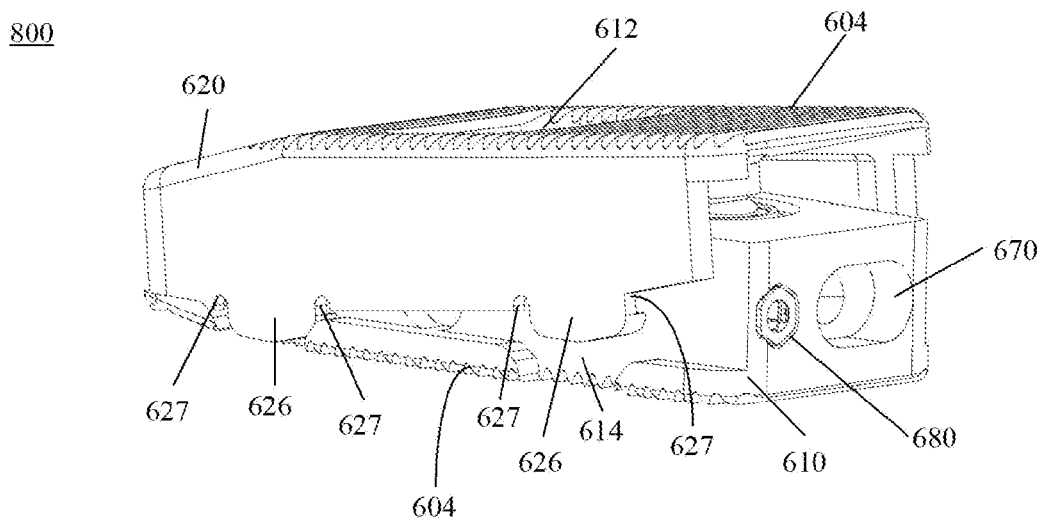
FIG. 61 is a lateral perspective view of yet another embodiment of a unilateral, vertical expandable interbody fusion device with one superior end in an extended position and a second superior end in a retracted position, in accordance with an aspect of the present invention.
Figure 68:
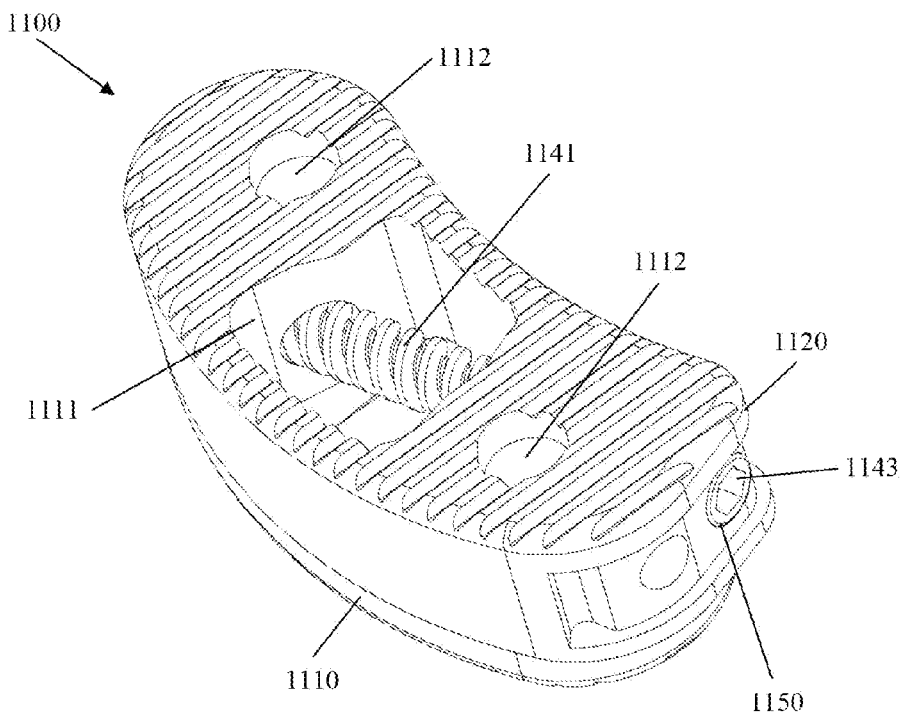
FIG. 68 is a superior perspective view of one embodiment of a unilateral, vertical expandable interbody fusion device, in accordance with an aspect of the present invention.

As depicted in FIG. 1, the general arrangement of a unilateral vertical expandable interbody fusion device 100, in accordance with an aspect of the present invention, includes a base member 110 and a top member 120. Also shown in FIG. 14, is the general arrangement of another embodiment of a unilateral vertical expandable interbody fusion device 200, in accordance with an aspect of the present invention that, includes a base member 210 and a superior member 220. Further shown in FIG. 26, is the general arrangement of yet another embodiment of a unilateral vertical expandable interbody fusion device 300, in accordance with an aspect of the present invention that, includes a base member 310 and a superior member 320. As depicted in FIG. 38, the general arrangement of yet another embodiment of a unilateral, vertical expandable interbody fusion device 500, in accordance with an aspect of the present invention, includes a base member 510 and a top member 520. Also depicted in FIG. 48, is the general arrangement of another embodiment of a unilateral, vertical expandable interbody fusion device 600, in accordance with an aspect of the present invention, includes a base member 610 and a top member 620. Further shown in FIG. 57, is the general arrangement of an embodiment of a unilateral, vertical expandable interbody fusion device 700, in accordance with an aspect of the present invention, includes a base member 610 and a top member 620. As shown in FIG. 61, is the general arrangement of another embodiment of a unilateral, vertical expandable interbody fusion device 800, in accordance with an aspect of the present invention, includes a base member 810 and a top member 820. Also depicted in FIG. 68, is the general arrangement of an embodiment of a unilateral, vertical expandable interbody fusion device 1100, in accordance with an aspect of the present invention, includes a base member 1110 and a top member 1120.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

It is shown in FIG. 1, the example of the unilateral, vertical expandable interbody fusion device 100. The device 100 as seen in FIGS. 1-4, has a generally rectangular geometry with various configured long sides to facilitate insertion and bone coverage. Although it would be understood by one skilled in the art that other outside configurations can be used. For example purposes, the long sides are slightly arcuate although it is contemplated that other geometrical shapes may also be used in the construct. The implant 100 may likely include at least one moveable top member 120 and a base member 110. The top member 120 may be detachably coupled to the base member 110.

Figure 3:
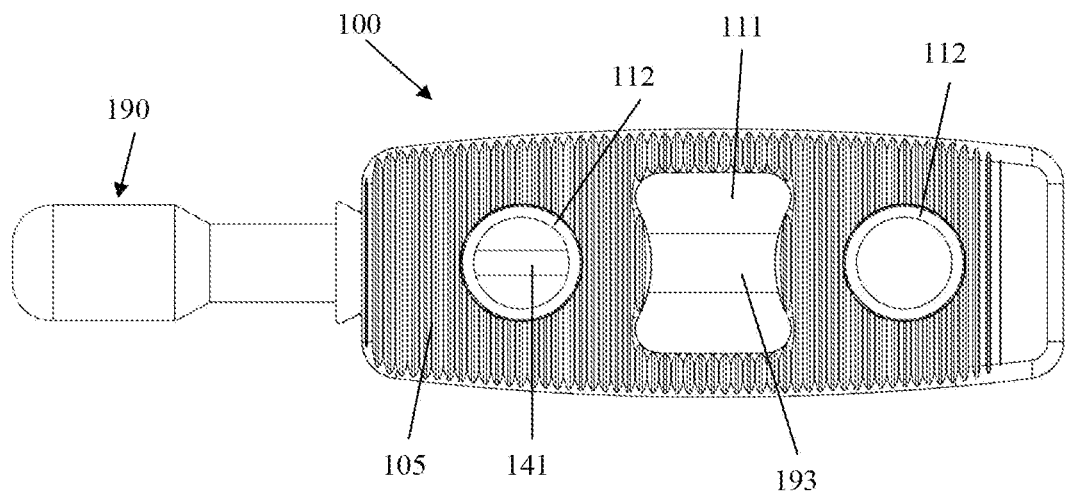
FIG. 3 is a superior view of the expandable interbody fusion device of FIG. 1, in accordance with an aspect of the present invention.

As seen in FIGS. 1 and 3, at least one through hole 111 for insertion of bone graft material is disposed on the inferior and superior bone contacting surfaces 105. The hole 111 (three are shown in FIGS. 1 and 3) extends through the external surfaces 105 of the base member 110 and top member 120. The opening 111 typically extends through both bone contacting surfaces 105 and into the inner cavity of the device 100. The size and configuration of the opening 111 allows the surgeon to place bone graft material inside the implant 100 to achieve a continuous fusion between the inferior and superior vertebral bodies.

Figure 2:
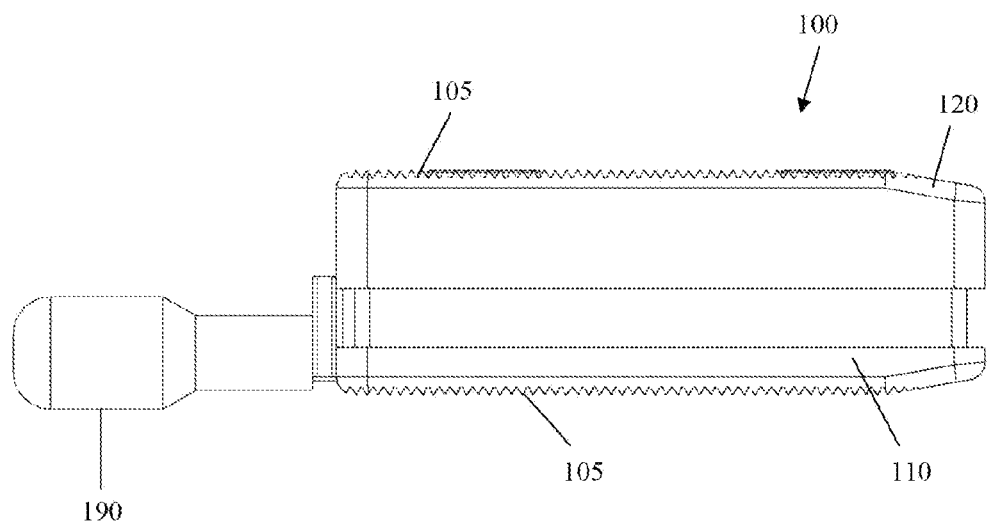
FIG. 2 is a side view of the expandable interbody fusion device of FIG. 1 with the moveable member partially extended, in accordance with an aspect of the present invention.

As shown in FIG. 2, the superior and inferior bone contacting surfaces 105 are generally parallel to each other. However, for the embodiment seen in FIGS. 14-16, the bone contacting surfaces 205 may be angled relative to each other. FIGS. 1, 2 and 3 exhibit the bone contacting surfaces 105 to have teeth-like or tine structures projecting away from the superior and inferior surfaces. One skilled in the art would recognize that other surface treatments may be applied to the bone contacting surfaces 105 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial/ ingrowth surfaces and ridge structures. Further, it is contemplated that angled bone contacting surfaces, caps or plates may be attachable to the implant 100 to address various clinical deformities that are encountered clinically. It is also understood that the bone contacting surfaces 105 may be coated with bioactive or bone ingrowth coatings.

Figure 4:
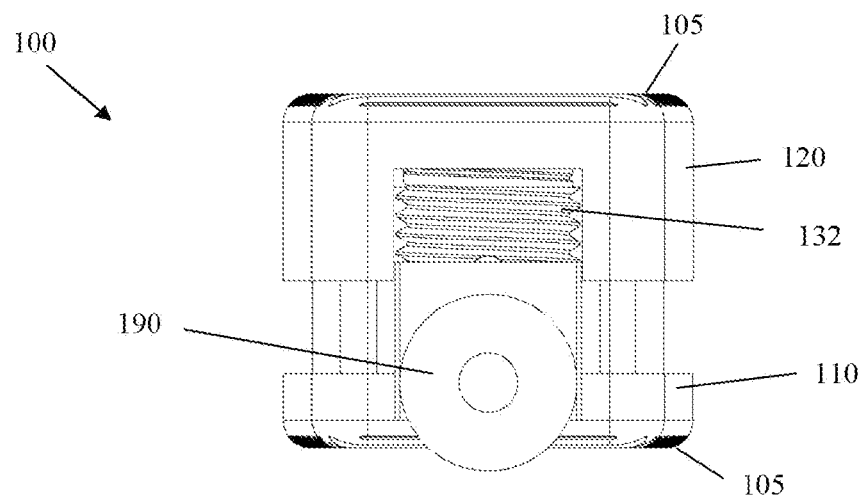
FIG. 4 is a back view of the expandable interbody fusion device of FIG. 1 with the moveable member partially extended and the expansion tool inserted, in accordance with an aspect of the present invention.

FIG. 4 is a back view of the implant 100 showing the expansion tool 190 extending away from a centralized opening in the end wall. The tool 190 will be described in more detail below.

Figure 5:
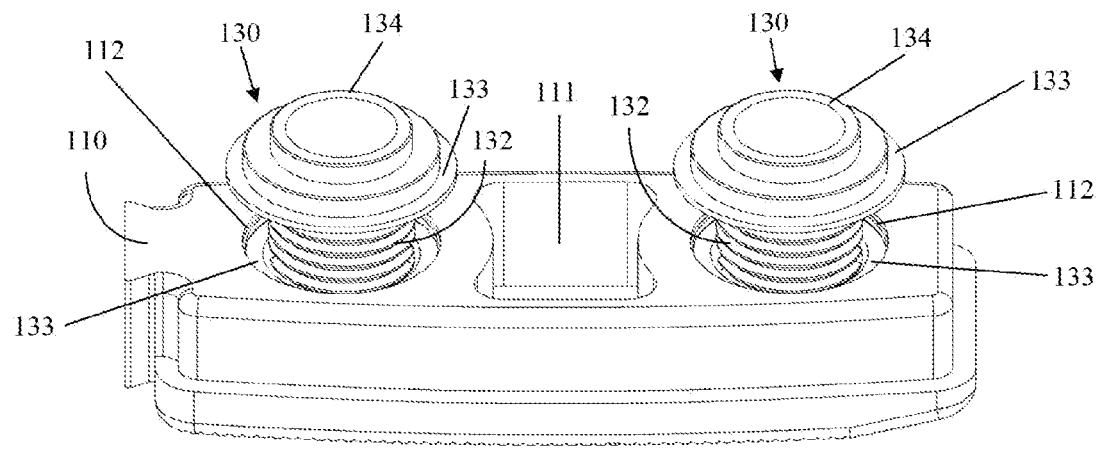
FIG. 5 is a superior perspective view of the expandable interbody fusion device of FIG. 1 showing only the base member with the seated dual expansion assemblies, in accordance with an aspect of the present invention.
Figure 6:
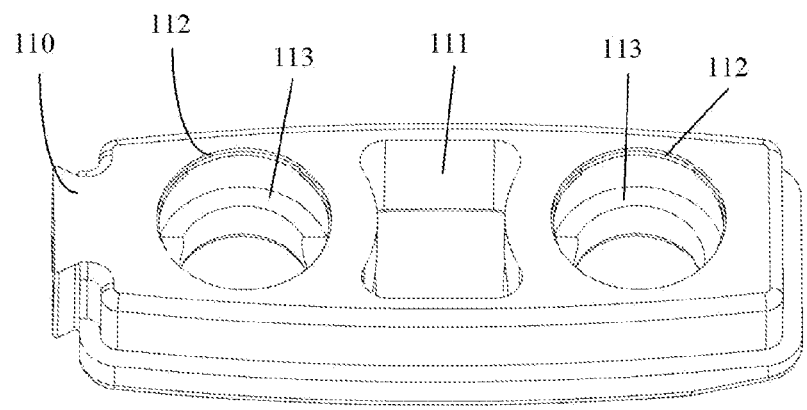
FIG. 6 is a superior perspective view of the expandable interbody fusion device of FIG. 1 showing only the base member, in accordance with an aspect of the present invention.

FIGS. 5 and 6, provide a superior view of the base member 110. FIG. 6 exhibits the central through hole 111 that allows the surgeon to insert bone graft material into the central portion of the assembled implant 100 following the implantation. Peripherally positioned holes 112 house a portion of the two expansion assemblies. More specifically, the support means 133, that is adjacent the gear ring 131, sits on a internal shoulder 113 and acts to maintain the expansion assembly 130 in a vertical orientation as well as function as a bearing surface for the support means 133. FIG. 5 shows the two expansion assemblies 130 nested within holes 112 and sitting on shoulder 113.

Figure 7:
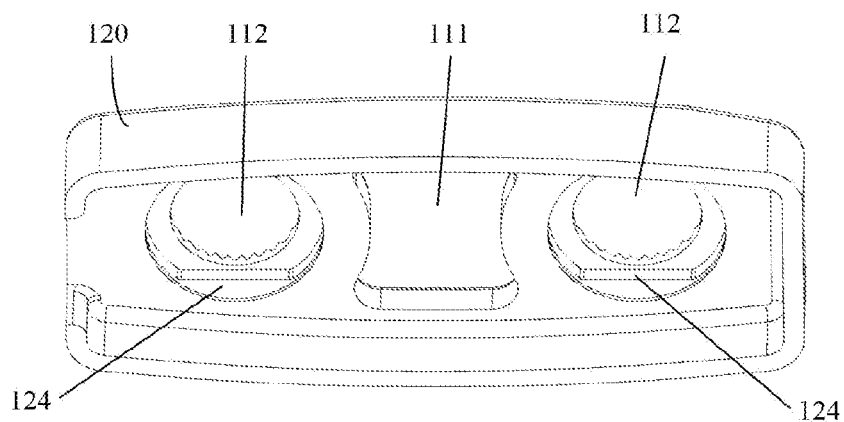
FIG. 7 is an inferior perspective view of the expandable interbody fusion device of FIG. 1 showing only the top or moveable member, in accordance with an aspect of the present invention.
Figure 8:
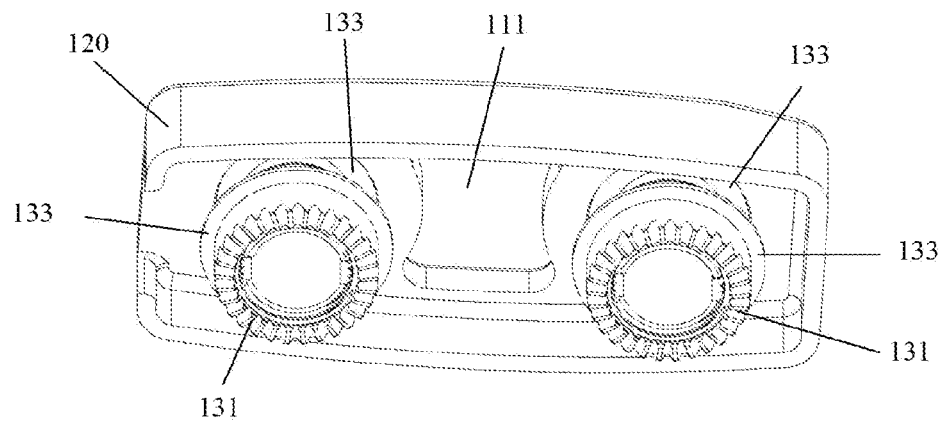
FIG. 8 is an inferior perspective view of the expandable interbody fusion device of FIG. 1 showing only the top or moveable member with the seated dual expansion assemblies, in accordance with an aspect of the present invention.

FIGS. 7 and 8 are inferior views of the top or superior moveable member 120. FIG. 7 shows the central opening 111 that is configured to allow the surgeon to insert bone graft material into the inner cavity of the implant 100. Peripheral holes 112 that mirror the peripheral holes in the base member 110 when the implant 100 is assembled are also shown. A ledge 124 is located within holes 112 and may act to retain the expansion assembly 130, restrict rotation of the threaded rod 132 and function as a load transfer surface when the expansion assembly is actuated. FIG. 8 shows two expansion assemblies 130 seated within holes 112 and resting and/or aligned with the ledge 124.

Figure 9:
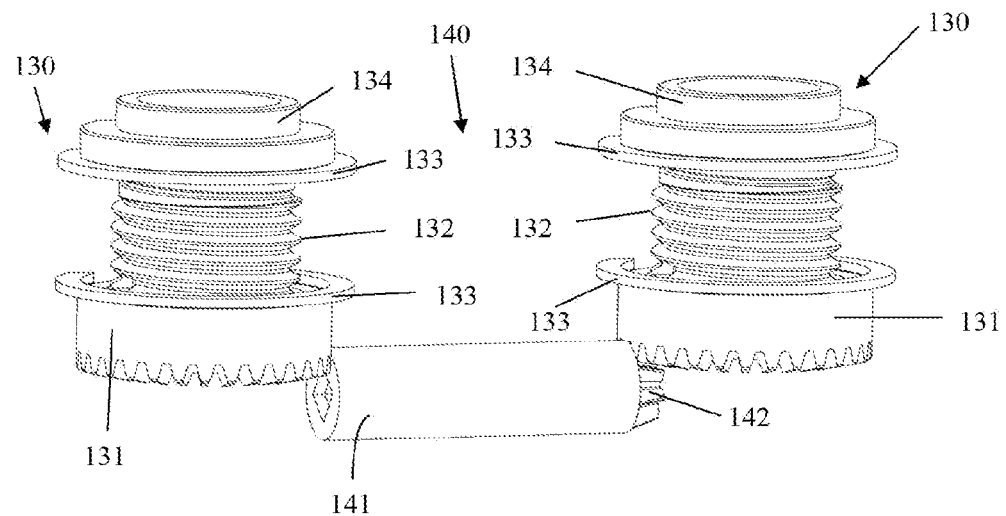
FIG. 9 is a side view of the expansion mechanism with the connecting drive rod, in accordance with an aspect of the present invention.

The expansion mechanism 140 is shown in FIG. 9 and comprises at least two expansion assemblies 130 and a connector drive rod 141 that spans the space between the two expansion assemblies 130. The spacing between the expansion assemblies 130 typically matches the distance between holes 112. The expansion mechanism 140 functions to convert rotational movement of the gear ring 131 into linear or translational movement of the load head 134 positioned at the top end of the threaded rod 132. The connector drive rod 141 functions to mirror the rotation movement between a first and second gear ring 131 and ultimately, the travel distance of the dual expansion assemblies 130 when the expansion mechanism 140 is actuated by an expansion tool, for example, the expansion tool 190. The connector drive rod 141 may be comprised of a cylindrical shaft with an opening at one end and a pinion gear 142 at the opposite end. The pinion gear 142 is configured to engage with the gear ring 131 of one of the expansion assemblies 130. When the implant 100 is assembled, the connector drive rod 141 is positioned adjacent to the floor of the base member 110 and extends through the mid-portion of hole 111 (see FIG. 3). The connector rod 141 is held in manner that will allow it to be freely rotated.

Figure 10:
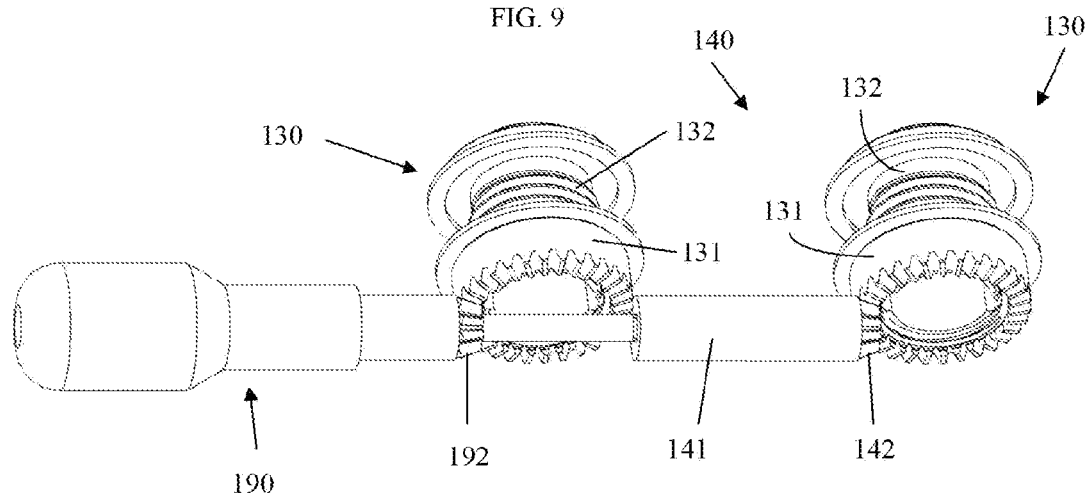
FIG. 10 is an inferior perspective view of the expansion mechanism with the connecting drive rod and the attached expansion tool, in accordance with an aspect of the present invention.

Seen in FIG. 10 is the expansion mechanism 140 that includes at least two expansion assemblies 130, a connector drive rod 141 that is positioned between the two expansion assemblies 130. Detachably coupled to one end of the connection rod 141 is an expansion tool, for example, expansion tool 190. The end of the expansion tool 190 may be configured as a hex head or other like configuration that will allow for the user to rotate the expansion tool 190 and cause the connector drive rod 141 to also rotate (see FIG. 11).

The expansion mechanism 140 is actuated by rotating the expansion tool 190. The tool 190 may be configured in various forms, depending upon the number of expansion assemblies 130 that are used in the expansion mechanism 140. For the expansion mechanism 140 example shown in FIG. 10, the tool 190 is shown in FIG. 11. The tool consists of a handle 191 with a gear 192 to interface with a near gear ring 131 of a first expansion assembly 130. Extending from a surface of the gear 192 is the shaft 193 that extends for the diameter of the first expansion assembly 130. Positioned at the end of shaft is a means for coupling 194 to the connector drive rod 141. For example, as seen in FIG. 11, this means is a square male end, although hex or other multi-lobed configurations may be used. In use, the means of coupling 194 is inserted into an opening or female end of the connector drive rod 141 to ensure that when the handle 191 is rotated, the gear 192, the connector drive rod 141 and pinion gear 142 will all rotate at the same speed thereby causing the two engaged gear rings 131 of the corresponding two expansion assemblies 130 to also rotate resulting in movement of the top member 120 in an upward or downward direction depending on the direction of rotation of the tool 190. The cogs or teeth of gear 142 on the connector rod 141 and the pinion gear 192 of the tool 190 are sized to mate with the corresponding cogs or teeth of the gear ring 131 to allow for free rotation of the gear ring 131 when engaged with the tool 190.

The constructed expansion assembly 130 and the various components that comprise it are seen in FIGS. 12 and 13. FIG. 12 shows the construct to include the gear ring 131, the threaded rod 132, the load head 134 and the support means 133. The threaded rod 132 and the load head 134 are shown in FIG. 12. The load head 134 is configured to maximize load transfer from the expansion assembly 130 to the undersurface of the top member 120. The top surface or top portion 138 of the load head 134 is generally planar to avoid point contact and high stress loads when it makes contact with the flat undersurface of the top member 120. The threaded rod 132 has external threads 135 extending along its length. The rod is typically hollow to allow for bone graft placement. The external threads 135 are configured to match the internal threads 136 of the gear ring 131 as seen in FIG. 13. Gear ring 131 is circular in shape and includes a gear face with a continuous circumferential sequence of cogs or teeth 137. These cogs or teeth 137 are configured to allow for mating with an expansion tool, for example, the expansion tool 190. The expansion assembly 130 acts to convert rotational movement of the gear ring 131 into translational movement of the threaded rod 132. This is achieved by allowing free rotational motion of the gear ring 131 while restricting the rotation of the threaded rod 132. By restricting the rotation of the threaded rod 132, the rod translates in either an upward or downward direction relative to the gear ring 131 depending upon whether the external/internal threads 135, 136 are oriented in a right-handed or left handed direction. As discussed above, when the threaded rod 132 moves, the load head 134 contacts the undersurface 121 of the top member 120 to either move it away from the base member 110 or towards the base member 110. In another words, the height of the implant 100 either increases or decreases depending upon the rotational direction of the tool 190.

As shown in FIG. 12, support means 133 are used both adjacent to the threaded rod 132 and the gear ring 131. The support means may be a snap ring or other similar type of structure that will secure the expansion assembly 130 within the openings 112 of the base member 110 and the top member 120. The support means 133 also facilitates retaining the assembly 130 in a position adjacent to either the shoulder 113 or the ledge 124.

Shown in FIG. 14, is another example of a unilateral, vertical expandable interbody fusion device 200. The device 200, as seen in FIG. 14, has a generally rectangular geometry, similar to device 100 described above with reference to FIGS. 1-4 and for brevity sake will not be described again. The implant 200 may likely include at least one moveable superior member 220 and a base member 210. The superior member 220 may be detachably coupled to the base member 210.

As seen in FIG. 14, at least one through opening 211 for insertion of bone graft material is disposed on the inferior and superior bone contacting surfaces 205. The opening 211 (three are shown in FIG. 14) extends through the external surfaces 205 of the base member 210 and the superior member 220. The opening 211 typically extends through both bone contacting surfaces 205 and into the inner cavity of the assembled implant 200. The size and configuration of the opening 211 allows the surgeon to place bone graft material inside the implant 200 to achieve a continuous fusion between the inferior and superior vertebral bodies.

Figure 15:
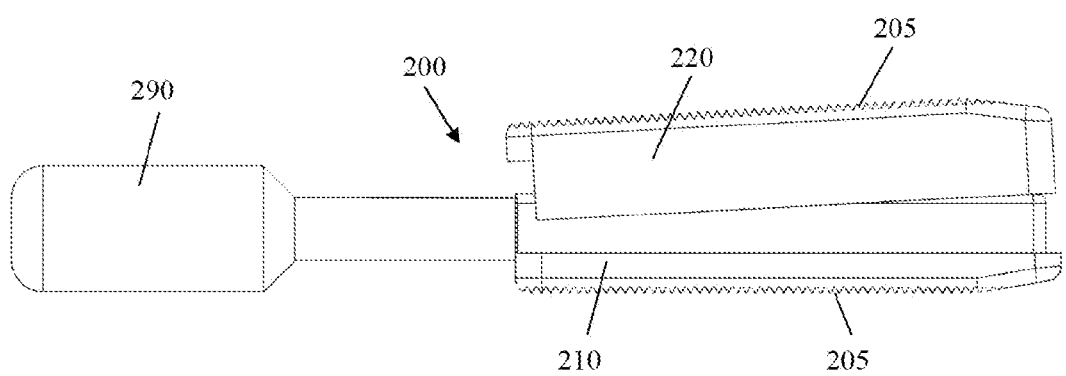
FIG. 15 is a side view of the expandable interbody fusion device of FIG. 14 with the moveable member partially extended, in accordance with an aspect of the present invention.
Figure 16:
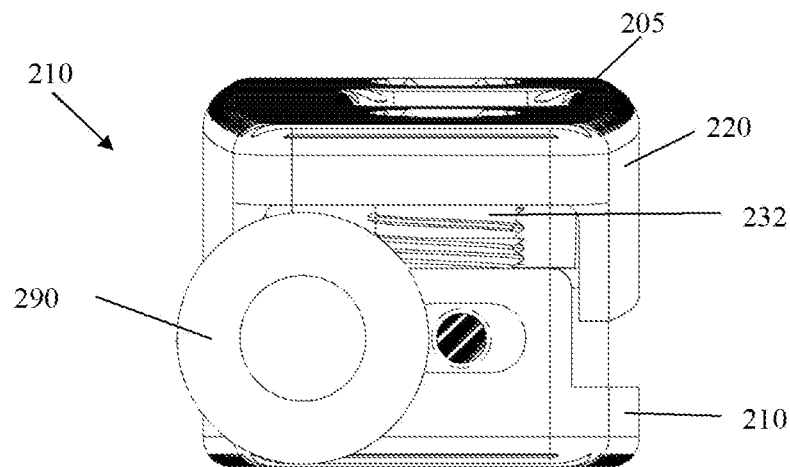
FIG. 16 is a back view of the expandable interbody fusion device of FIG. 14 with the moveable member partially extended and the expansion tool inserted, in accordance with an aspect of the present invention.

As shown in FIG. 15, the superior and inferior bone contacting surfaces 205 may be generally parallel to each other. However, the expansion mechanism 240 (see FIG. 22) will allow the user to angle the bone contacting surface 205 of the superior member 220 relative to the bone contacting surface 205 of the base member 210. FIGS. 14-16 show the bone contacting surfaces 205 to have teeth-like or tine structures projecting away from the superior and inferior surfaces. One skilled in the art would recognize that other surface treatments may be applied to the bone contacting surfaces 205 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. It is also understood that the bone contacting surfaces 205 may be coated with nano-surfacing, bioactive or bone ingrowth coatings.

FIG. 16 shows an expansion tool 290 being inserted off-center from the longitudinal axis of the implant 200. The off-center orientation is achieved by the configuration of the expansion mechanism 240 that will be described in more detail below. The off-center entry point of the tool 290 and the corresponding elimination of the expansion mechanism 240 through the center of the implant 200 provides the surgeon with the ability to pack a maximum amount of bone graft material through the opening 211 and create a continuous graft from the inferior vertebral body to the superior vertebral body. As seen in FIG. 14, the opening 211 is unobstructed by any tool or actuation shaft.

Figure 17:
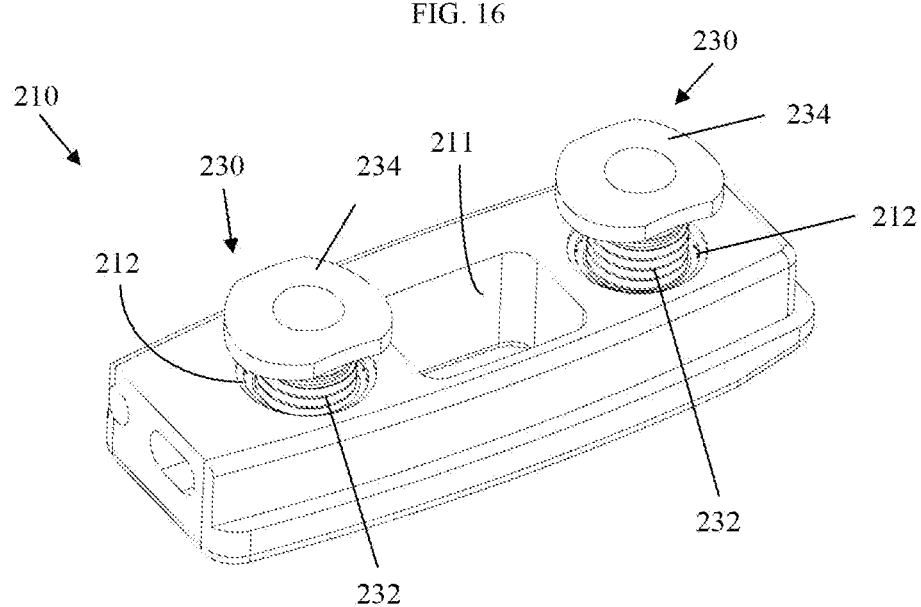
FIG. 17 is a superior perspective view of the expandable interbody fusion device of FIG. 14 showing only the base member with the seated dual expansion assemblies, in accordance with an aspect of the present invention.
Figure 18:
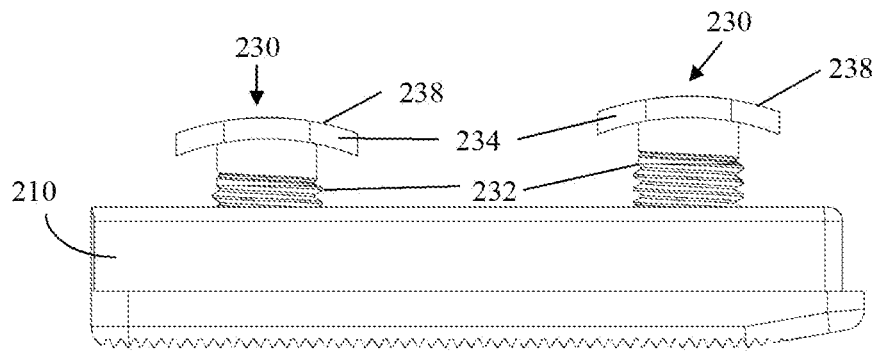
FIG. 18 is a side view of the expandable interbody fusion device of FIG. 14 showing only the base member with the seated dual expansion assemblies, in accordance with an aspect of the present invention.
Figure 19:
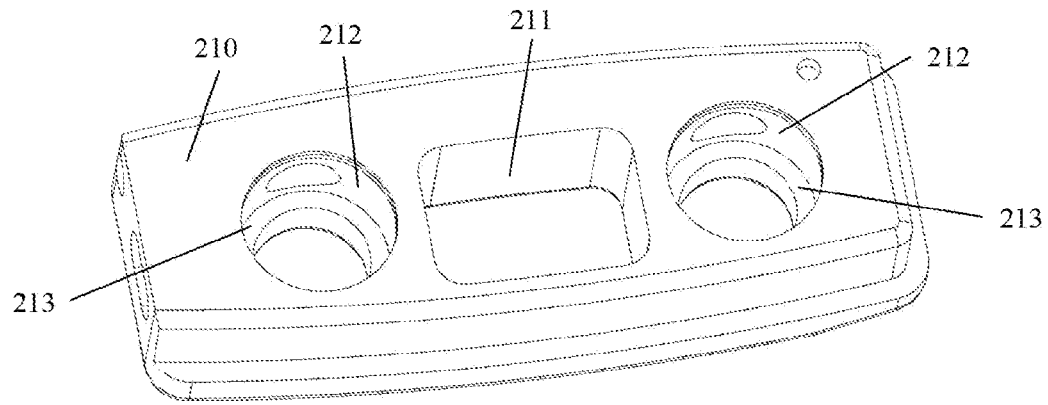
FIG. 19 is a superior perspective view of the expandable interbody fusion device of FIG. 14 showing only the base member, in accordance with an aspect of the present invention.

FIGS. 17 and 19, provide a superior view of the base member 210. FIG. 19 exhibits the central through hole 211 that allows the surgeon to insert bone graft material into the central cavity of the assembled implant 200 following the implantation. Peripherally positioned holes 212 are also seen and these are configured to house a portion of the at least two expansion assemblies 230. More specifically, the support means 233, that is adjacent the gear ring 231 may sit on the internal circumferential shoulder 213 that functions to maintain the expansion assembly 230 in a vertical orientation relative to the base member 210. The shoulder 213 also operates as a bearing surface against which the support means 233 contacts. FIGS. 17 and 18 show the two expansion assemblies 230 protruding above a planar inner surface of the base member 210 while positioned within holes 212 and seated on shoulder 213.

Figure 20:
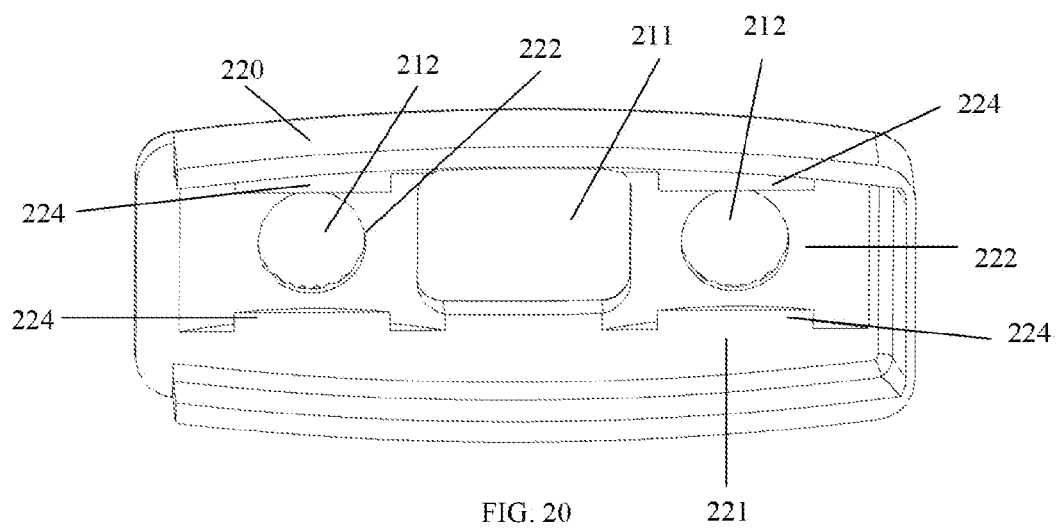
FIG. 20 is an inferior perspective view of the expandable interbody fusion device of FIG. 14 showing only the top or moveable member, in accordance with an aspect of the present invention.
Figure 21:
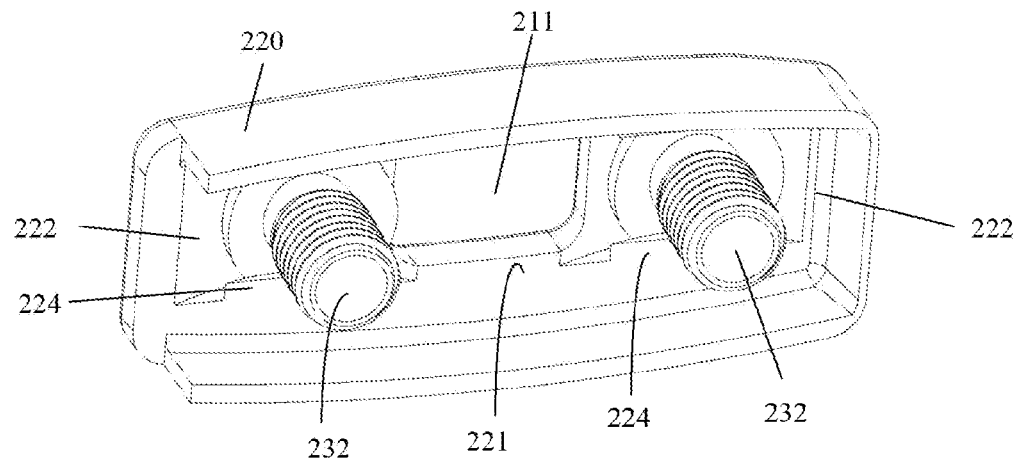
FIG. 21 is an inferior perspective view of the expandable interbody fusion device of FIG. 14 showing only the top or moveable member with the seated dual expansion assemblies, in accordance with an aspect of the present invention.

FIGS. 20 and 21 are inferior views of the undersurface 221 of the superior moveable member 220. FIG. 20 shows the central through hole 211 that is configured to permit the surgeon to insert bone graft material into the inner cavity of the implant 200 prior to implantation. Further viewed in these figures are peripheral holes 212 that align with the corresponding peripheral holes in the base member 210 when the implant 200 is assembled. Two opposing tabs 224 are located adjacent to the opposing sides of the holes 212 and may act to retain the load cap 234 of the expansion assembly 230 as well as restrict rotation of the threaded rod 232. FIG. 21 shows two load caps 234 engaged with the opposing tabs 224 for each hole 212. As seen in FIG. 20, the undersurface 221 in the area surrounding the holes 212 is concave 222 with the arc of curvature for each of these concavities running along the long axis of the implant 200. Each hole 212 has a separate surrounding concavity area 222 that will match a corresponding convexity on the top surface or top portion of the load cap 238. The concave undersurface 222 and the convex top surface 238 of the load cap allows the user to angle or tilt the superior member 220 relative to the base member 210 by extending the at least two expansion assemblies 230 to different lengths.

Figure 22:
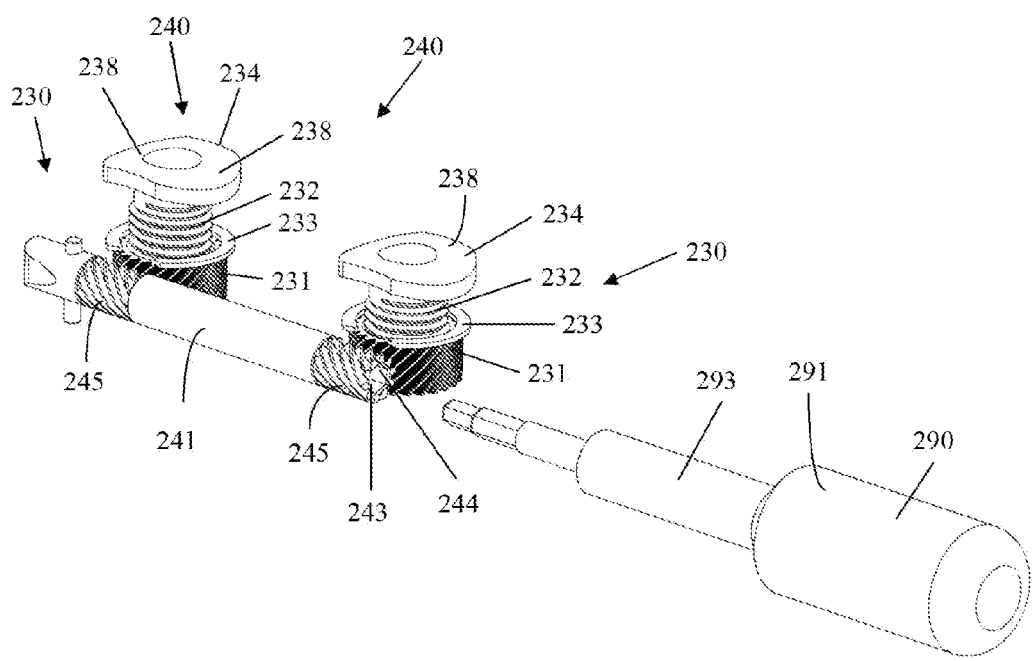
FIG. 22 is a side perspective view of the expansion mechanism with an expansion tool being inserted into the drive connector, in accordance with an aspect of the present invention.

An alternative expansion mechanism 240 is shown in FIG. 22 and comprises at least two expansion assemblies 230 and a connector drive rod 241 that spans the gap between the two expansion assemblies 230. The spacing between the expansion assemblies 230 typically matches the distance between the peripheral holes 212. As explained more below, the expansion assembly 230 is comprised of a spiral gear 231, a threaded rod 232, a load cap 234 and multiple support means 233. The expansion mechanism 240 functions to convert rotation movement of the spiral gear 231 into linear or translational movement of the load cap 234 positioned at the superior end of the threaded rod 232. The connector drive rod 241 with the two worm gears 245 functions to mirror the rotation movement of the tool 290 and translate this to either the first or second spiral gears 231, or alternatively, both at the same time. Rotation of the spiral gears 231 will result in a travel distance of the threaded rods 232 when the expansion mechanism 240 is actuated by the expansion tool 290.

The connector drive rod 241 may be comprised of a hollow cylindrical shaft 244 with an opening at one end 243, and two worm gears 245 positioned at either end of the connector drive rod 241. The worm gears 245 are configured to engage with the two spiral gears 231 of the expansion assemblies 230. When the implant 200 is assembled, the connector drive rod 241 is positioned adjacent to the floor of the base member 210 and eccentrically extends along the length of the base member 210. The connector rod 241 is held in manner that will allow it to be freely rotated and can either be left coupled to the base member 210 or be detachably coupled thereto.

Seen in FIG. 22 is the expansion mechanism 240 that includes at least two expansion assemblies 230, a connector drive rod 241 including two worm gears 245 that are positioned next and in contact with the two spiral gears 231 of the two expansion assemblies 230. Detachably coupled to one end of the near worm gear is the expansion tool 290. The end of the expansion tool 290 may be configured as a hex head or other like configuration that will allow for the user to rotate the expansion tool 290 and cause the near worm gear 245, the connector drive rod 241 or both to rotate.

Figure 23:
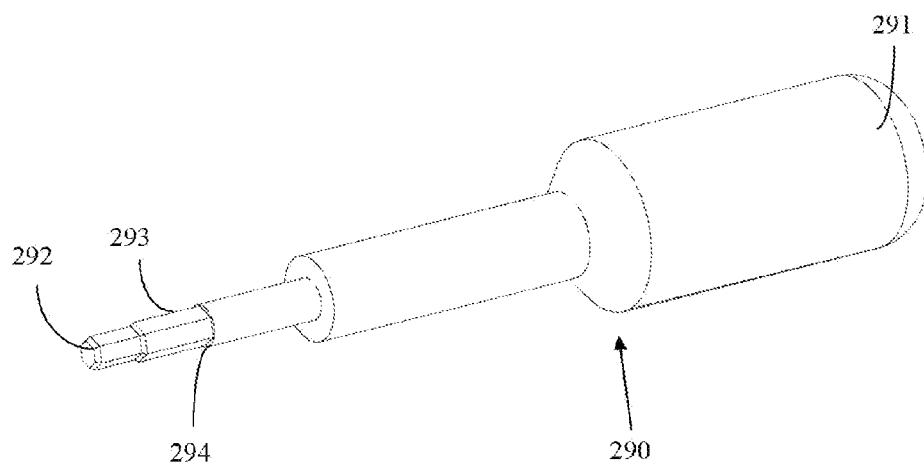
FIG. 23 is a perspective view of the expansion tool, in accordance with an aspect of the present invention.

Each expansion assembly 230 of the expansion mechanism 240 is actuated by rotating an expansion tool, for example, the expansion tool 290. The tool 290 may be configured in various forms, depending upon the number of expansion assemblies 230 that are used in the expansion mechanism 240. For the expansion mechanism 240 example shown in FIG. 22, the tool 290 is shown in FIG. 23. The tool 290 consists of a handle 291 with a near connector end 294 to interface with the near horizontal worm gear 245 that interacts with the near spiral gear 231 of the first expansion assembly 230, a shaft 293 that extends for the distance between the first expansion assembly 230 and the second expansion mechanism 230 and a far connector end 292 to interface with the far horizontal worm gear 245 that interacts with the far spiral gear 231 of the second expansion assembly 230. Both of the connector ends 292, 294 may be configured as, for example, a square male end, although a hex or other multi-lobed configurations may also be used. In use, the connector ends 292, 294 are inserted into an opening or female end or mid shaft of the connector drive rod 241 to ensure that when the handle 291 is rotated, one or both of the worm gears 245, and if applicable, the connector drive rod will rotate at the same speed, thereby causing the two engaged spiral gears 231 of the corresponding two expansion assemblies 230 to also rotate resulting in movement of the superior member 220 in an upward or downward direction depending on the direction of rotation of the tool 290. It is important to note that if the two expansion assemblies are not rotated simultaneously then the superior member 220 may be angled because of the resulting difference in length of the two expansion assemblies 230. The tool 290 may be designed to either rotate the near assembly only, the far assembly only or both at the same time to get equal displacement of the superior member 220. The cogs or teeth of worm gears 237 on the ends of the connector drive rod 241 are sized to mate with the corresponding cogs or teeth of the two spiral gears 231 to facilitate rotation of the spiral gear 231 when the tool 290 is turned.

Figure 24:
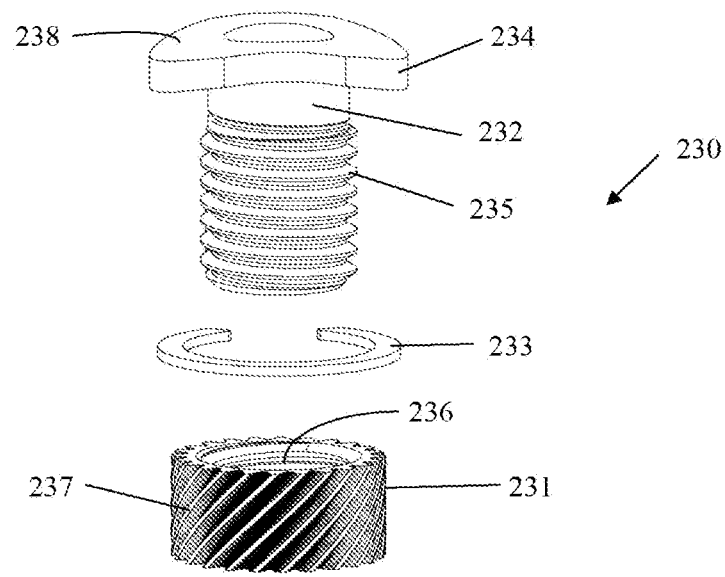
FIG. 24 is an exploded view of one expansion assembly, in accordance with an aspect of the present invention.

The constructed expansion assembly 230 and the various components that comprise it are seen in FIG. 24. FIG. 24 shows an exploded view of the expansion assembly 230 to include the spiral gear ring 231, the threaded rod 232, the load cap 234 and the support means 233. The threaded rod 232 has external threads 235 extending along its length. The rod is typically hollow to allow for bone graft placement. The external threads 235 are configured to match the internal threads 236 of the spiral gear 231. Spiral gear 231 is circular in shape and includes external spiral gears on its outer surface for the entire circumference. The teeth 237 of the spiral gear 231 are configured to allow for mating with the worm gear 245 positioned on the end of the connector drive rod 241. As described above, the expansion assembly 230 acts to convert rotational movement of the spiral gear 231 into translational movement of the threaded rod 232. This is achieved by allowing free rotational motion of the spiral gear 231 while restricting the rotation of the threaded rod 232. By restricting the rotation of the threaded rod 232, the rod translates in either an upward or downward direction relative to the spiral gear ring 231 depending upon whether the threads (external and internal) 235, 236 are oriented in a right-handed or left handed direction. As discussed above, when the threaded rod 232 moves, the load cap 234 contacts the concave area 222 of the undersurface 221 of the top member 220 to either move it away from the base member 210 or towards the base member 200. In another words, the height of the implant 200 either increases or decreases or the bone contacting surfaces 205 will be angled relative to each other depending upon the rotational direction of the tool 290 and also whether individual or both expansion assemblies 230 are engaged.

As shown in FIG. 24, support means 233 is used adjacent to the threaded rod 232 and the spiral gear 231. The support means 233 may be, for example, a snap ring or other similar type of structure that will secure the expansion assembly 230 within the openings 212 of the base member 210 and the top member 220. The support means 233 also facilitates retaining the expansion assembly 230 in a position adjacent to the either the shoulder 213 or tabs 224.

Further, seen in FIG. 24 is the arcuate or convex shaped top surface of the load cap 238. The top surface 238 is configured to slide over the concave area 222 of the undersurface 221 to allow for uneven lengthening of the expansion assemblies 230 to create an angled relationship of the superior member 220 relative to the base member 210. The concave-convex relationship between the top surface 238 and the concave area 22 facilitates the angulation process and the load transfer between the superior member 220 and the base member 210 while avoiding potential binding of the expansion assembly 230 during the expansion and refraction process.

Figure 25:
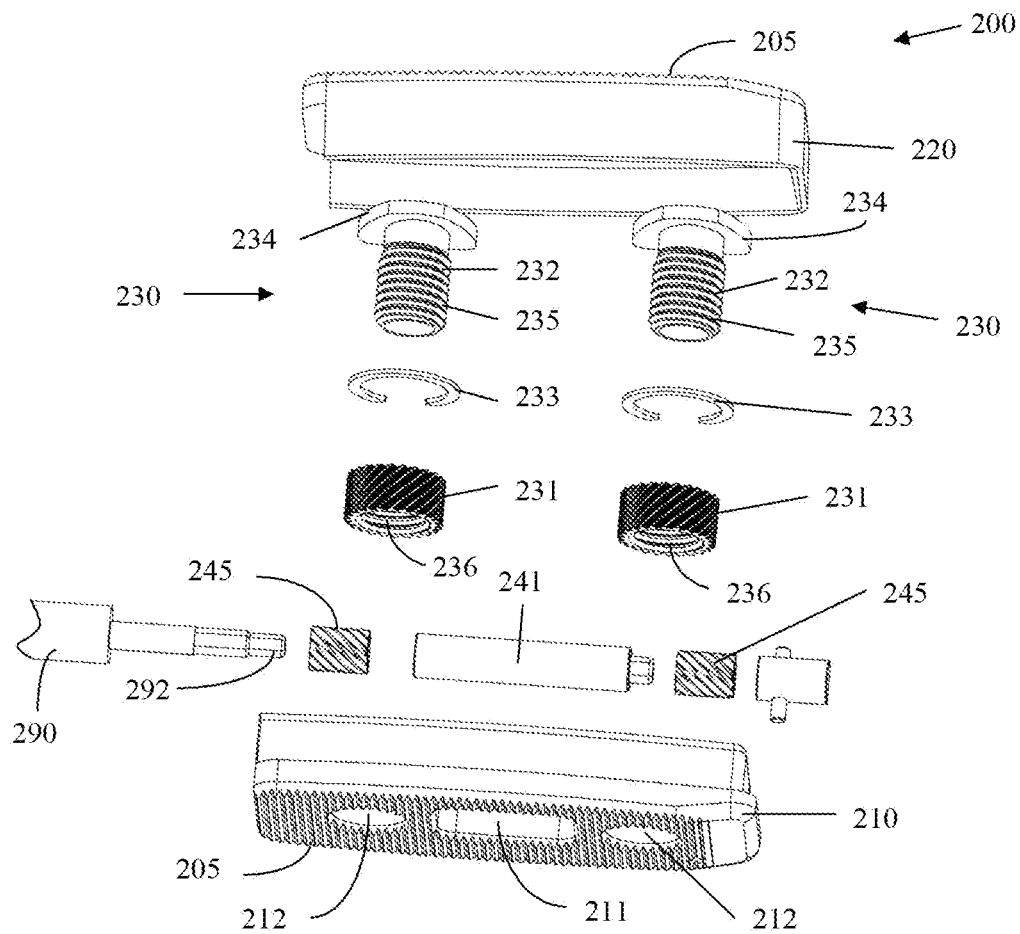
FIG. 25 is an exploded view of the expandable interbody fusion device of FIG. 14, in accordance with an aspect of the present invention.

FIG. 25 shows an exploded view of all of the components that have been described above that comprise the implant 200.

Figure 28:
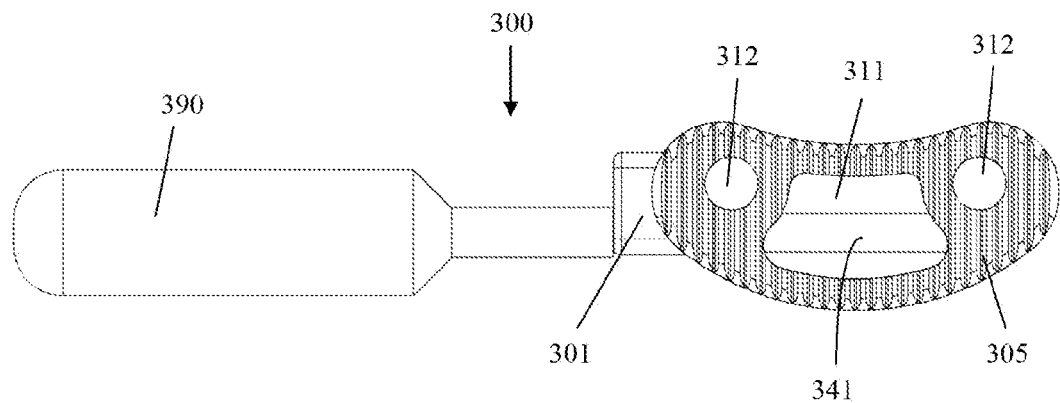
FIG. 28 is a superior view of the expandable interbody fusion device of FIG. 26, in accordance with an aspect of the present invention.

Shown in FIG. 26, is an example of a TLIF unilateral, vertical expandable interbody fusion device 300. The device 300, as seen in FIGS. 26 and 28, has a generally banana or arcuate shaped geometry with convex and concave configured long sides to facilitate insertion and bone coverage within the spine. Although it would be understood by one skilled in the art that other shaped outside configurations can be used. The implant 300 may likely include at least one moveable superior member 320 and a bottom member 310. The superior member 320 may be detachably coupled to the bottom member 310.

As seen in FIGS. 26 and 28, at least one through opening 311 for insertion of bone graft material is disposed on the inferior and superior bone contacting surfaces 305. The opening 311 extends through the external surfaces 305 of the bottom member 310 and the superior member 320. The opening 311 typically extends through both bone contacting surfaces 305 and into the inner cavity of the assembled implant 300. The size and configuration of the opening 311 allows the surgeon to place bone graft material inside the implant 300 to achieve a continuous fusion between the inferior and superior vertebral bodies.

Figure 27:
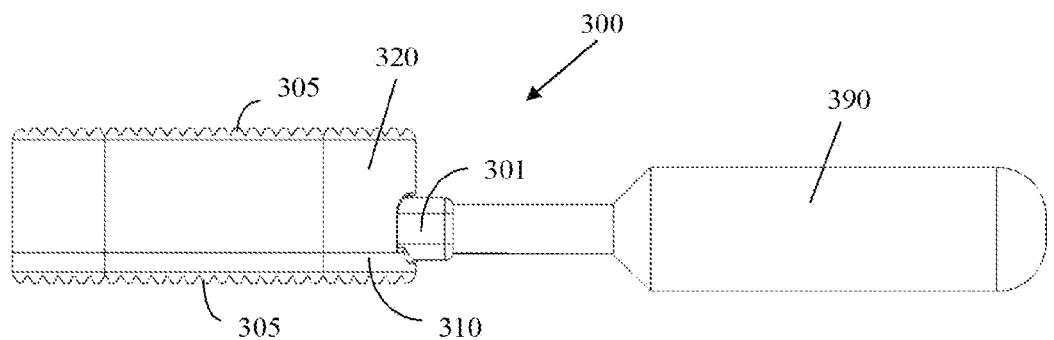
FIG. 27 is a side view of the expandable interbody fusion device of FIG. 26 with the moveable member in a non-extended state, in accordance with an aspect of the present invention.

As shown in FIG. 27, the superior and inferior bone contacting surfaces 305 may be generally parallel to each other. However, it is contemplated that the expansion mechanism 340 (see FIG. 34) may allow the user to angle the bone contacting surface 305 of the superior member 320 relative to the bone contacting surface 305 of the bottom member 310. FIGS. 26-28 show the bone contacting surfaces 305 to have teeth-like or tine structures projecting away from the superior and inferior surfaces. One skilled in the art would recognize that other surface treatments may be applied to the bone contacting surfaces 305 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. It is also understood that the bone contacting surfaces 305 may be coated with nano-surfacing, bioactive or bone ingrowth coatings.

FIG. 28 shows the expansion tool 390 being inserted off-center from the longitudinal axis of the implant 300. The off-center orientation is achieved by the configuration of the expansion mechanism 340 that will be described in greater detail below. The off-center entry point of the tool 390 and the removability after the expansion or retraction process has been completed of the expansion mechanism 340 out of the center of the implant 300 provides the surgeon with the ability to pack a maximum amount of bone graft material through the opening 311 and create a continuous graft from the inferior vertebral body to the superior vertebral body.

Figure 29:
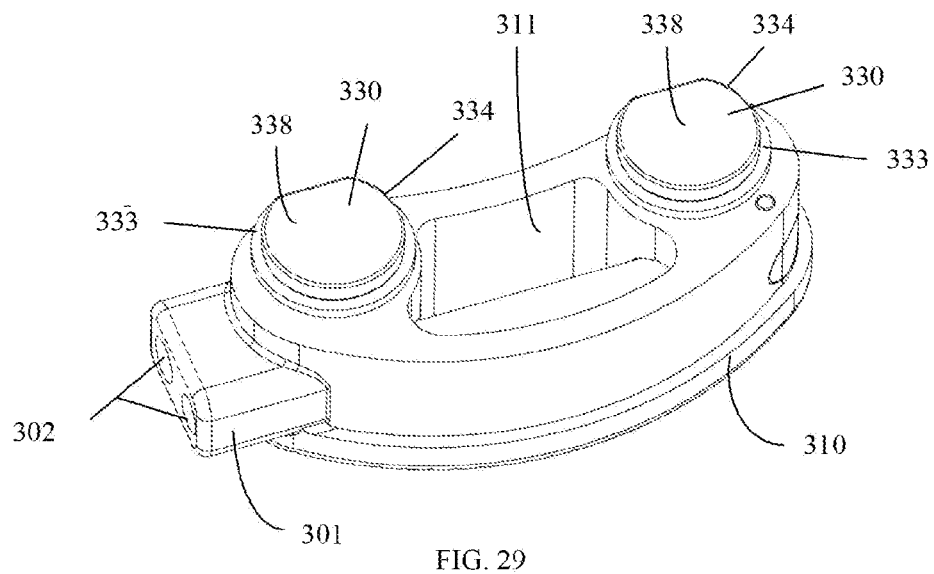
FIG. 29 is a superior perspective view of the expandable interbody fusion device of FIG. 26 showing only the base member with the seated dual expansion assemblies, in accordance with an aspect of the present invention.
Figure 30:
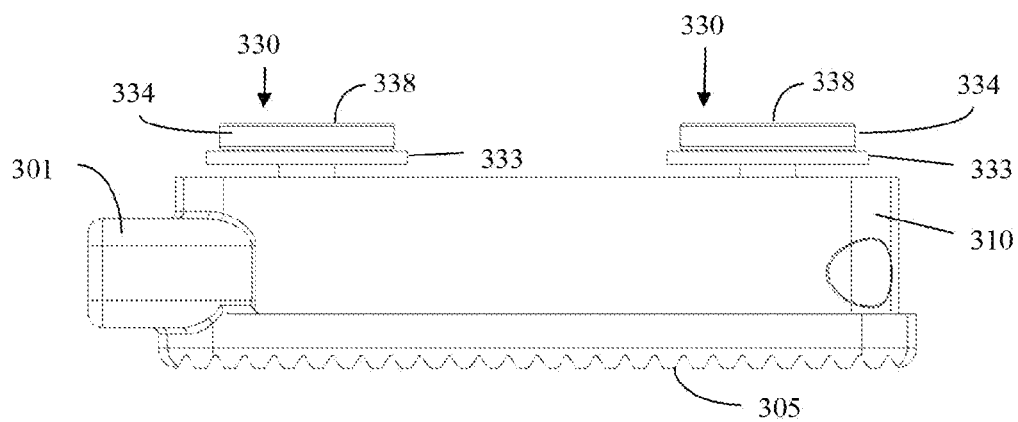
FIG. 30 is a side view of the expandable interbody fusion device of FIG. 26 showing only the base member with the seated dual expansion assemblies, in accordance with an aspect of the present invention.
Figure 31:
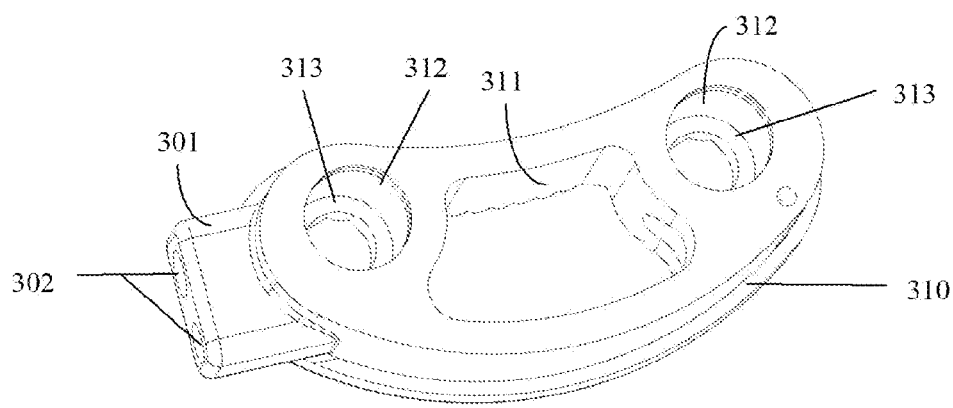
FIG. 31 is a superior perspective view of the expandable interbody fusion device of FIG. 26 showing only the base member, in accordance with an aspect of the present invention.

FIGS. 29 and 31, provide a superior view of the bottom member 310. FIG. 31 exhibits the central opening 311 that allows the surgeon to insert bone graft material into the central cavity of the assembled implant 300 following the implantation. Outer positioned holes 312 are also seen and these are configured to house a portion of the at least two expansion assemblies 330. More specifically, the support means 333, that is adjacent the spiral gear 331 may sit on the internal circumferential shoulder 313 that functions to maintain the expansion assembly 330 in a vertical orientation relative to the bottom member 310. The shoulder 313 also operates as a bearing surface against which the support means 333 contacts. FIGS. 29 and 30 show the two expansion assemblies 330 protruding above a planar inner surface of the bottom member 310 while positioned within outer holes 312 and seated on shoulder 313.

FIGS. 29 and 31 also show positioned on the other surface of bottom member 310 a housing 301 that includes at least two holes 302 that are configured to receive, an expansion tool, for example, the expansion tool 390. The housing 301 extends away from one of the ends of implant 300 to facilitate insertion of tool 390 when engaged with the expansion mechanism 340.

Figure 32:
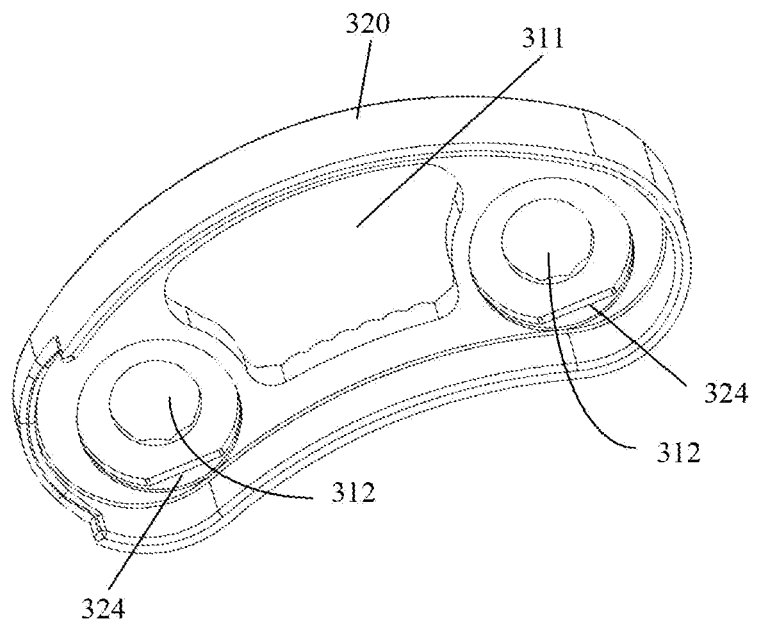
FIG. 32 is an inferior perspective view of the expandable interbody fusion device of FIG. 26 showing only the top or moveable member, in accordance with an aspect of the present invention.
Figure 33:
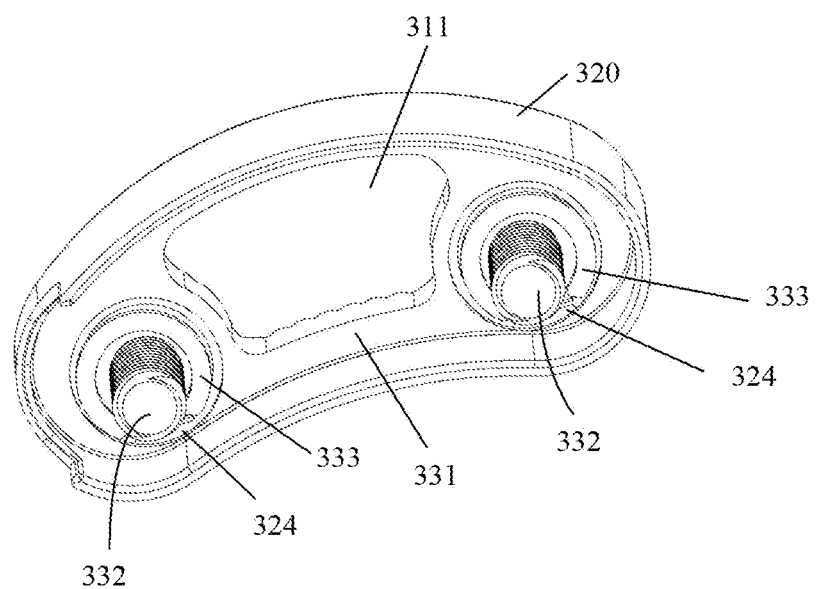
FIG. 33 is an inferior perspective view of the expandable interbody fusion device of FIG. 26 showing only the top or moveable member with the seated dual expansion assemblies, in accordance with an aspect of the present invention.

FIGS. 32 and 33 are inferior views of the undersurface 321 of the superior moveable member 320. FIG. 32 shows the central opening 311 that is configured to permit the surgeon to insert bone graft material into the inner cavity of the implant 300 prior to implantation. Further viewed in these figures are outer holes 312 that align with the corresponding outer holes 312 in the bottom member 310 when the implant 300 is assembled. A ledge 324 is located within holes 312 and may act to retain the expansion assembly 330 and restrict the rotation of the threaded rod 332 by aligning with a corresponding flat surface on the outer perimeter of the load cap 334 of the of the expansion mechanism 340. FIG. 33 shows two expansion assemblies 330 seated within outer holes 312 and aligned with the ledge 324.

As seen in FIG. 32, the undersurface 321 within the outer holes 312 is planar and mirrors the top surface or top portion 338 configuration of the load cap 334 although it may be concave to match with an arc of curvature of a top surface of a load cap if such a design is used in the construct. In the event the superior member has a concave undersurface that matches with a convex top surface on the load cap 334, this will allow the user to angle or tilt the superior member 320 relative to the bottom member 310 by extending one of the at least two expansion assemblies 330 to a different length compared to the other assembly.

Figure 34:
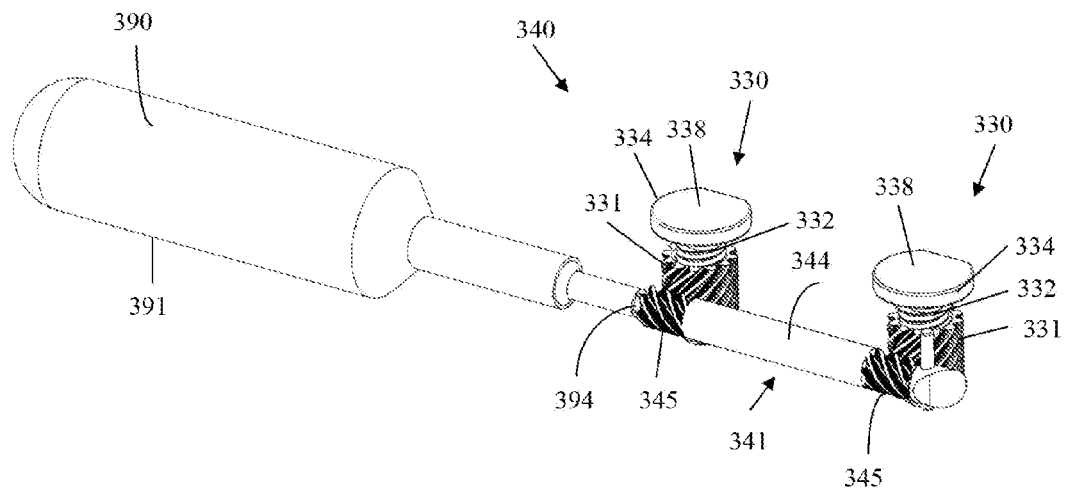
FIG. 34 is a side perspective view of the dual expansion assemblies with the engaged drive connector coupled to an expansion tool, in accordance with an aspect of the present invention.

An alternative expansion mechanism 340 is shown in FIG. 34 and comprises at least two expansion assemblies 330 and a connector drive rod assembly 341. The spacing between the assembled and inserted expansion assemblies 330 typically matches the distance between the outer holes 312. As explained more below, the expansion assembly 330 is comprised of a spiral gear 331, a threaded rod 332, a load cap 334 and multiple support means 333. The expansion mechanism 340 functions to convert rotation movement of the spiral gear 331 into linear or translational movement of the load cap 334 positioned at the upper end of the threaded rod 332. The connector drive rod assembly 341 functions to mirror the rotational movement of the tool 390 and translate this motion to either the first or second spiral gears 331, or alternatively, both simultaneously. Rotation of the spiral gears 331 will result in a travel distance of the threaded rods 332 when the expansion mechanism 340 is actuated by an expansion tool, for example, the expansion tool 390.

The connector drive rod assembly 341 may be comprised of a hollow cylindrical shaft 344 with an opening at one end 343, and two worm gears 345 positioned at either end of the cylindrical shaft 344 to align with the inserted expansion assemblies 330. The worm gears 345 are configured to engage with the two spiral gears 331 of the expansion assemblies 330. When the implant 300 is assembled, the connector drive rod assembly 341 is supported along the floor of the bottom member 310 and eccentrically extends along the length of the bottom member 310. The connector drive rod assembly 341 is held in a manner that will allow it to be freely rotated and can either be left coupled to the bottom member 310 or be detachably coupled to allow the user to remove it once the expansion assemblies 330 are adjusted to their final positions.

Seen in FIG. 34 the expansion mechanism 340 may include at least two expansion assemblies 330, a connector drive rod assembly 341 including two worm gears 345 that are positioned adjacent to the spiral gears 331 of the two expansion assemblies 330. Detachably coupled to one end of the near worm gear 345 is the expansion tool 390. The end of the expansion tool 390 may be configured as, for example, a hex head or other like configuration that will allow for the user to rotate the expansion tool 390 and cause the near worm gear 345, the shaft 344 and the far worm gear 345 all to rotate.

Each expansion assembly 330 of the expansion mechanism 340 is actuated by rotating an expansion tool, for example, the expansion tool 390. The tool 390 may be configured in various forms, depending upon the number of expansion assemblies 330 that are used in the expansion mechanism 340. For the expansion mechanism 340 embodiment shown in FIG. 34, the tool 390 consists of a handle 391 with a connector end 394 to interface with the near horizontal worm gear 345 that interacts with the near spiral gear 331 of the first expansion assembly 330. For the embodiment shown in FIG. 34, the shaft 344 of the connector drive rod assembly 340 couples the near and far worm gears 345 together, resulting in the near and far worm gears 345 rotating at the same time and at the same speed when the tool 390 is turned. The connector end 394 may be configured, for example, as a square male end, although hex or other multi-lobed configurations may be used. In use, the connector end 394 is inserted into an opening or female end of the connector drive rod assembly 341 to ensure that when the handle 391 is rotated, both of the worm gears 345 will rotate at the same speed, thereby causing the two engaged spiral gears 331 of the corresponding two expansion assemblies 330 to also rotate and travel an equal distance causing the superior member 320 to move in either upward or downward direction depending on the direction of rotation of the tool 390. If the two expansion assemblies 330 are not rotated simultaneously then the superior member 320 may be angled because of the resulting difference in length of the two expansion assemblies 330. In that case the tool 390 may be designed to either rotate the near expansion assembly only, the far assembly only or both at the same time to get equal displacement of the superior member 320. The cogs or teeth of the worm gears 345 connected to the shaft 344 are sized to mate with the corresponding cogs or teeth of the spiral gear 331 to rotate the spiral gear 331 when the tool 390 is engaged with the connecting drive rod assembly 341.

Figure 35:
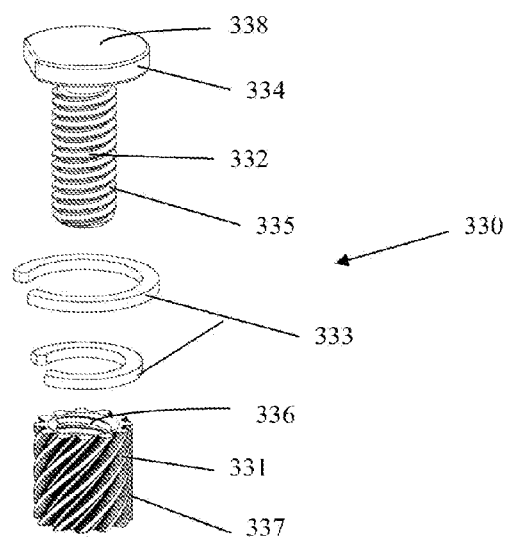
FIG. 35 is an exploded view of one expansion assembly, in accordance with an aspect of the present invention.

The constructed expansion assembly 330 and the various components that comprise it are seen in FIG. 35. FIG. 35 shows an exploded view of the expansion assembly 330 to include the spiral gear ring 331, the threaded rod 332, the load cap 334 and the support means 333. The threaded rod 332 has external threads 335 extending along its length. The rod 332 may be hollow (not shown) to allow for bone graft placement. The external threads 335 are configured to match the internal threads 336 of the spiral gear 331. Spiral gear 331 is circular in shape and includes external teeth 337 that form a spiral gear on its outer surface for the entire circumference. The teeth 337 are configured to allow for mating with the worm gear 345 of the connector drive rod assembly 341. As described above, the expansion assembly 330 acts to convert rotational movement of the spiral gear 331 into translational movement of the threaded rod 332. This is achieved by allowing free rotational motion of the spiral gear 331 while restricting the rotation of the threaded rod 332. By restricting the rotation of the threaded rod 332, the load cap 334 translates in either an upward or downward direction relative to the spiral gear 331 depending upon whether the threads (external and internal) 335, 336 are oriented in a right-handed or left handed direction. As discussed above, when the threaded rod 332 moves, the top surface of the load cap 338 contacts the undersurface 321 of the superior member 320 to either move it away from the bottom member 310 or towards the bottom member 310. In other words, the height of the implant 300 either increases or decreases depending upon the rotational direction of the tool 390. As shown, the top surface 338 of the load cap 334 is planar and solid so as to function to block the opening of the outer holes 312 (see FIG. 28).

As seen in FIG. 35, support means 333 are used both adjacent to the load cap 334 and the spiral gear 331. The support means may be a snap ring or other similar type of structure that will secure the expansion assembly 330 within the openings 312 of the bottom member 310 and the top member 320. The support means 333 also facilitates retaining the expansion assembly 330 in a position adjacent to the either the shoulder 313 or the ledge 324.

Although not shown, the top surface 338 of the load cap is planar, however, it is understood by one skilled in the art that in an alternative embodiment of implant 300 that the top surface may be arcuate or convex shaped like shown in FIG. 24. Similar to as described above, if this were the case, then the top surface would slide over a concave area on the undersurface 321 of the superior member 320 to allow for uneven lengthening of the expansion assemblies 330 and create an angled relationship between the superior member 320 relative to the bottom member 310. The concave-convex relationship between the top surface or top portion of the load cap 334 and the concave area disposed on the undersurface 321 would facilitate the angulation process and the load transfer between the superior member 320 and the bottom member 310 while avoiding potential binding of the expansion assembly 330 during the expansion and retraction process.

Figure 36:
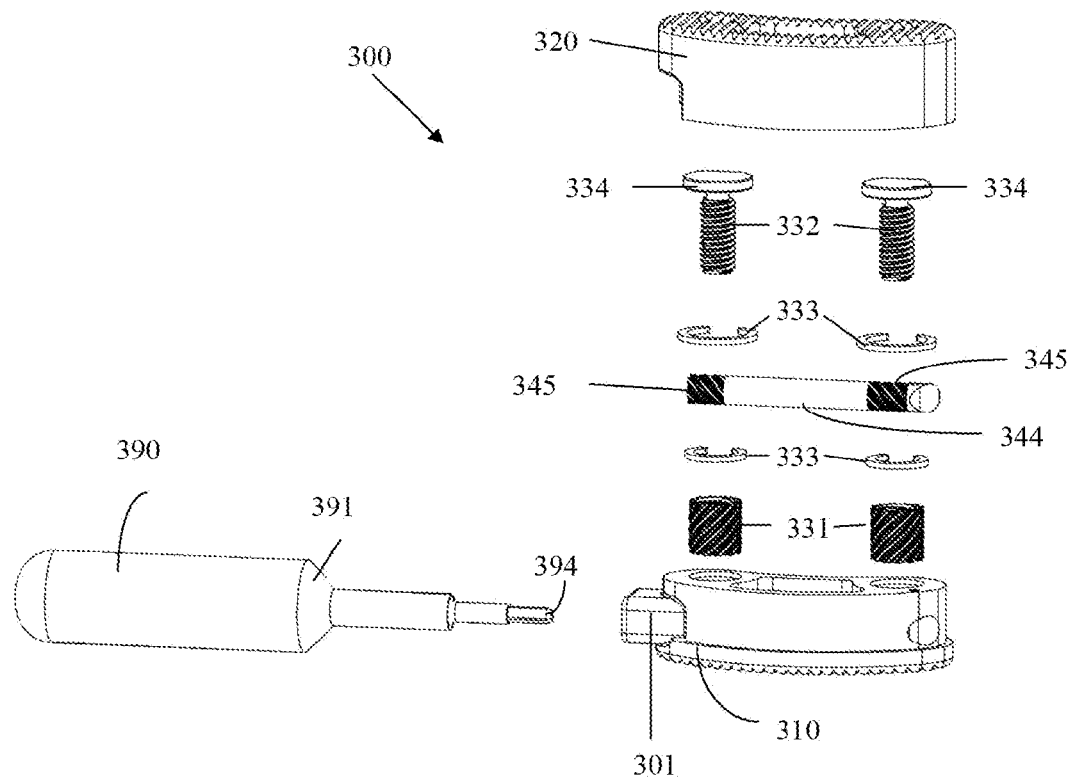
FIG. 36 is an exploded view of the expandable interbody fusion device of FIG. 26, in accordance with an aspect of the present invention.

FIG. 36 shows an exploded view of all of the components that have been described above that comprise the implant 300.

Figure 37:
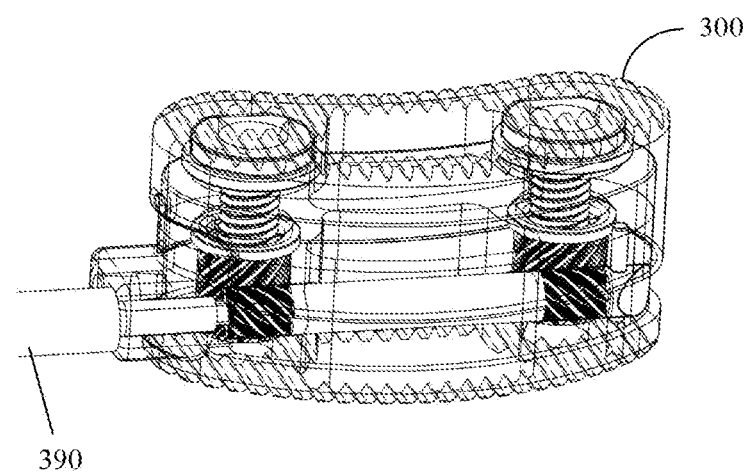
FIG. 37 is a partially transparent, perspective view of the expandable interbody fusion device of FIG. 26 with an inserted expansion tool, in accordance with an aspect of the present invention.

FIG. 37 is a transparent view of the implant 300 with the engage expansion tool 390. FIG. 37 shows the worm gears 345 of the tool 390 engaged with the spiral gears 331 of the two expansion assemblies 330.

Figure 39:
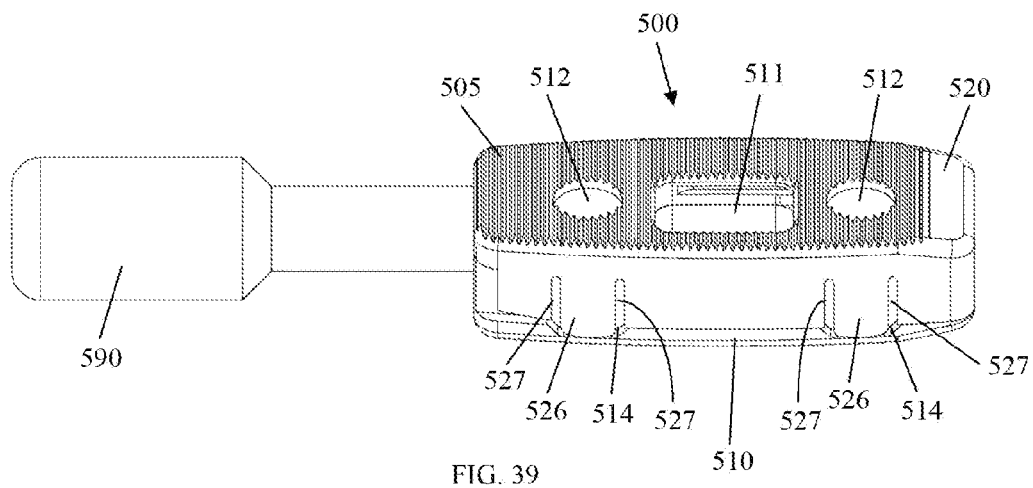
FIG. 39 is an anterior perspective view of the expandable interbody fusion device of FIG. 38 showing both ends in a retracted position, in accordance with an aspect of the present invention.
Figure 40:
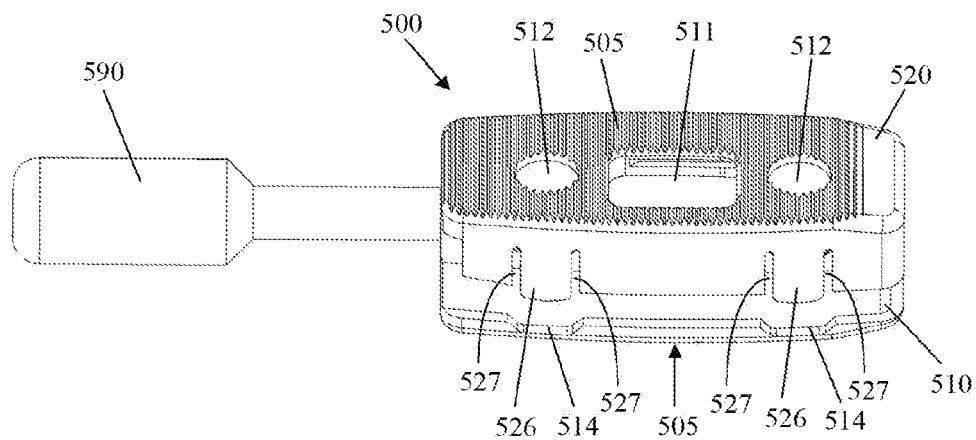
FIG. 40 is an anterior perspective view of the expandable interbody fusion device of FIG. 38 showing both ends in an extended or expanded position, in accordance with an aspect of the present invention.

Shown in FIG. 38, is yet another example of a unilateral, vertical expandable interbody fusion device 500. The device 500 as seen in FIGS. 38-40, has a generally rectangular geometry, similar to device 100 described above with reference to FIGS. 1-4 and for brevity sake will not be described again. The implant 500 may likely include at least one moveable top or superior member 520 and a base or bottom member 510. The superior member 520 may be detachably coupled to the base member 510.

As seen in FIGS. 38-40, at least one through central opening 511 for insertion of bone graft material is disposed on the inferior and superior bone contacting surfaces 505. The opening 511 typically extends through both bone contacting surfaces (of superior and base members) 505 and into the inner cavity of the assembled implant 500. The size and configuration of the opening 511 allows the surgeon to place bone graft material inside the implant 500 to achieve a continuous fusion between the inferior and superior vertebral bodies.

As shown in FIG. 40, the superior and inferior bone contacting surfaces 505 may be generally parallel to each other. However, the expansion mechanism 540 (see FIG. 42) will allow the user to angle the bone contacting surface 505 of the superior member 520 relative to the bone contacting surface 505 of the base member 510 as seen in FIG. 38. FIGS. 38-41 show the bone contacting surfaces 505 to have teeth-like or tine structures projecting away from the superior and inferior surfaces. One skilled in the art would recognize that other surface treatments may be applied to the bone contacting surfaces 505 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. It is also understood that the bone contacting surfaces 505 may be coated with nano-surfacing, bioactive or bone/tissue ingrowth coatings.

Figure 41:
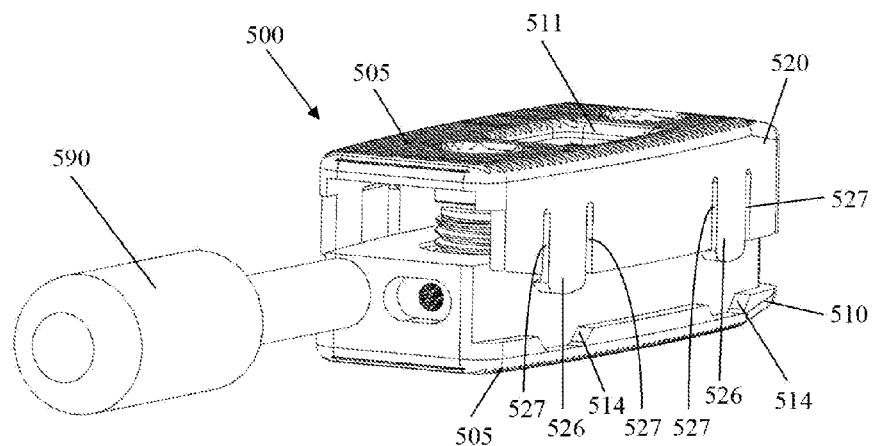
FIG. 41 is a lateral perspective view of the expandable interbody fusion device of FIG. 38 showing both ends in an extended or expanded position, in accordance with an aspect of the present invention.

FIG. 41 shows an expansion tool 590 being inserted off-center from the longitudinal axis of the implant 500. The off-center orientation is achieved by the configuration of the expansion mechanism 540 that will be described in more detail below. The off-center entry point of the tool 590 and the corresponding elimination of the expansion mechanism 540 along the center longitudinal axis of the implant 500 provides the surgeon with the ability to pack a maximum amount of bone graft material through the opening 511 and create a continuous graft from the inferior vertebral body to the superior vertebral body because the opening 511 is unobstructed by any tool or actuation shaft and extends entirely through the implant 500.

Figure 42:
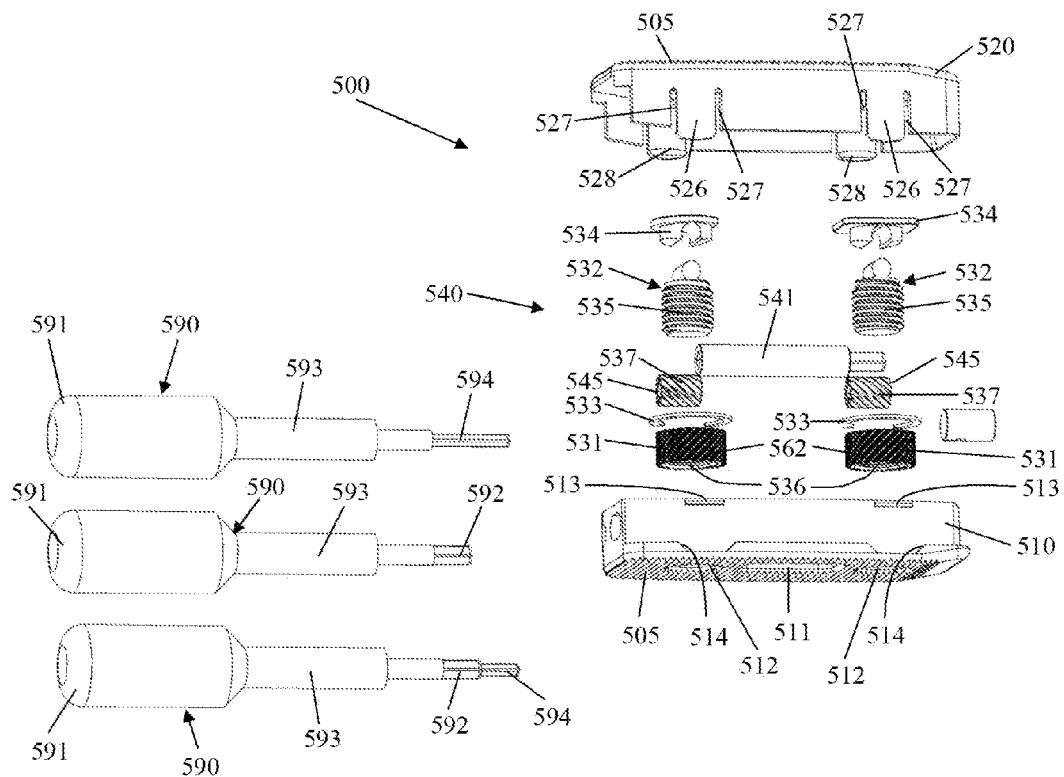
FIG. 42 is an exploded view of the expandable interbody fusion device of FIG. 38 and three adjustment tool embodiments; in accordance with an aspect of the present invention.

Also seen in FIGS. 38-40 are peripherally positioned holes 512 which are configured to house a portion of the at least two expansion assemblies 530. Shown in the exploded view of FIG. 42 are the support means 533, that are adjacent the gear ring 531 and may sit on the internal circumferential shoulder 513 that functions to maintain the expansion assembly 530 in a vertical orientation relative to the base member 510 and aligned with holes 512. The shoulder 513 (see FIG. 19 with 213) also may operate as a bearing surface against which the support means 533 contacts.

Figure 45:
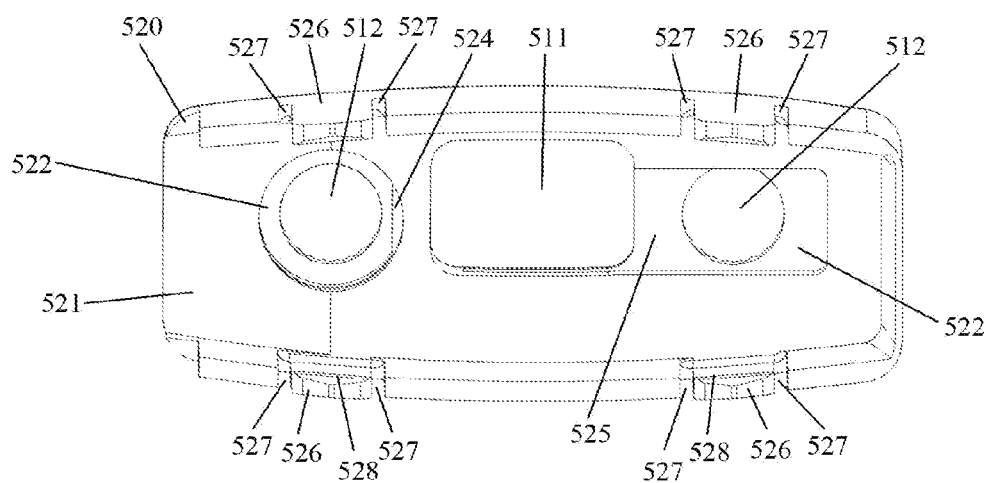
FIG. 45 is an inferior perspective view of the expandable interbody fusion device of FIG. 38, showing only the top or moveable member, in accordance with an aspect of the present invention.
Figure 46:
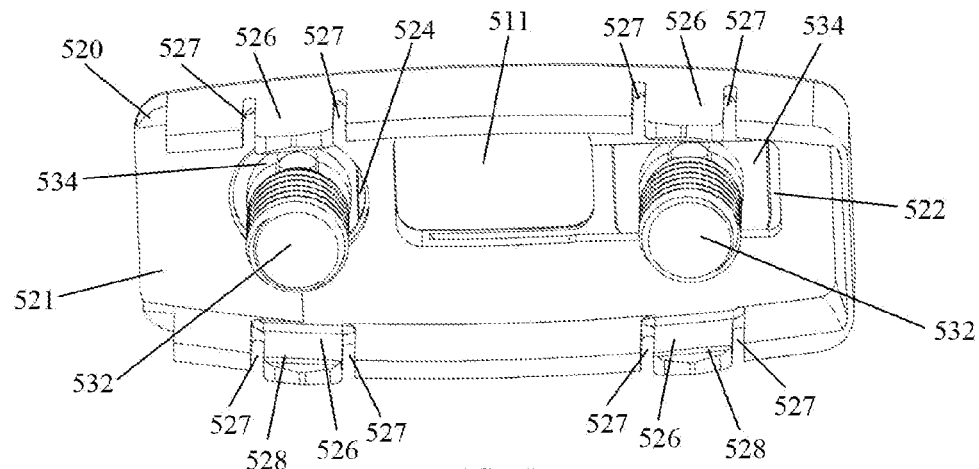
FIG. 46 is an inferior perspective view of the expandable interbody fusion device of FIG. 38, showing the two expansion assemblies seated within the top or moveable member, in accordance with an aspect of the present invention.

FIGS. 45 and 46 are inferior views of the undersurface 521 of the superior moveable member 520. FIG. 45 shows the central opening 511 that is configured to permit the surgeon to insert bone graft material into the inner cavity of the implant 500 prior to implantation. Further viewed in this figure are peripheral holes 512 that align with the corresponding peripheral holes in the base member 510 when the implant 500 is assembled. For one of the holes, an anti-rotation tab 524 is located adjacent to one of the sides of the hole 512 and may act to retain one of the load heads 534 of the expansion assembly 530 as well as restrict rotation of the threaded rod 532. FIG. 46 shows the two load heads 534 positioned within the relief areas 522 of the superior member 520.

As seen in FIG. 45, the relief area 522 surrounding the holes 512 is substantially planar. Around the first hole, the relief area 522 is concentric with the hole 512 and with the anti-rotation tab 524 extending inward towards the center of the hole. The expansion assembly 530 shown in FIG. 43 has a load head 534 that includes a planar portion on one side 563 that will be aligned with anti-rotation tab 524 in the circular relief area 522 of the first hole 512. When these two structures are aligned they function to keep the threaded rod 532 from rotating when the spiral gear 531 is turned. FIG. 46 shows the planar portion 563 adjacent the tab 524 when inserted. For the second hole 512, the relief area is rectangular 525 with the long axis of the rectangle extending along the longitudinal axis of the top member 520. The rectangular relief area 525 is configured to mate with a correspondingly shaped load head 534. The combination of the rectangular shaped load head 534 and the rectangular relief area 525 allows the user to angle or tilt the superior member 520 relative to the base member 510 by extending the at least two expansion assemblies 530 to different lengths.

Shown in FIGS. 38-41 and 45-46, the top or superior member 520 also may include four extension struts 526 that extend below the long side walls of the member 520. The struts 526 have two slots 527 on either side that separate the struts 526 from the side wall construct. Positioned at the inferior end of the strut is a locking tab 528 that engages with a corresponding locking notch 513 (see FIG. 42) that is positioned along the top edge of the long wall of the base member 510. In addition, a nesting seat 514 is aligned directly opposite the locking notch 513 at the inferior edge of the long side wall.

An alternative expansion mechanism 540 is shown in FIG. 42 and comprises at least two expansion assemblies 530 and a connector drive rod 541 that spans the gap between the two expansion assemblies 530. The spacing between the expansion assemblies 530 typically matches the distance between the peripheral holes 512. As explained more below, the expansion assembly 530 is comprised of a spiral gear 531, a threaded rod 532, a load head 534 and multiple support means 533. The expansion mechanism 540 functions to convert rotation movement of the spiral gear 531 into linear or translational movement of the load head 534 positioned at the superior end of the threaded rod 532. The connector drive rod 541 with the two worm gears 545 functions to mirror the rotation movement of an expansion tool, for example, the tool 590 and translate this to either the first or second spiral gears 531, or alternatively, both at the same time. Rotation of the spiral gears 531 will result in a travel distance of the threaded rods 532 when the expansion mechanism 540 is actuated by the expansion tool 590.

Figure 47:
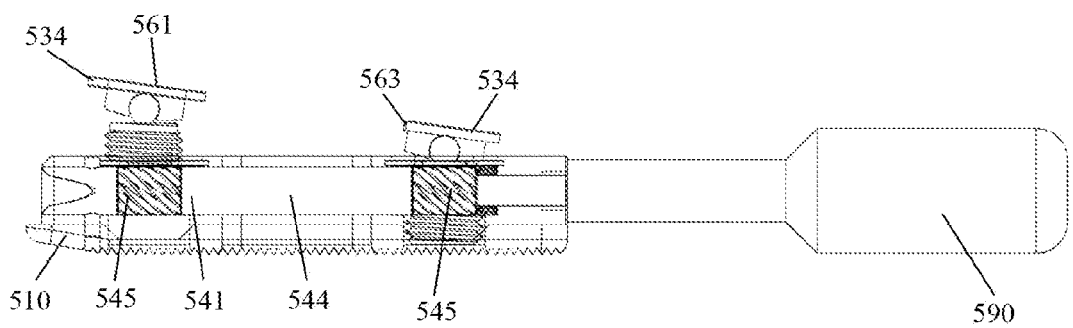
FIG. 47 is a side elevational view of the expandable interbody fusion device of FIG. 38, showing the two expansion assemblies tilted to accommodate the slanted top member and the adjustment tool engaged with the expansion mechanism, in accordance with an aspect of the present invention.

As seen in FIG. 47, the connector drive rod 541 may be comprised of a hollow cylindrical shaft 544 with an opening at one end 543 for coupling with the tool 590, and two worm gears 545 positioned at either end of the connector drive rod 541. The worm gears 545 are configured to engage with the two spiral gears 531 of the expansion assemblies 530.

FIG. 47 shows the assembled implant 500 with the connector drive rod 541 eccentrically positioned and extending through length of the base member 510. The connector rod 541 is held in manner that will allow it to be freely rotated and can either be left coupled to the base member 510 or be detachably coupled thereto.

FIG. 42 shows three different configured expansion tools 590, designed to engage (from top to bottom) respectively, the far expansion assembly, the near expansion assembly and both expansion assemblies simultaneously. The end of the expansion tool 590 may be configured, for example, as a hex head or other like configuration that will allow for the user to rotate the expansion tool 590 and cause the expansion mechanism 540 to rotate.

As noted above, the tool 590 may be configured in various forms, depending upon the number of expansion assemblies 530 that are used in the expansion mechanism 540. The tool 590 may consist of a handle 591, a shaft 593 that extends to one of the connector ends. The tool 590 may be configured with an extended connector end 594 to engage the far expansion assembly only after passing through the connector drive rod 541 (see top tool in FIG. 42). Alternatively, the tool 590 may only have a short connector end 592 for connecting with the near expansion assembly, (see middle tool in FIG. 42), or a combination of both connector ends 592, 594 that will allow the user to engage both expansion assemblies simultaneously, (see bottom tool in FIG. 42). Both connector ends 592, 594 may be configured, for example, as a square male end, although a hex or other multi-lobed configurations may be used. It is important to note that if the two expansion assemblies are not rotated simultaneously then the superior member 520 may be angled because of the resulting difference in length of the two expansion assemblies 530, (see FIGS. 38 and 47). The cogs or teeth 537 of worm gears 545 on the ends of the connector drive rod 541 are sized to mate with the corresponding cogs or teeth 562 of the two spiral gears 531 to facilitate rotation of the spiral gear 531 when the tool 590 is turned.

Figure 43:
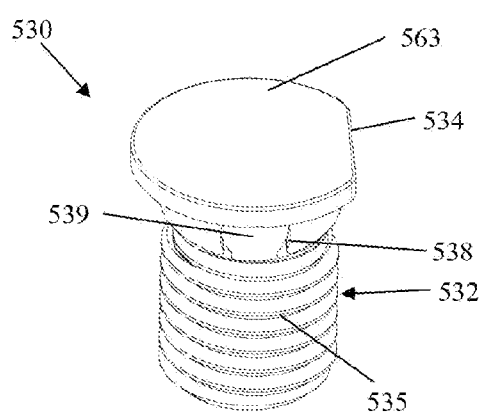
FIG. 43 is a top perspective view of one expansion assembly, in accordance with an aspect of the present invention.
Figure 44:
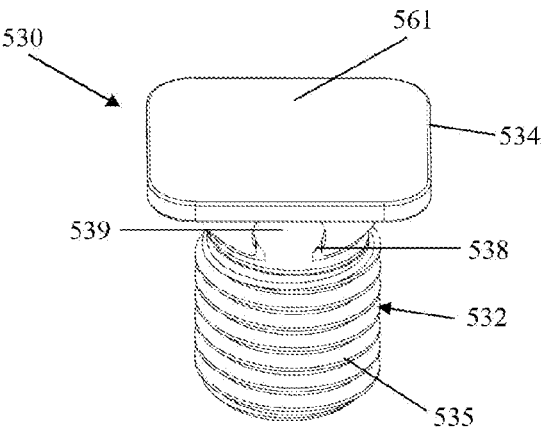
FIG. 44 is a top perspective view of a second moveable expansion assembly, in accordance with an aspect of the present invention.

Two alternative embodiments of the constructed expansion assembly 530 and the various components that comprise them are seen in FIGS. 43 and 44. FIG. 43 shows a top perspective view of one expansion assembly 530. FIG. 42 also shows an exploded view of the two different embodiments of the expansion assemblies 530. Both assemblies may be comprised of a support means 533 that may be in the form of a ring/washer, the threaded rod 532 with a pivot cylinder 539 located on the top or superior end of the rod, the load head 534 that includes a distal channel 538. The outer configuration of the superior head surface may be circular (see FIG. 43) or rectangular shaped (see FIG. 44) to match with the corresponding relief on the under surface 521 of the top member 520. The threaded rod 532 has external threads 535 extending along its length. The external threads 535 are configured to match the internal threads 536 of the spiral gear 531 (see FIG. 42). Spiral gear 531 is circular in shape and includes external spiral gears on its outer surface for the entire circumference. The teeth 562 of the spiral gear 531 are configured to allow for mating with the teeth 537 of the worm gear 545 positioned on the end of the connector drive rod 541. As described above, the expansion assembly 530 acts to convert rotational movement of the spiral gear 531 into translational movement of the threaded rod 532. This is achieved by allowing free rotational motion of the spiral gear 531 while restricting the rotation of the threaded rod 532. By restricting the rotation of the threaded rod 532, the rod translates in either an upward or downward direction relative to the spiral gear 531 depending upon whether the threads (external and internal) 535, 536 are oriented either in a right-handed or left handed direction. As discussed above, when the threaded rod 532 moves, the load head 534 contacts the relief of the undersurface 521 of the top member 520 to either move it away from or towards the base member 510. In another words, the height of the implant 500 either increases or decreases or the bone contacting surfaces 505 will be angled relative to each other depending upon the rotational direction of the tool 590 and also whether individual or both expansion assemblies 530 are engaged.

As shown in FIG. 42, the support means 533 is used adjacent to the threaded rod 532 and the spiral gear 531. The support means 533 may be, for example, a snap ring or other similar type of structure that will secure the expansion assembly 530 within the openings 512 of the base member 510 and the top member 520. The support means 533 also may act as a bearing surface to facilitate the rotation of the expansion assembly 530 when actuated.

Further seen in FIGS. 43 and 44, is the assembled expansion assembly 530 with the pivot cylinder 539 inserted into the distal channel 538 of the load head 534. This construct allows the load head 534 to pivot or slide around the outer diameter of the cylinder 539 when the threaded rods 532 are extended to two different lengths causing the top member 520 to tilt or slant. FIG. 47 shows how load heads 534 are capable of tilting or canting. The rectangular top surface or top portion 561 is configured to slide along the relief 525 of the undersurface 521 to allow for uneven lengthening of the expansion assemblies 530 to create the angled relationship of the superior member 520 relative to the base member 510. The rectangular relief 525 in the undersurface 521 and the rectangular shaped load head 534 facilitates the angulation process and the load transfer between the superior member 520 and the base member 510 while avoiding potential binding of the expansion assembly 530 during the expansion and retraction process. FIG. 42 shows an exploded view of all of the components that have been described above that comprise the implant 500.

Figure 49:
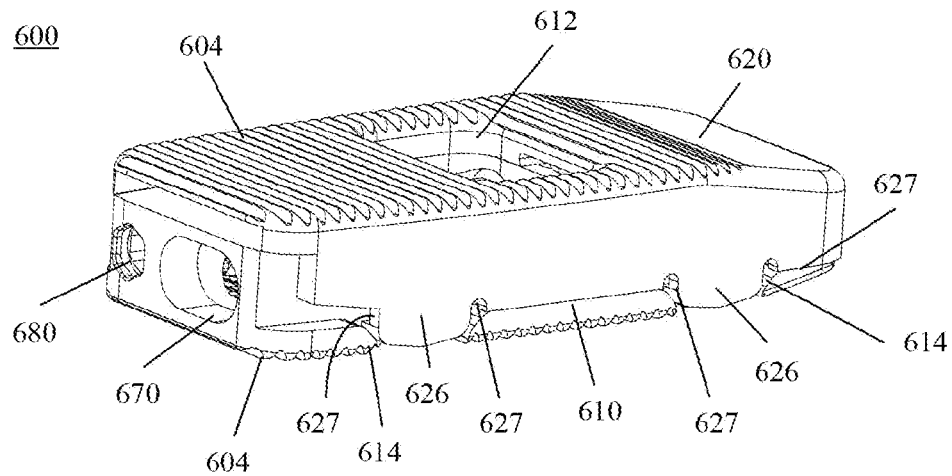
FIG. 49 is a lateral perspective view of the expandable interbody fusion device of FIG. 48 showing both ends in a retracted position, in accordance with an aspect of the present invention.
Figure 50:
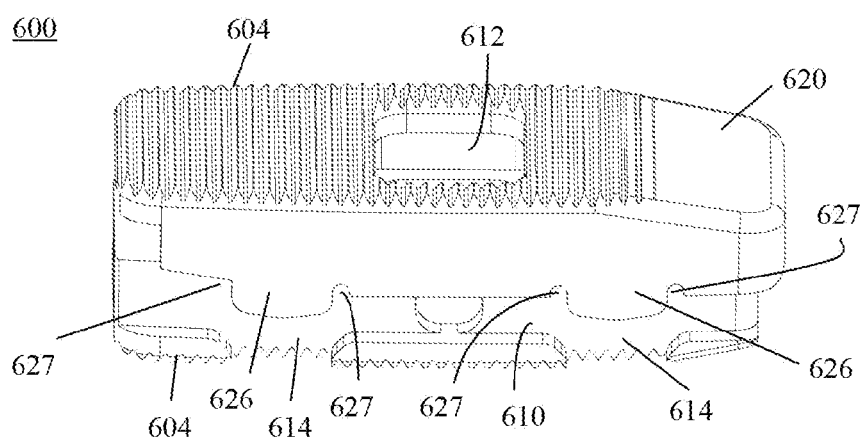
FIG. 50 is an anterior perspective view of the expandable interbody fusion device of FIG. 48 showing both ends in an extended or expanded position, in accordance with an aspect of the present invention.

Referring now to FIGS. 48-56, is another example of a unilateral, vertical expandable interbody fusion device 600. The device 600 as seen in FIGS. 48-50, has a generally rectangular geometry with various configured long sides to facilitate insertion and bone coverage. Although it would be understood by one skilled in the art that other outside shaped configurations may be used. For example purposes, the long sides are slightly arcuate although it is contemplated that other geometrical shapes may also be used in the construct. The device 600 may have a tapered or angled bullet tip end on both the top or superior member 620 and base or bottom member 610 for facilitating insertion into the space between the superior and inferior vertebral bodies. The implant 600 may likely include at least one moveable top or superior member 620 and a base or bottom member 610. The superior member 620 may be detachably coupled to the base member 610.

As seen in FIGS. 48-50, at least one through central opening 612 for insertion of bone graft material is disposed on the inferior and superior bone contacting surfaces 604. The opening 612 typically extends through both bone contacting surfaces (of superior and base members) 604 and into the inner cavity of the assembled implant 600. The size and configuration of the opening 612 allows the surgeon to place bone graft material inside the implant 600 to achieve a continuous fusion between the inferior and superior vertebral bodies.

As shown in FIG. 50, the superior and inferior bone contacting surfaces 604 may be generally parallel to each other. However, the expansion mechanism 640 (see FIG. 52) will allow the user to angle the bone contacting surface 604 of the base member 610 as seen in FIG. 48, wherein the near end is expanded and the far end is retracted. In addition, the expansion mechanism 640 allows for the far end to be expanded while the near end is retracted. FIGS. 48-51 show the bone contacting surfaces 604 to have teeth-like or tine structures projecting away from the superior or inferior surfaces. One skilled in the art would recognize that other surface treatments may be applied to the bone contacting surfaces 604 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. It is also understood that the bone contacting surfaces 604 may be coated with nano-surfacing, bioactive or bone/tissue ingrowth coatings.

Figure 51:
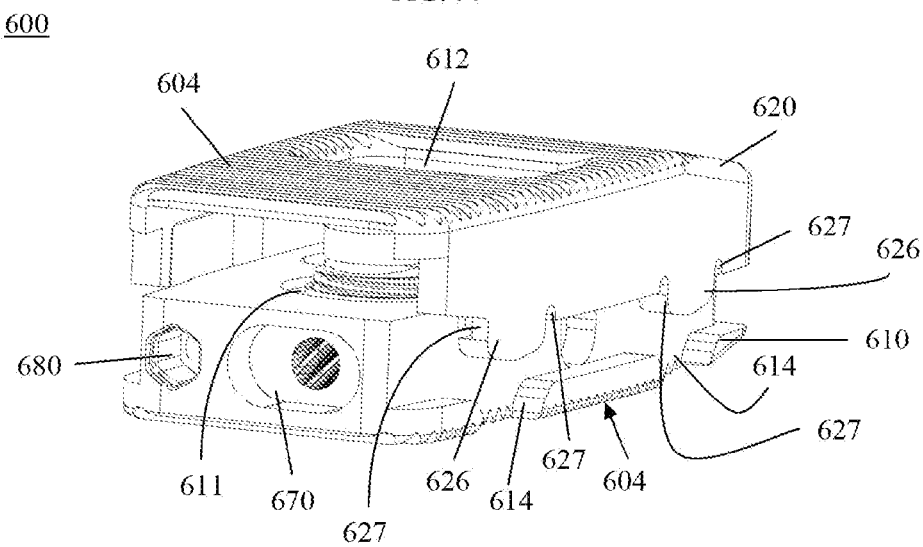
FIG. 51 is a lateral perspective view of the expandable interbody fusion device of FIG. 48 showing both ends in an extended or expanded position, in accordance with an aspect of the present invention.

FIG. 51 shows the expansion tool opening 680 off-center from the longitudinal axis of the implant 600. The off-center orientation is achieved by configuration of the expansion mechanism 640 that will be described in more detail below. The off-center expansion tool opening 680 and the corresponding elimination of the expansion mechanism 640 along the center longitudinal axis of the implant 600 provides the surgeon with the ability to pack a maximum amount of bone graft material through the opening 612 and create a continuous graft from the inferior vertebral body to the superior vertebral body because the opening 612 is unobstructed by any tool or actuation shaft and extends entirely through the implant 600. The implant 600 may also include a locking opening 670 relatively parallel to the tool opening 680 on the end of the base member 610 for securing a tool, for example, tool 900 to the implant 600 during extension and/or retraction. Once the desired height and/or angulation is achieved, a locking insert 920 may be inserted into the expansion tool opening 680 to secure the implant 600 in the desired extension and/or retraction.

Figure 52:
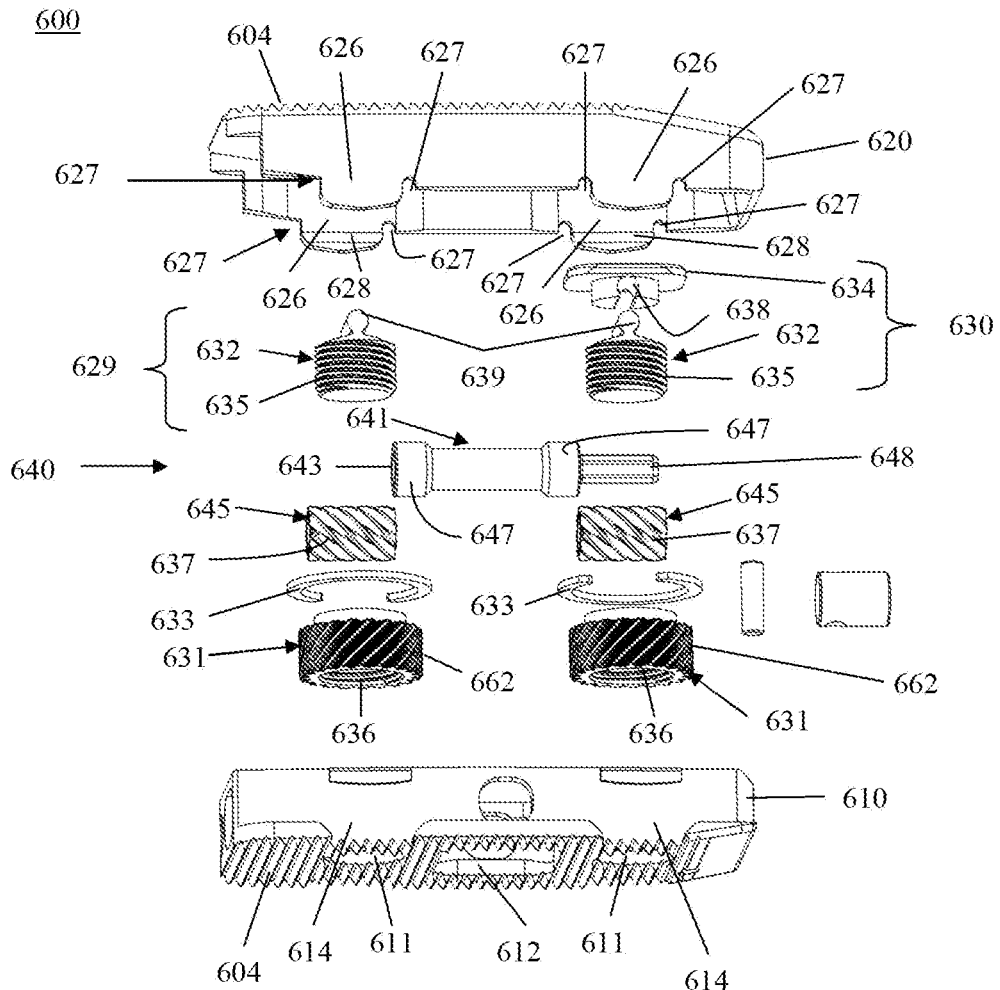
FIG. 52 is an exploded view of the expandable interbody fusion device of FIG. 48, in accordance with an aspect of the present invention.
Figure 55:
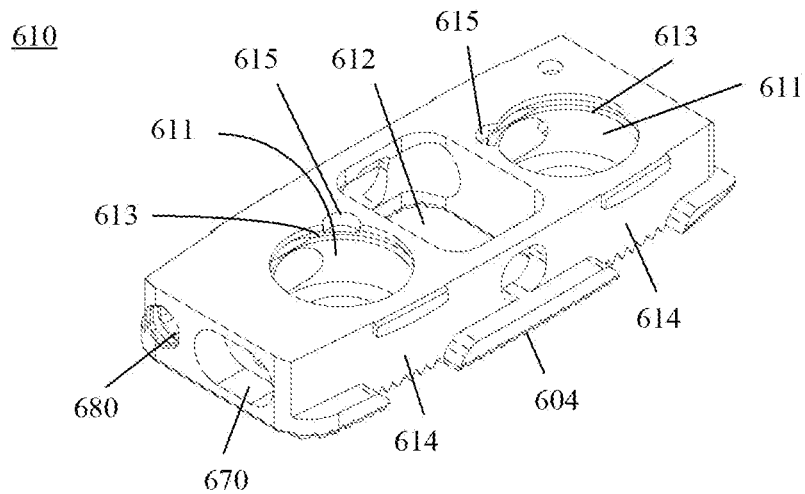
FIG. 55 is a posterior perspective view of the expandable interbody fusion device of FIG. 48, showing only the base or bottom member, in accordance with an aspect of the present invention.

FIG. 52 shows an exploded view of all of the components that comprise the implant 600. Specifically, shown in the exploded view of FIG. 52 are the support means 633, that are adjacent the gear ring 631 and may sit on the internal circumferential shoulder 613 that functions to maintain the expansion assembly 630 in a vertical orientation relative to the base member 610 and aligned with holes 611. The holes 611 or lumens may have smooth vertical walls to facilitate insertion and unrestricted rotation of the gear ring 631. The shoulder 613, illustrated in FIG. 55, also may operate as a bearing surface against which the support means 633 contacts. Also seen in FIG. 55 are peripherally positioned holes 611 which are configured to house a portion of the two expansion assemblies 629, 630. The gear rings 631 may nest or be suspended within the holes 611 by the support means 633 which may engage the shoulder 613. The holes 611 may include notches 615 that intersect the shoulders 613 to enable the insertion of the support means 633.

Figure 53:
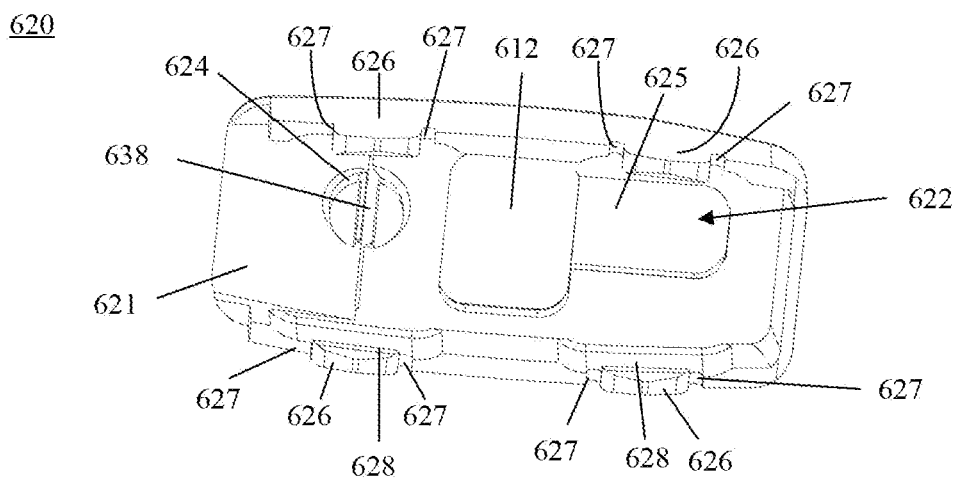
FIG. 53 is an inferior perspective view of the expandable interbody fusion device of FIG. 48, showing only the top or moveable member, in accordance with an aspect of the present invention.
Figure 54:
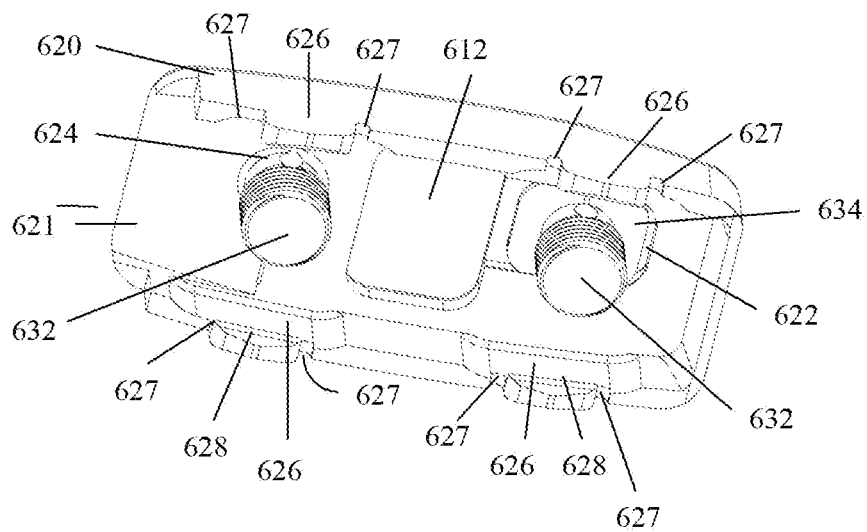
FIG. 54 is an inferior perspective view of the expandable interbody fusion device of FIG. 48, showing the two expansion assemblies seated within the top or moveable member, in accordance with an aspect of the present invention.

FIGS. 53 and 54 are inferior views of the undersurface 621 of the superior moveable member 620. FIG. 53 shows the central opening 612 that is configured to permit the surgeon to insert bone graft material into the inner cavity of the implant 600 prior to implantation. A relief area 622 on the undersurface 621 of the superior member 620 is adjacent to the central opening 612. A flush load head 624 protrudes from the undersurface 621 of the superior member 620 adjacent the central opening 612 and opposite the relief area 622. FIG. 54 shows the load head 634 positioned within the relief area 622 of the superior member 620 and a threaded rod 632 inserted into the flush load head 624 protruding from the undersurface 621 of the superior member 620.

As seen in FIG. 53, the relief area 622 is substantially planar and the relief area 622 is aligned with one of the holes 611 in the base member 610. The relief area 622 is rectangular 625 with the long axis of the rectangle extending along the longitudinal axis of the top member 620. The rectangular relief area 625 is configured to mate with a correspondingly shaped load head 634. The combination of the rectangular shaped load head 634 and the rectangular relief area 625 allows the user to angle or tilt the superior member 620 relative to the base member 610 by extending the at least two expansion assemblies 630 to different lengths. The flush load head 624 functions to keep the threaded rod 632 inserted into the distal channel 638 of the flush load head 624 from rotating when the spiral gear 631 is turned. The flush load head 624 is aligned with the other hole 611 in the base member 610.

Shown in FIGS. 48-51 and 53-54, the top or superior member 620 may also include four extension struts 626 that extend below the long side walls of the member 620. The struts 626 may have two slots 627 on either side that separate the struts 626 from the side wall construct. Positioned at the inferior end of the strut is a locking tab 628 that engages with a corresponding locking notch 613 (see FIG. 52) that is positioned along the top edge of the long wall of the base member 610. In addition, a nesting seat 614 is aligned directly opposite the locking notch 613 at the inferior edge of the long side wall.

An alternative expansion mechanism 640 is shown in FIG. 52 comprises at least two expansion assemblies 629, 630 and a connector drive rod 641 that spans the gap between the two threaded rods 632 of the two expansion assemblies 629, 630. As explained more below, the expansion assembly 629 is comprised of a spiral gear 631, a threaded rod 632, and multiple support means 633. The expansion assembly 630 is comprised of a spiral gear 631, a threaded rod 632, a load head 634 and multiple support means 633. The expansion mechanism 640 functions to convert rotation movement of the spiral gear 631 into linear or translational movement of the load head 634 and the flush load head 624, each positioned at the superior end of the threaded rods 632. The connector drive rod 641 along with the two worm gears 645 functions to mirror the rotation movement of a tool 900, described in greater detail below, and translates this to either the first or second spiral gears 631, or alternatively, both at the same time. Rotation of the spiral gears 631 will result in a travel distance of the threaded rods 632 when the expansion mechanism 640 is actuated by an expansion tool, for example, tool 900.

Figure 56:
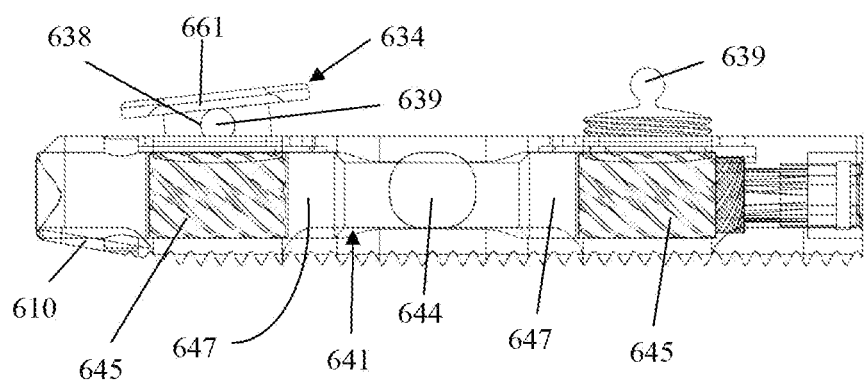
FIG. 56 is a side sectional view of the expandable interbody fusion device of FIG. 48, showing one of the two expansion assemblies tilted to accommodate the slanted top member (not shown) and the adjustment tool engaged with the expansion mechanism, in accordance with an aspect of the present invention.

As seen in FIG. 56, the connector drive rod 641 may be comprised of a hollow cylindrical shaft 644 and two connector sleeves 647 at the ends of the hollow cylindrical shaft 644. The connector sleeves 647 may have a larger diameter than the hollow cylindrical shaft 644 creating an hour glass shape to maximize the space inside the central opening 612. The hollow cylindrical shaft 644 may have an opening at one end 643 through one of the connector sleeves 647 for coupling with the tool 900. The hollow cylindrical shaft 644 may also have a drive shaft 648 at the end opposite the opening to secure a worm gear 645 to the drive rod 641. The two worm gears 645 may be positioned at either end of the connector drive rod 641. The worm gears 645 are configured to engage with the two spiral gears 631 of the expansion assemblies 629, 630.

FIG. 56 shows the assembled implant 600 with the connector drive rod 641 eccentrically positioned and extending through the length of the base member 610. The connector rod 641 is held in a manner that will allow it to be freely rotated and can either be left coupled to the base member 610 or be detachably coupled thereto.

As discussed above and illustrated in FIG. 52, the expansion assemblies 629, 630 include support means 633 which may be, for example, in the form of a ring or washer. The threaded rods 632 may include a pivot cylinder 639 located on the top or superior end of the rod 632. The load head 634 may include a distal channel 638. The outer configuration of the superior head surface of the expansion assembly 630 may be rectangular shaped to match with the corresponding relief 622 on the undersurface 621 of the top member 620. The threaded rod 632 has external threads 635 extending along its length. The external threads 635 are configured to match the internal threads 636 of the spiral gear 631. Spiral gear 631 is circular in shape and includes external spiral teeth 662 on its outer surface for the entire circumference. The teeth 662 of the spiral gear 631 are configured to allow for mating with the teeth 637 of the worm gear 645 positioned on the end of the connector drive rod 641. As described above, the expansion assemblies 629, 630 act to convert rotational movement of the spiral gears 631 into translational movement of the threaded rod 632. This is achieved by allowing free rotational movement of the spiral gear 631 while restricting the rotation of the threaded rods 632. By restricting the rotation of the threaded rod 632, the rod translates in either an upward or downward direction relative to the spiral gear 631 depending upon whether the threads (external and internal) 635, 636 are oriented either in a right-handed or left-handed direction. As discussed above, when the threaded rod 632 moves, the load head 634 contacts the relief of the undersurface 621 of the top member 620 to either move it away from or towards the base member 610. In other words, the height of the implant 600 either increases or decreases or the bone contacting surfaces 605 will be angled relative to each other depending upon the rotational direction of the tool 900 and also whether individual or both expansion assemblies 629, 630 are engaged.

With continued reference to FIG. 52, the support means 633 is used adjacent to the threaded rod 632 and the spiral gear 631. The support means 633 may be a snap ring or other similar type of structure that will secure the expansion assemblies 629, 630 to the base member 610 and the top member 620. The support means 633 also may act as a bearing surface to facilitate the rotation of the expansion assemblies 629, 630 when actuated.

As illustrated in FIG. 54, the expansion assembly 629 includes a pivot cylinder 639 inserted into the distal channel 638 of the flush load head 624. The expansion assembly 630 includes a pivot cylinder 639 inserted into the distal channel 638 of the load head 634. These constructs allow the flush load head 624 and load head 634 to pivot or slide around the outer diameter of the cylinder 639 when the threaded rods 632 are extended to two different lengths causing the top member 620 to tilt or slant. FIG. 56 shows how the load head 634 is capable of tilting or canting. The rectangular top surface or top portion 661 is configured to slide along the relief 625 of the undersurface 621 to allow for uneven lengthening of the expansion assemblies 629, 630 to create the angled relationship of the superior member 620 relative to the base member 610. The rectangular relief 625 in the undersurface 621 and the rectangular shaped load head 634 facilitates the angulation process and the load transfer between the superior member 620 and the base member 610 while avoiding potential binding of the expansion assembly 630 during the expansion and retraction process. Likewise, the flush load head 624, which is coupled to the undersurface 621 of the superior member 620, tilts or cants as superior member 620 tilts or cants relative to the base member 610.

Referring now to FIGS. 57-60, is another example of a unilateral, vertical expandable interbody fusion device 700. The device 700 as seen in FIG. 57, includes the at least one moveable top or superior member 620 and a base or bottom member 610 as described above with reference to device 600 in FIGS. 48-56 which will not be described again here for brevity sake.

As shown in FIG. 57, the superior and inferior bone contacting surfaces 604 may be generally parallel to each other. However, the expansion mechanism 740 (see FIG. 58) will allow the user to angle the bone contacting surface 604 of the base member 610 as seen in FIG. 57, wherein the near end is fully expanded and the far end is partially expanded. In addition, the expansion mechanism 740 allows for the far end to be expanded while the near end is retracted or only partially expanded.

FIG. 57 shows the expansion tool opening 680 off-center from the longitudinal axis of the implant 700. The off-center orientation is achieved by configuration of the expansion mechanism 740 that will be described in more detail below. The off-center expansion tool opening 680 and the corresponding elimination of the expansion mechanism 740 along the center longitudinal axis of the implant 700 provides the surgeon with the ability to pack a maximum amount of bone graft material through the opening 612 and create a continuous graft from the inferior vertebral body to the superior vertebral body because the opening 612 is unobstructed by any tool or actuation shaft and extends entirely through the implant 700. The implant 700 may also include a locking opening 670 relatively parallel to the tool opening 680 on the end of the base member 610.

Figure 58:
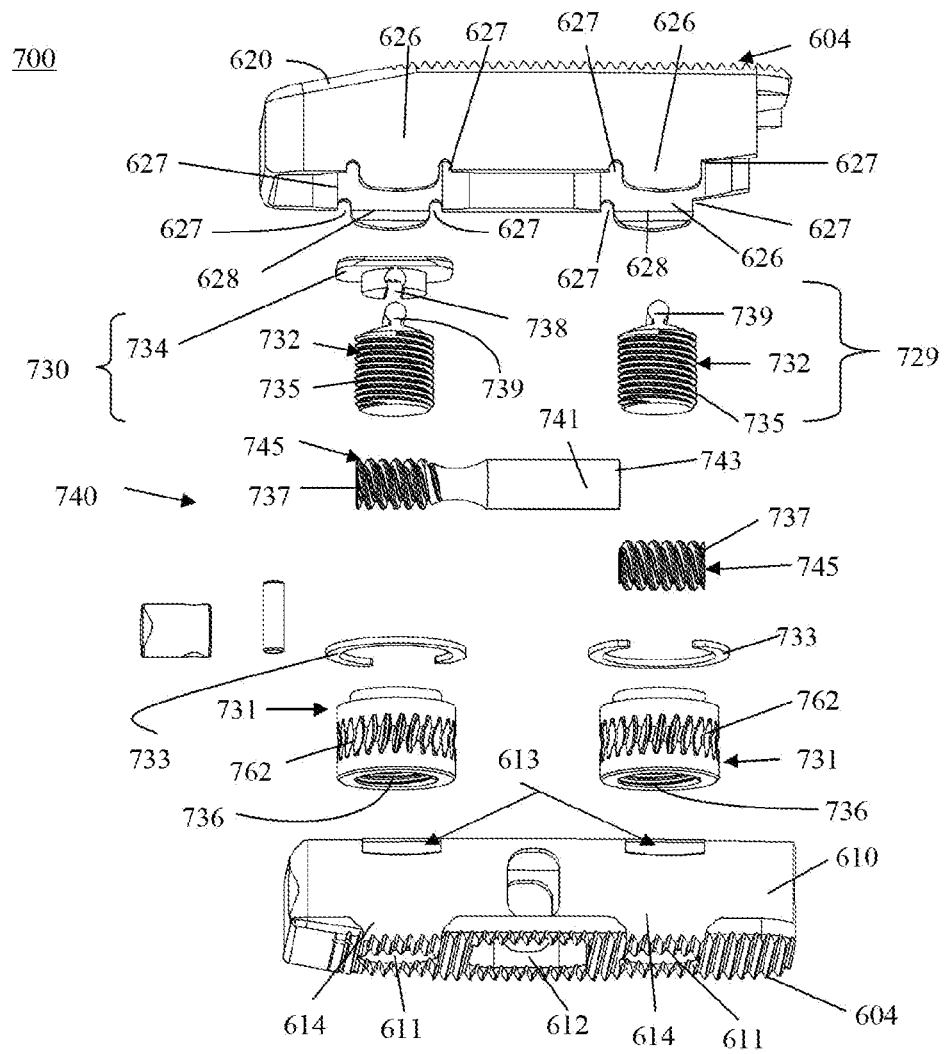
FIG. 58 is an exploded view of the expandable interbody fusion device of FIG. 57, in accordance with an aspect of the present invention.

FIG. 58 shows an exploded view of all of the components that comprise the implant 700. Specifically, shown in the exploded view of FIG. 58 are the support means 733, that are adjacent the vertical cylinder or cylindrical gear 731 (these names may be used interchangeably) which includes circumferential serial depressions 762. The cylindrical gear 731 is configured to maximize strength and improve trackability by having the circumferential serial depressions 762 only positioned around the central portion of the cylinder 731. The circumferential serial depressions 762 may include uniquely oriented thread patterns. The cylinder gear 731 may sit on the internal circumferential shoulder 613 that functions to maintain the expansion assembly 730 in a vertical orientation relative to the base member 610 and aligned with holes 611. The shoulder 613 (see FIG. 19 with 213) also may operate as a bearing surface against which the support means 733 contacts. Also shown in FIGS. 57 and 58 are peripherally positioned holes 611 which are configured to house a portion of the two expansion assemblies 729, 730.

Figure 59:
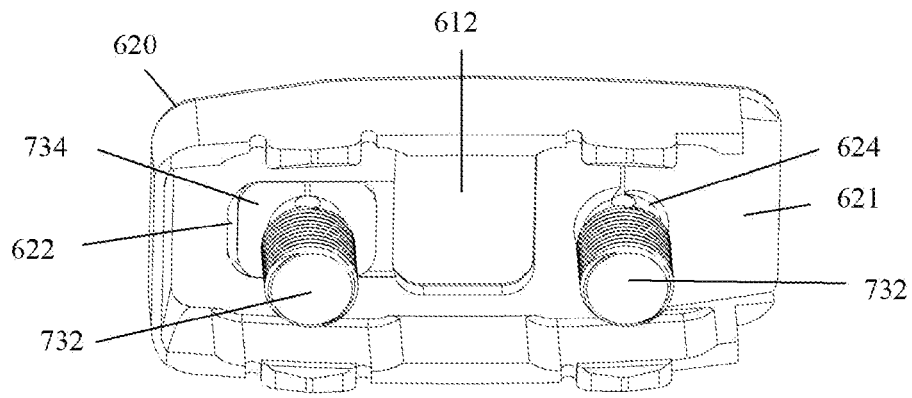
FIG. 59 is an inferior perspective view of the expandable interbody fusion device of FIG. 57, showing the two expansion assemblies seated within the top or moveable member, in accordance with an aspect of the present invention.

FIGS. 53 and 59 shows inferior views of the undersurface 621 of the superior moveable member 620, as described above and for brevity sake will not be described again. FIG. 59 shows the load head 734 positioned within the relief area 622 of the superior member 620 and a threaded rod 732 inserted into the flush load head 624 protruding from the undersurface 621 of the superior member 620.

As seen in FIG. 53, the relief area 622 is as described above with reference to the base member 610. The rectangular relief area 625 of device 700 is configured to mate with a correspondingly shaped load head 734. The combination of the rectangular shaped load head 734 and the rectangular relief area 625 allows the user to angle or tilt the superior member 620 relative to the base member 610 by extending the at least two expansion assemblies 729, 730 to different lengths. The flush load head 624 functions to keep the threaded rod 732 inserted into the distal channel 638 of the flush load head 624 from rotating when the gear 731 is turned. The flush load head 624 is aligned with the other hole 611 in the base member 610.

An alternative expansion mechanism 740 is shown in FIG. 58 comprises at least two expansion assemblies 729, 730 and a connector drive rod 741 that spans the gap between the two threaded rods 732 of the two expansion assemblies 729, 730. As explained more below, the expansion assembly 729 is comprised of a gear 731, a threaded rod 732, and multiple support means 733. The expansion assembly 730 is comprised of a gear 731, a threaded rod 732, a load head 734 and multiple support means 733. The expansion mechanism 740 functions to convert rotation movement of the gear 731 into linear or translational movement of the load head 734 and the flush load head 624, each positioned at the superior end of the threaded rods 732. The connector drive rod 741 including a worm gear 745 and the detached worm gear 745 function to mirror the rotational movement of a tool 900, described in greater detail below, and translate this to either the first or second gears 731, or alternatively, both at the same time. Rotation of the gears 731 will result in a travel distance of the threaded rods 732 when the expansion mechanism 740 is actuated by the expansion tool 900. As a worm gear 745 is coupled to the connector drive rod 741 the coupled worm gear 745 will rotate as the drive rod 741 is rotated, thus avoiding the need for the tool 900 to pass through the entire length of the drive rod 741 to engage the worm gear 745 on the far end of the implant 700.

Figure 60:
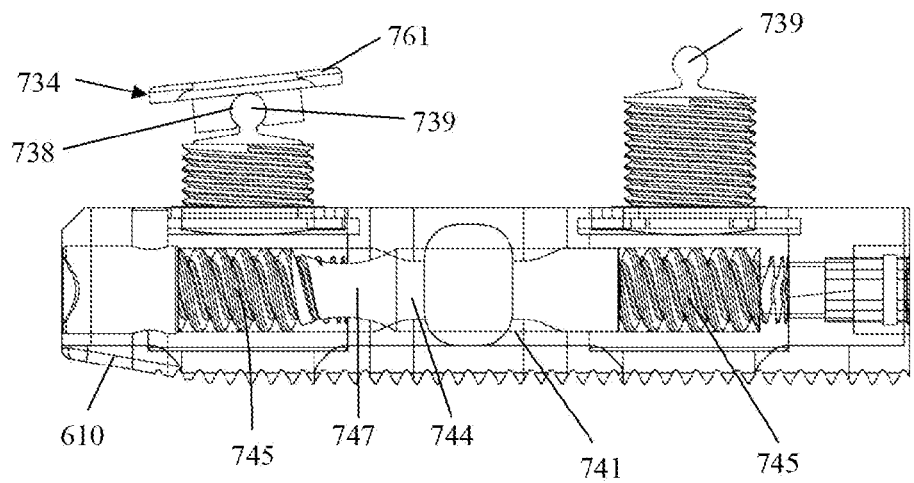
FIG. 60 is a side elevational transparent view of the expandable interbody fusion device of FIG. 57, showing one expansion assembly tilted to accommodate the slanted top member (not shown), in accordance with an aspect of the present invention.

As seen in FIG. 60, the connector drive rod 741 may be comprised of a hollow cylindrical shaft 744 and a connector sleeve 747 coupled to a worm gear 745 at one end of the hollow cylindrical shaft 744. The connector sleeves 747 may have a smaller diameter than the hollow cylindrical shaft 744. The hollow cylindrical shaft 744 may have an opening at one end 743 for coupling with the tool 900. A second worm gear 745 may be positioned at the end opposite the worm gear 745 coupled to the connector drive rod 741. The worm gear 745 is configured to engage with the gear 731 of the expansion assembly 729. The coupled worm gear teeth 745 on the far end of the connector drive rod 741 are configured to engage with the gear 731 of the expansion assembly 730.

FIG. 60 shows the assembled implant 700 with the connector drive rod 741 eccentrically positioned and extending through length of the base member 610. The connector rod 741 is held in a manner that will allow it to be freely rotated and can either be left coupled to the base member 610 or be detachably coupled thereto.

As discussed above and illustrated in FIG. 58, the expansion assemblies 729, 730 include support means 733 which may be, for example, in the form of a ring or washer. The threaded rods 732 may include a pivot cylinder 739 located on the top or superior end of the rod 732. The load head 734 may include a distal channel 738. The outer configuration of the superior head surface of the expansion assembly 730 may be rectangular shaped to match with the corresponding relief 622 on the undersurface 621 of the top member 620. The threaded rod 732 has external threads 735 extending along its length. The external threads 735 are configured to match the internal threads 736 of the gear 731. The gear 731 is cylindrical in shape and includes external substantially vertical depressions on the middle aspect of its outer surface which extend around the entire circumference. The proximal and distal ends of the gears 731 may have a smooth surface, above and below the substantially vertical depression. The substantially vertical depression or circumferential serial depressions 762 of the gear 731 are configured to allow for mating with the teeth 737 of the worm gear 745 positioned on the ends of the connector drive rod 741. As described above, the expansion assemblies 729, 730 act to convert rotational movement of the gears 731 into translational movement of the threaded rod 732. This is achieved by allowing free rotational movement of the gear 731 while restricting the rotation of the threaded rods 732. By restricting the rotation of the threaded rod 732, the rod translates in either an upward or downward direction relative to the gear 731 depending upon whether the threads (external and internal) 735, 736 are oriented in a right-handed or left-handed direction. As discussed above, when the threaded rod 732 moves, the load head 734 contacts the relief of the undersurface 621 of the top member 620 to either move it away from or towards the base member 610. In other words, the height of the implant 700 either increases or decreases or the bone contacting surfaces 605 will be angled relative to each other depending upon the rotational direction of the tool 900 and also whether individual or both expansion assemblies 729, 730 are engaged.

With continued reference to FIG. 58, the support means 733 is used adjacent to the threaded rod 732 and the gear 731. The support means 733 may be, for example, a snap ring or other similar type of structure that will secure the expansion assemblies 729, 730 to the base member 610 and the top member 620. The support means 733 also may act as a bearing surface to facilitate the rotation of the expansion assemblies 729, 730 when actuated.

As illustrated in FIG. 59, the expansion assembly 729 includes a pivot cylinder 739 inserted into the distal channel 638 of the flush load head 624. The expansion assembly 730 includes a pivot cylinder 739 inserted into the distal channel 738 of the load head 734. These constructs allow the flush load head 624 and load head 734 to pivot or slide around the outer diameter of the cylinder 739 when the threaded rods 732 are extended to two different lengths causing the top member 620 to tilt or slant. FIG. 60 shows how the load head 734 is capable of tilting or canting. The rectangular top surface or top portion 761 is configured to slide along the relief 625 of the undersurface 621 to allow for uneven lengthening of the expansion assemblies 729, 730 to create the angled relationship of the superior member 620 relative to the base member 610. The rectangular relief 725 in the undersurface 621 and the rectangular shaped load head 734 facilitates the angulation process and the load transfer between the superior member 620 and the base member 610 while avoiding potential binding of the expansion assembly 730 during the expansion and refraction process. Likewise, the flush load head 624, which is coupled to the undersurface 621 of the superior member 620, tilts or cants as superior member 620 tilts or cants relative to the base member 610.

FIGS. 61-63B, show another example of a unilateral, vertical expandable interbody fusion device 800. The device 800 as seen in FIG. 61, includes the at least one moveable top or superior member 620 and a base or bottom member 610, as described above with reference to device 600 and for brevity sake will not be described again.

As shown in FIG. 61, the superior and inferior bone contacting surfaces 604 may be generally parallel to each other. However, the expansion mechanism 840 (see FIG. 62) will allow the user to angle the bone contacting surface 604 of the base member 610 as seen in FIG. 61, wherein the near end is expanded and the far end is retracted. In addition, the expansion mechanism 840 allows for the far end to be expanded while the near end is retracted.

FIG. 61 shows the expansion tool opening 680 off-center from the longitudinal axis of the implant 800. The off-center orientation is achieved by configuration of the expansion mechanism 840 that will be described in more detail below. The off-center expansion tool opening 680 and the corresponding elimination of the expansion mechanism 840 along the center longitudinal axis of the implant 800 provides the surgeon with the ability to pack a maximum amount of bone graft material through the opening 612 and create a continuous graft from the inferior vertebral body to the superior vertebral body because the opening 612 is unobstructed by any tool or actuation shaft and extends entirely through the implant 800. The implant 800 may also include a locking opening 670 relatively parallel to the tool opening 680 on the end of the base member 610 for securing the tool 900 to the implant 800.

Figure 62:
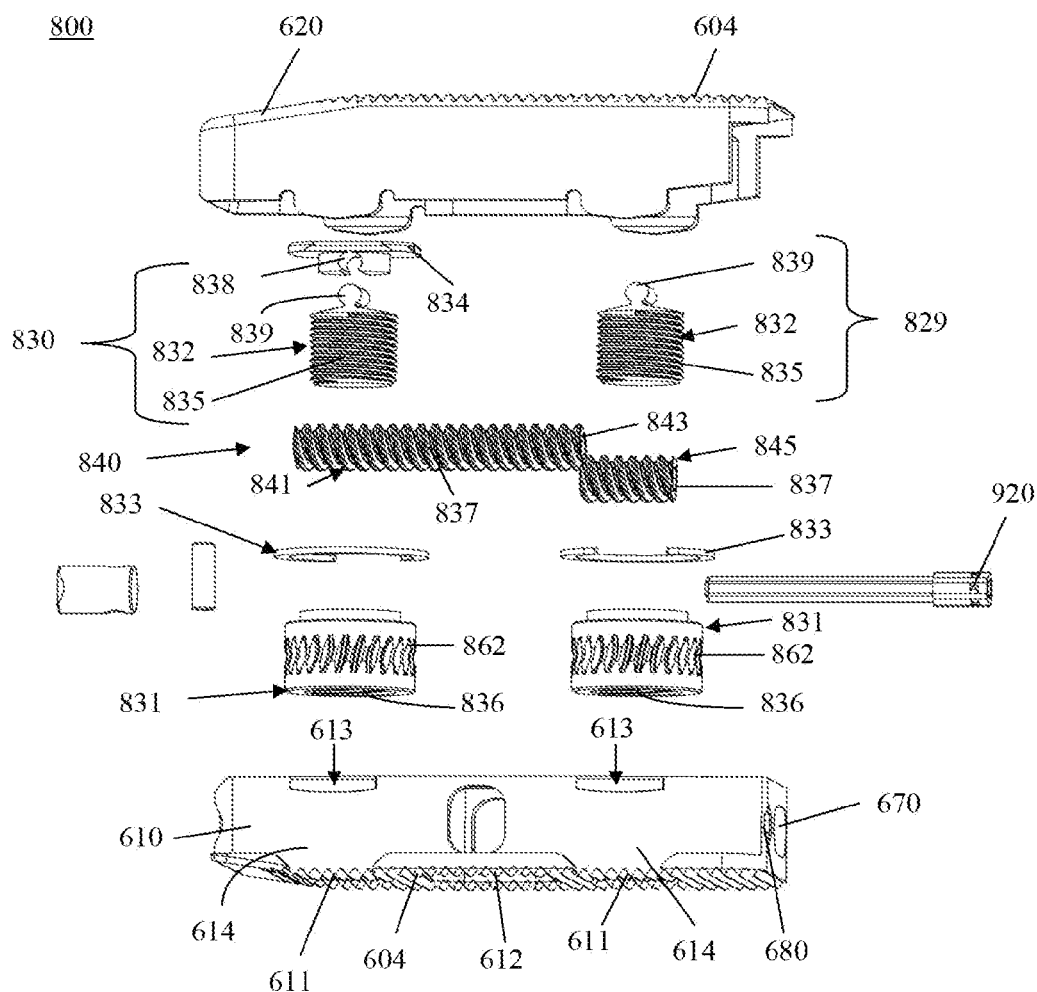
FIG. 62 is an exploded view of the expandable interbody fusion device of FIG. 61, in accordance with an aspect of the present invention.

FIG. 62 shows an exploded view of all of the components that comprise the implant 800. Specifically, shown in the exploded view of FIG. 62 are the support means 833, that are adjacent the gear ring 831 and may sit on the internal circumferential shoulder 613 that functions to maintain the expansion assembly 830 in a vertical orientation relative to the base member 610 and aligned with holes 611. The shoulder 613 (see FIG. 19 with 213) also may operate as a bearing surface against which the support means 833 contacts. Also seen in FIGS. 61-62 are peripherally positioned holes 611 which are configured to house a portion of the two expansion assemblies 829, 830.

Figure 63A:
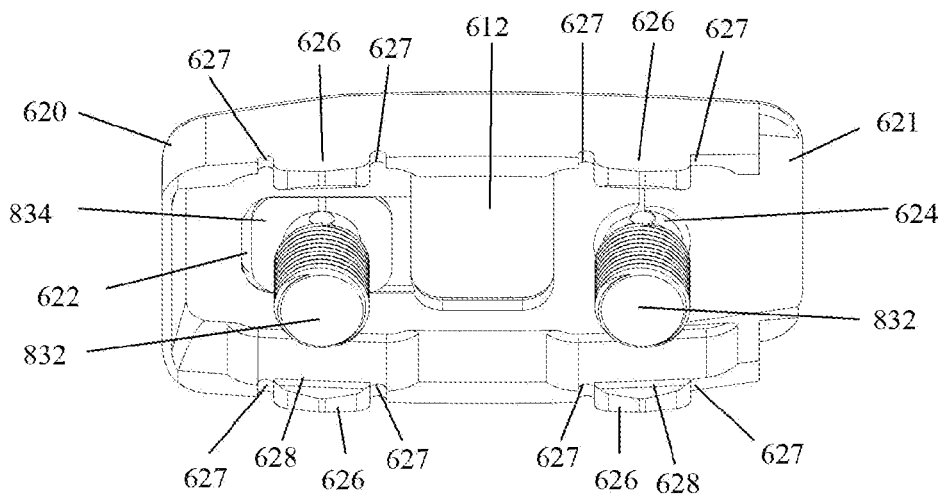
FIG. 63A is an inferior perspective view of the expandable interbody fusion device of FIG. 61, showing the two expansion assemblies seated within the top or moveable member, in accordance with an aspect of the present invention.

FIGS. 53 and 63A are inferior views of the undersurface 621 of the superior moveable member 620. FIG. 63A shows the load head 834 positioned within the relief area 622 of the superior member 620 and a threaded rod 832 inserted into the flush load head 624 protruding from the undersurface 621 of the superior member 620.

As seen in FIG. 53, the relief area 622 is substantially planar and aligned with one of the holes 611 in the base member 610. The rectangular relief area 625 of the device 800 is configured to mate with a correspondingly shaped load head 834. The combination of the rectangular shaped load head 834 and the rectangular relief area 625 allows the user to angle or tilt the superior member 620 relative to the base member 610 by extending the at least two expansion assemblies 830 to different lengths. The flush load head 624 functions to keep the threaded rod 832 inserted into the distal channel 638 of the flush load head 624 from rotating when the cylindrical gear 831 is turned. The flush load head 624 is aligned with the other hole 611 in the base member 610.

An alternative expansion mechanism 840 is shown in FIG. 62 comprises at least two expansion assemblies 829, 830 and a connector drive rod 841 that spans the gap between the two threaded rods 832 of the two expansion assemblies 829, 830. The connector drive rod 841 and worm gear 845 may for example include a pressure angle stub involute tooth ranging from about 10 to 45 degrees, a diametral pitch of about 40 to 90, a worm lead angle of about 10 to 45 degrees, and about 12 to 40 teeth. In addition, the worm gear 845 may for example have approximately 1 to 10 lead threads.

As explained more below, the expansion assembly 829 is comprised of a gear 831, a threaded rod 832, and multiple support means 833. The expansion assembly 830 is comprised of a gear 831, a threaded rod 832, a load head 834 and multiple support means 833. The expansion mechanism 840 functions to convert rotation movement of the gear 831 into linear or translational movement of the load head 834 and the flush load head 624, each positioned at the superior end of the threaded rods 832. The connector drive rod 841 includes the teeth 837 of a worm gear and in conjunction with a worm gear 845 functions to mirror the rotation movement of a tool 900, described in greater detail below, and translate this to either the first or second gears 831, or alternatively, both at the same time. Rotation of the gears 831 will result in a travel distance of the threaded rods 832 when the expansion mechanism 840 is actuated by the expansion tool 900. As the connector drive rod 841 includes the teeth 837 of a worm gear 845 along its entire length, the rotation of the drive rod 841 rotates the far gear 831, thus avoiding the need for the tool 900 to pass through the entire length of the drive rod 841 to engage a worm gear 845 on the far end of the implant 800.

Figure 63B:
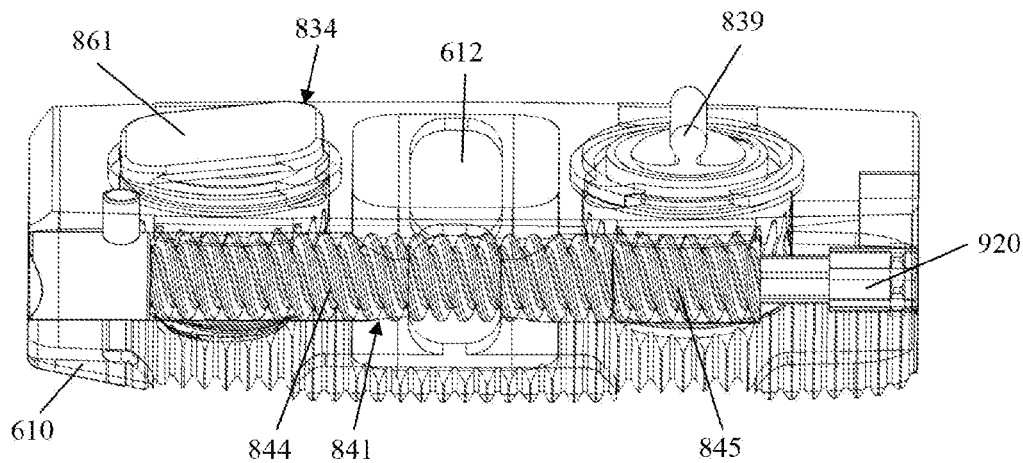
FIG. 63B is a side elevational transparent view of the expandable interbody fusion device of FIG. 61, showing one expansion assembly tilted to accommodate the slanted top member (not shown), in accordance with an aspect of the present invention.

As seen in FIG. 63B, the connector drive rod 841 may be comprised of a cylindrical shaft 844 including worm gear teeth 837. The cylindrical shaft 844 may have an opening at one end 843 for coupling with the tool 900. The worm gear 845 may be positioned at the near end of the connector drive rod 841. The worm gear 845 is configured to engage with the gear 831 of the expansion assembly 829. The worm gear teeth 837 on the far end of the connector drive rod 841 are configured to engage with the gear 831 of the expansion assembly 830.

FIG. 63B shows the assembled implant 800 with the connector drive rod 841 eccentrically positioned and extending through length of the base member 610. The connector rod 841 is held in a manner that will allow it to be freely rotated and can either be left coupled to the base member 610 or be detachably coupled thereto.

As discussed above and illustrated in FIG. 62, the expansion assemblies 829, 830 include support means 833 which may be, for example, in the form of a ring or washer. The threaded rods 832 may include a pivot cylinder 839 located on the top or superior end of the rod. The load head 834 may include a distal channel 838. The outer configuration of the superior head surface of the expansion assembly 830 may be rectangular shaped to match with the corresponding relief 622 on the undersurface 621 of the top member 620. The threaded rod 832 has external threads 835 extending along its length. The external threads 835 are configured to match the internal threads 836 of the gear 831. Gear 831 is circular in shape and includes external substantially vertical depressions on its outer surface for the entire circumference. The circumferential serial depressions 862 of the gear 831 are configured to allow for mating with the teeth 837 of the worm gear 845 positioned on the end of the connector drive rod 841. As described above, the expansion assemblies 829, 830 act to convert rotational movement of the gears 831 into translational movement of the threaded rod 832. This is achieved by allowing free rotational movement of the gear 831 while restricting the rotation of the threaded rods 832. By restricting the rotation of the threaded rod 832, the rod translates in either an upward or downward direction relative to the gear 831 depending upon whether the threads (external and internal) 835, 836 are oriented either in a right-handed or left-handed direction. The threads 835, 836 may have a variety of different thread sizes and pitches. In addition, the threads 835, 836 may include single, double, or triple lead threads. As discussed above, when the threaded rod 832 moves, the load head 834 contacts the relief of the undersurface 621 of the top member 620 to either move it away from or towards the base member 610. In other words, the height of the implant 800 either increases or decreases or the bone contacting surfaces 605 will be angled relative to each other depending upon the rotational direction of the tool 900 and also whether individual or both expansion assemblies 829, 830 are engaged.

With continued reference to FIG. 62, the support means 833 are used adjacent to the threaded rod 832 and the gear 831. The support means 833 may be, for example, a snap ring or other similar type of structure that will secure the expansion assemblies 829, 830 to the base member 610 and the top member 620. The support means 833 also may act as a bearing surface to facilitate the rotation of the expansion assemblies 829, 830 when actuated.

As illustrated in FIG. 63A, the expansion assembly 829 includes a pivot cylinder 639 inserted into the distal channel 638 of the flush load head 624. The expansion assembly 830 includes a pivot cylinder 839 inserted into the distal channel 838 of the load head 834. These constructs allow the flush load head 624 and load head 834 to pivot or slide around the outer diameter of the cylinder 839 when the threaded rods 832 are extended to two different lengths causing the top member 620 to tilt or slant. FIG. 63B shows how the load head 834 is capable of tilting or canting. The rectangular top surface or top portion 861 is configured to slide along the relief 625 of the undersurface 621 to allow for uneven lengthening of the expansion assemblies 829, 830 to create the angled relationship of the superior member 620 relative to the base member 610. The rectangular relief 625 in the undersurface 621 and the rectangular shaped load head 834 facilitates the angulation process and the load transfer between the superior member 620 and the base member 610 while avoiding potential binding of the expansion assembly 830 during the expansion and retraction process. Likewise, the flush load head 624, which is coupled to the undersurface 621 of the superior member 620, tilts or cants as superior member 620 tilts or cants relative to the base member 610.

Figure 64A:
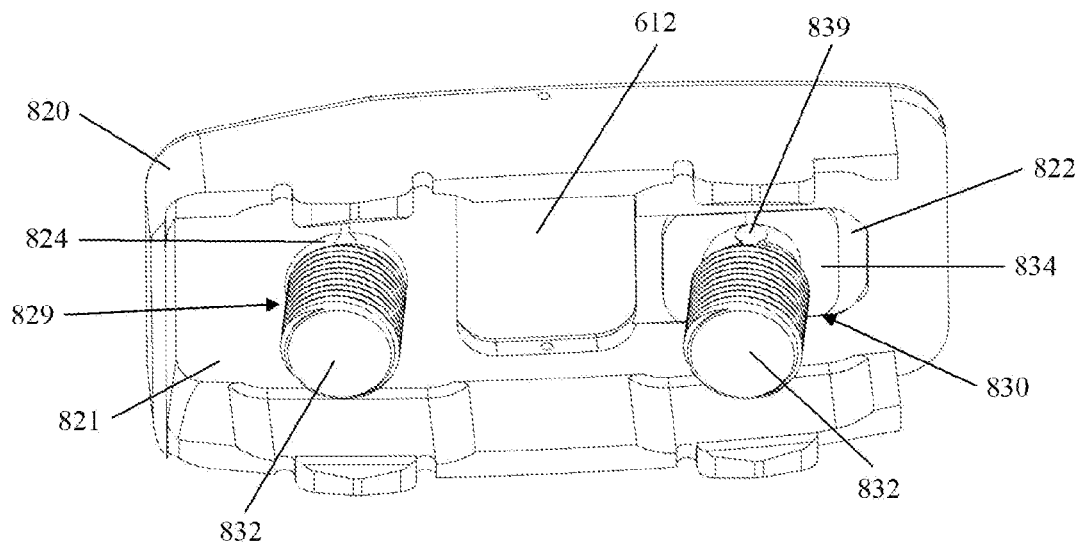
FIG. 64A is an inferior perspective view of the expandable interbody fusion device of FIG. 61 with an alternative expansion mechanism and top or moveable member, showing the two expansion assemblies seated within the top member, in accordance with an aspect of the present invention.
Figure 64B:
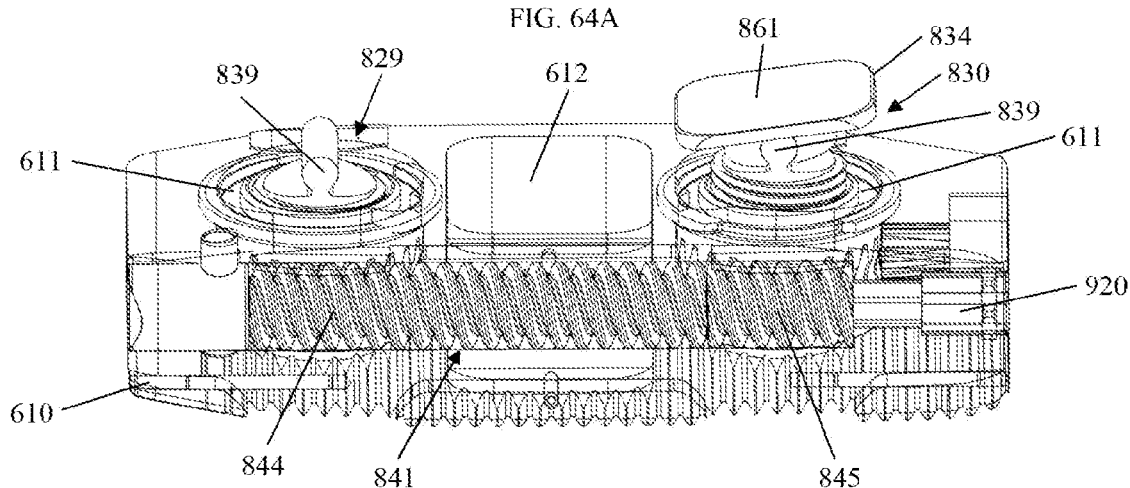
FIG. 64B is a side elevational transparent view of the expandable interbody fusion device of FIG. 64A, showing one expansion assembly tilted to accommodate the slanted top member (not shown), in accordance with an aspect of the present invention.

As shown in FIGS. 64A and 64B, the implant 800 may include an alternative superior moveable member 820 with the two expansion assemblies 829, 830 inserted into opposite holes 611 in the base member 610 than as shown above with reference to FIGS. 61-63B. The superior member 820 is similar to superior member 620 and includes a central opening 612 and the bone contacting surface 604, as described above, however the relief area 822 and flush load head 824 of the superior member 820 are positioned on opposite sides of the central opening 612 on the undersurface 821 than on the superior member 620. The relief area 822 is adjacent to the central opening 612. The flush load head 824 protrudes from the undersurface 821 of the superior member 820 and is adjacent the central opening 612 and opposite the relief area 822. As shown in FIG. 64A, the flush load head 824 is on the proximal side of the central opening 612 and the relief area 822 is on the distal side of the central opening 612. FIG. 64A shows the load head 834 positioned within the relief area 822 of the superior member 820 and a threaded rod 832 inserted into the flush load head 824 protruding from the undersurface 821 of the superior member 820.

Figure 65:
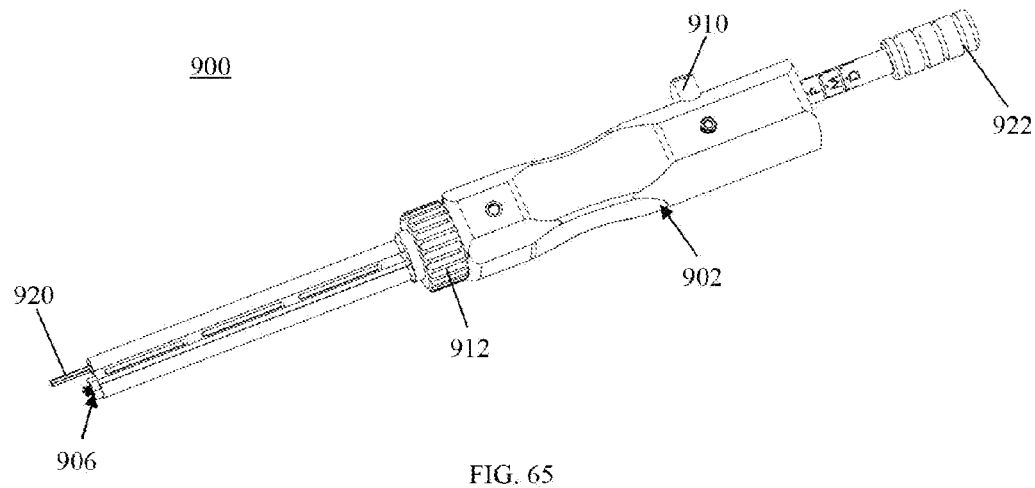
FIG. 65 is a bottom perspective view of an expansion tool in a first position, in accordance with an aspect of the present invention.
Figure 66:
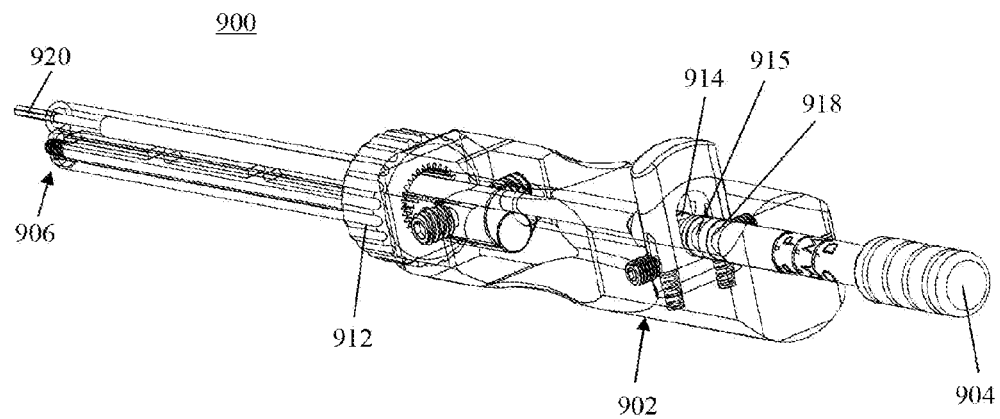
FIG. 66 is a rear perspective view of the expansion tool of FIG. 65 with a transparent outer housing of the handle, in accordance with an aspect of the present invention.

FIGS. 65-66 show another embodiment expansion tool 900, designed to engage the far expansion assembly, the near expansion assembly, and both expansion assemblies simultaneously. The end of the expansion tool 900 may be configured, for example, as a hex head or other like configuration that will allow for the user to rotate the expansion tool 900 and cause expansion mechanisms, for example, the expansion mechanisms 640, 740, 840, to rotate.

As noted above, the tool 900 may be configured in various forms, depending upon the number of expansion assemblies 629 and 630, 729 and 730, 829 and 830 that are used in the expansion mechanisms 640, 740, 840. The tool 900 may consist of a handle 902, a shaft 904 that extends to a connector end 908, and a locking mechanism 906. The connector end 908 may engage the expansion assemblies. The tool 900 may be inserted into an implant, such as, implants 600, 700, or 800, by inserting the locking mechanism 906 of the tool 900 into an expansion tool opening 680 and the connector end 908 of the tool 900 into a locking opening 670. Once the tool 900 is inserted into the locking opening 670 of the implant 600, 700, 800, respectively, the knob 912 may be turned to secure the locking mechanism 906 in the locking opening 670. Once the locking mechanism 906 secures the tool 900 to the implant 600, 700, 800, the connector end 908 may be extended to engage the expansion assemblies. The connector end 908 of the tool 900 may be extendable to engage the far expansion assembly using the connector drive rod 641, 741, 841.

As shown in FIG. 65, the shaft 904 includes a first position P which corresponds to a first position for the connector end 908, in the first position P the connector end 908 engages the near expansion assembly to expand the implants 600, 700, and 800 as illustrated in FIGS. 48, 57, 61. As also shown in FIG. 65, the shaft 904 includes a second position M which corresponds to a second position for the connector end 908 (not shown), in the second position M the connector end 908 engages both expansion assemblies simultaneously to expand the implants 600, 700, 800 as illustrated in FIGS. 50 and 51. Also shown in FIG. 65, the shaft 904 includes a third position D which corresponds to a third position for the connector end 908 (not shown), in the third position D the connector end 908 engages the far expansion assembly to expand only the far end of the implants 600, 700, 800. An actuation button 910 may be depressed to move the shaft 904 between the first, second and third positions of the connector end 908. The actuation button 910 may be spring loaded to engage grooves 914, 916, 918 in the shaft 904. When the groove 914 is engaged the connector end 908 is in the first position. When the groove 916 is engaged the connector end 908 is in the second position. When the groove 918 is engaged the connector end 908 is in the third position.

The connector end 908 may be configured as, for example, a hex male end, although a square or other multi-lobed configuration may be used. It is important to note that if the two expansion assemblies are not rotated simultaneously then the superior member 620 may be angled because of the resulting difference in length of the two expansion assemblies 629, 630, 729, 730, 829, 830. The cogs or teeth 637, 737, 837 of worm gears 645, 745, 845 on the ends of the connector drive rod 641, 741, 841 are sized to mate with the corresponding teeth 662 or serial depressions 762, 862 of the two gears 631, 731, 831 to facilitate rotation of the gear 631, 731, 831 when the tool 900 is turned.

Referring now to FIG. 66, once the desired expansion of the implant 600, 700, 800 is achieved a locking insert 920 is connected to an inserter tool 922 which is passed through the handle 902. The locking insert 920 is illustrated in FIG. 62. The locking insert 920 may be inserted into the expansion tool opening 680 to secure the implant 600, 700, 800 into the desired expansion and/or retraction. After the locking insert 920 is secured in the implant 600, 700, 800, the tool 900 may be removed from the implant 600, 700, 800 by turning knob 912 to release the locking mechanism 906 from the locking opening 670.

Figure 67:
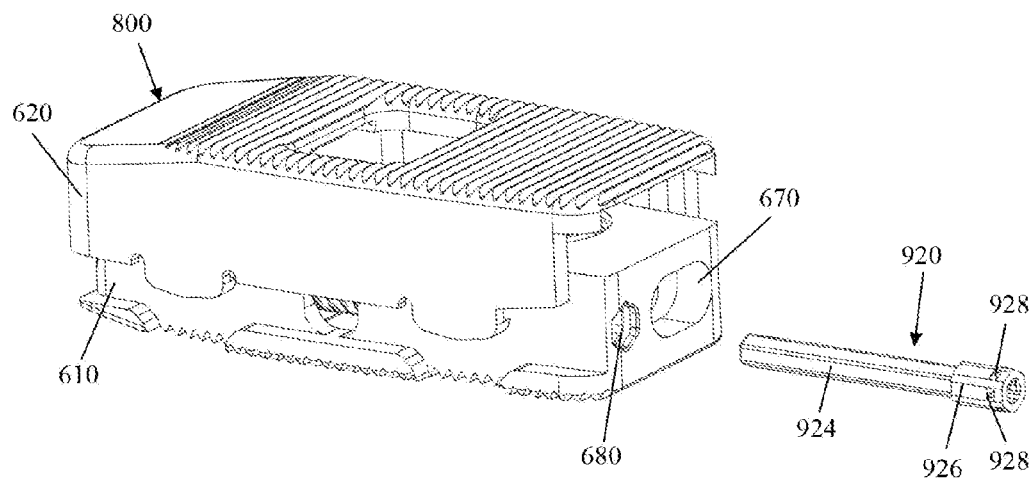
FIG. 67 is a lateral perspective view of an expandable interbody fusion device showing both ends in an extended or expanded position and the locking insert prior to insertion, in accordance with an aspect of the present invention.

For example purposes, the implant 800 and locking insert 920 are illustrated in FIG. 67. It should be noted that the locking insert 920 may also be used with the implant embodiments 600,700 as well as other implants. The locking insert 920 may include a shaft 924 and a head 926. The locking insert 920 may be inserted into the expansion tool opening 680 once the desired expansion and/or retraction of the implant 800 has been achieved. The head 926 will likely be countersunk into the tool opening 680 when fully inserted. The head 926 of the locking insert 920 may also include at least one protrusion 928 to secure the locking insert 920 to the implant 800. The locking insert 920 may be inserted into tool opening 680 and at least one protrusion 928 may be snapped into a channel in the tool opening 680 to secure the locking insert 920 in the implant 800.

Figure 71:
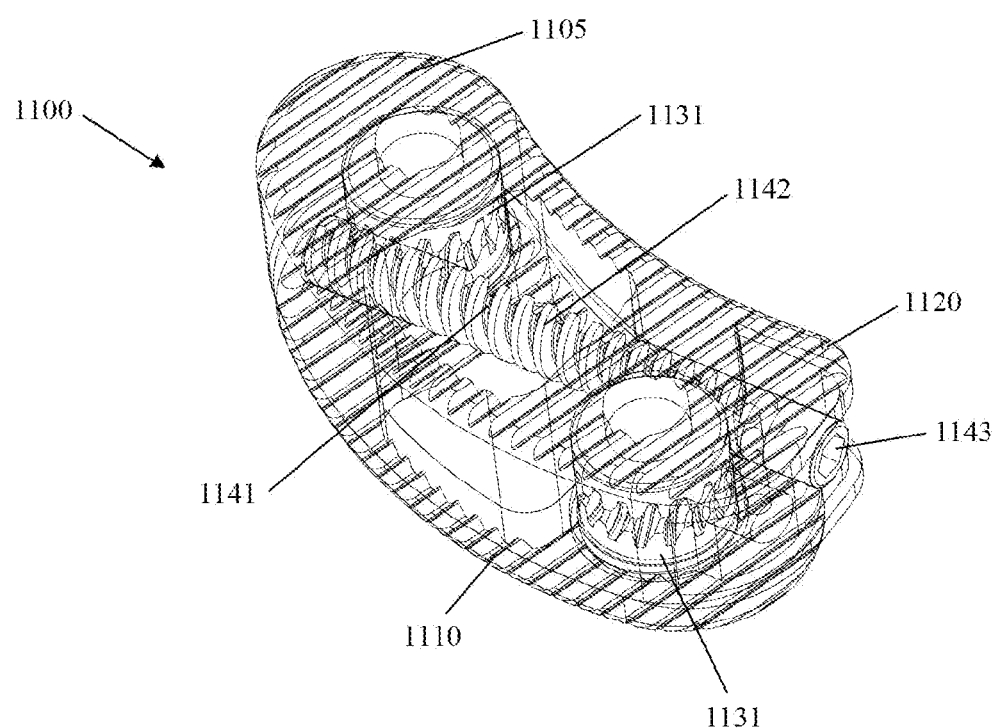
FIG. 71 is a superior, perspective, transparent view of the expandable interbody fusion device of FIG. 68, showing the dual expansion assemblies with the connecting drive rod positioned within the base member, in accordance with an aspect of the present invention.

As depicted in FIGS. 68 and 71, the general arrangement of a unilateral vertical expandable interbody fusion device 1100, in accordance with an aspect of the present invention, includes at least one moveable top member 1120 and a base member 1110. The top member 1120 may be detachably coupled to the base member 1110. The device 1100 as seen in FIG. 68, has a generally arcuate or banana shaped geometry to facilitate insertion and bone coverage. Although it would be understood by one skilled in the art that other outside configurations, shapes and angulations can be used. For example purposes, the long sides are slightly arcuate although it is contemplated that other geometrical shapes may also be used in the construct.

As seen in FIG. 68, at least one through hole 1111 for insertion of bone graft material is disposed on the inferior and superior bone contacting surfaces 1105. The hole 1111 extends through the external surfaces 1105 of the base member 1110 and top member 1120. The opening 1111 typically extends through both bone contacting surfaces 1105 and into the inner cavity of the device 1100. The size and configuration of the opening 1111 allows the surgeon to place bone graft material inside the implant 1100 to achieve a continuous fusion between the inferior and superior vertebral bodies.

Although not shown, typically the superior and inferior bone contacting surfaces 1105 are generally parallel to each other. FIG. 68 exhibits the bone contacting surfaces 1105 to have teeth-like or tine structures projecting away from the superior and inferior surfaces. One skilled in the art would recognize that other surface treatments may be applied to the bone contacting surfaces 1105 to enhance fixation with the opposing bone surface. Although not shown, it is understood by one skilled in the art that modular bone contacting surfaces, caps or plates may be used to provide for varying types of bone contacting surfaces and structures, including, but not limited to sharp tines, porous coatings, biomaterial/ingrowth surfaces and ridge structures. Further, it is contemplated that angled bone contacting surfaces, caps or plates may be attachable to the implant 1100 to address various deformities that are encountered clinically. It is also understood that the bone contacting surfaces 1105 may be coated with bioactive or bone ingrowth coatings.

Figure 69:
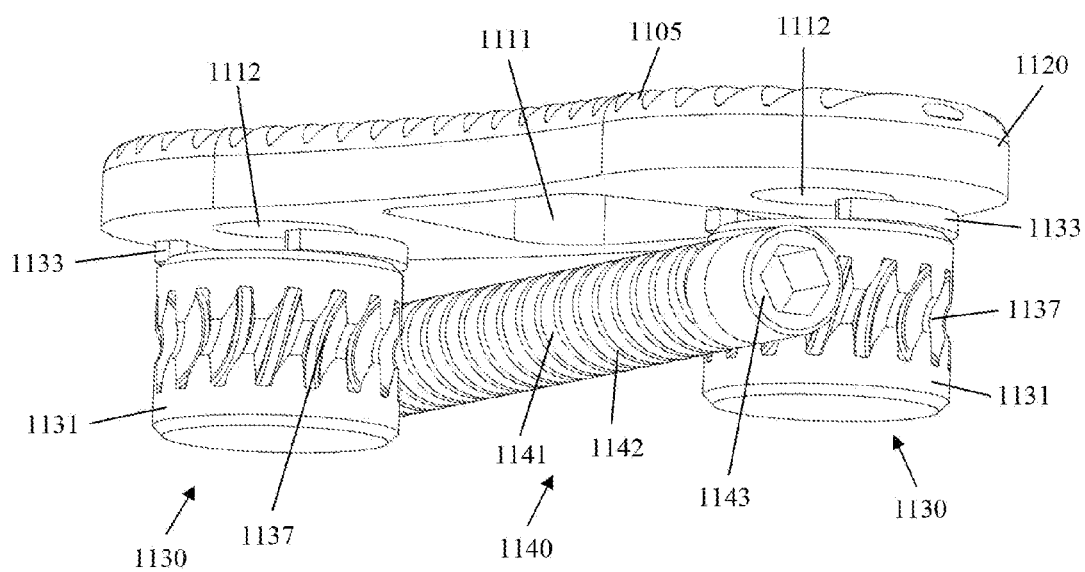
FIG. 69 is an inferior view of the expandable interbody fusion device of FIG. 68, with the base member removed and the dual expansion assemblies with the connecting drive rod in place, in accordance with an aspect of the present invention.

FIG. 69 is an inferior view of the top member 1120 with the base member 1110 removed to show the expansion mechanism 1140 with two expansion assemblies 1130 and the inserted connecting drive rod 1141. As shown, the connecting drive rod 1141 passes on one side of the gear member 1131 of one of the expansion assembly 1130 and then on the opposing side of a second gear member 1131 of the second expansion assembly 1130. The transverse positioning of the connecting drive rod 1141 facilitates contact between the worm gears 1142 of the connecting drive rod 1141 and the corresponding depressions or gears 1145 on the outer surface of the gear members 1131.

Also seen in FIG. 69 are the support means 1133, that may be positioned adjacent the top aspect of the gear member 1131. These support means 1133 may nest against an internal shoulder or similar structure on the undersurface of the top member 1120 and facilitate alignment of the expansion assembly 1130 as well as function as a bearing surface for the support means 1133. FIG. 71 shows the two expansion assemblies 1130 nested within two corresponding holes 1112.

Figure 70:
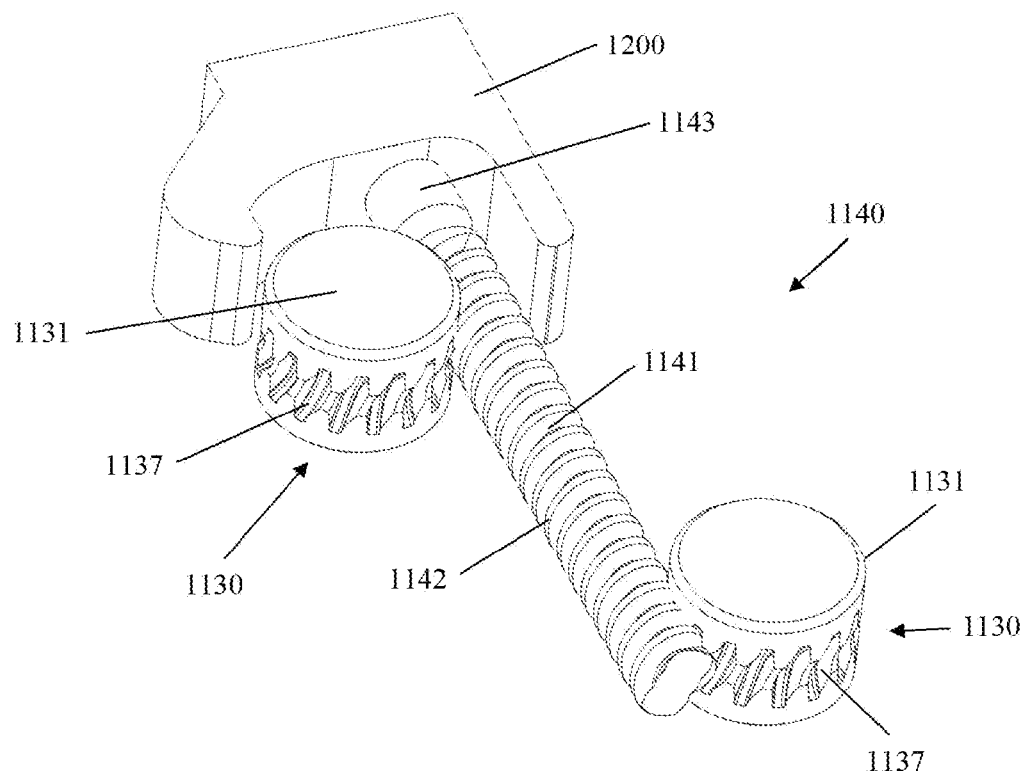
FIG. 70 is a superior perspective view of the dual expansion assemblies with the connecting drive rod of the expandable interbody fusion device of FIG. 68 showing the distal end only of the inserter tool, in accordance with an aspect of the present invention.

FIG. 70 shows the expansion mechanism 1140 that is comprised of at least two expansion assemblies 1130 and a connecting drive rod 1141 that spans the space between the two expansion assemblies 1130. The spacing between the expansion assemblies 1130 typically matches the distance between holes 1112. The expansion mechanism 1140 functions to convert rotation movement of the gear member 1131 into linear or translational movement of the top member 1120 by the extension of a threadingly coupled threaded rod from the internal aspect of the gear member 1131. The connecting drive rod 1141 functions to mirror the rotational movement between the first and second gear member 1131 and ultimately, the travel distance of the dual expansion assemblies 1130 when the expansion mechanism 1140 is actuated by an expansion tool. The connecting drive rod 1141 may be comprised of a cylindrical shaft with an opening at one end 1143 to accommodate the inserter tool

1200. Disposed along the length of the connecting driver rod 1141 may be worm gears 1142 or other similar gearing configurations that will mate with the corresponding gears or depressions 1137 disposed on the outer surface of the gear member 1131.

As seen in FIG. 71, when the implant 1100 is assembled, the connecting drive rod 1141 is positioned in a manner wherein, it extends and makes contact with one outer side of a first gear member 1131 and the opposing outer side of the second gear member 1131. The connecting drive rod 1141 is held in manner that will allow it to be freely rotated and pass between the two gears members 1131.

Although not shown in detail in the figures, the constructed expansion assembly 1130 typically is comprised of various components that include the gear member 1131, a threaded rod with a load head that extends from one end of the gear member 1131 and the support means 1133. The load head will generally be configured to maximize load transfer from the expansion assembly 1130 to the undersurface of the top member 1120. The top surface of the load head will be configured to avoid point contact and high stress loads when it makes contact with the undersurface of the top member 1120. The threaded rod will typically have external threads that may extend along its length. The rod may be hollow to allow for bone graft placement. The external threads are configured to match the internal threads of the hollow gear member 1131.

As seen in FIGS. 69-70, the gear member 1131 is circular in shape and includes a gear face with a continuous circumferential sequence of cogs, vertical or angled depressions or teeth 1137. These cogs or teeth 1137 are configured to allow for mating with the worm gears 1142 on the connecting drive rod 1141. The expansion assembly 1130 functions to convert rotational movement of the gear member 1131 into translational movement of the inserted threaded rod. This is achieved by allowing free rotational motion of the gear member 1131 while restricting the rotation of the threaded rod. By restricting the rotation of the threaded rod, the rod moves in either an upward or downward direction relative to the gear member 1131 depending upon whether the external/internal threads are oriented either in a right-handed or left handed direction. As discussed above, when the threaded rod moves, the load head will contact the undersurface of the top member 1120 to either move it away from the base member 1110 or towards the base member 1110. In other words, the implant 1100 height either increases or decreases depending upon the rotational direction of the connecting drive rod 1141.

As shown in FIG. 69, support means 1133 are used both adjacent to the threaded rod and the gear member 1131. The support means 1133 may be, for example, a snap ring or other similar type of structure that will secure the expansion assembly 1130 within the openings 1112 of the base member 1110 and the top member 1120. The support means 1133 also facilitate retaining the expansion assembly 1130 in a position adjacent to the base member 1110.

As shown in FIG. 69, the end 1143 of the connecting drive rod 1141 may be configured as, for example, a female hex end, although a square or other multi-lobed configuration may be used, to mate with the insertion tool. Once the desired expansion of the implant 1100 has been achieved a locking insert may be connected to the insertion tool be positioned into an expansion tool opening 1150 that is disposed on the side of the implant 1100 to secure the height or spacing (see FIG. 68). After the locking insert is secured in the implant 1100, the tool may be removed.

Although not shown, it is understood that for example purposes, the locking insert may include a shaft and a head. The head will likely be countersunk into the tool opening 1150 of the implant 1100 when fully inserted. The head may also include at least one protrusion to secure the locking insert to the implant 1100. The locking insert may be inserted into tool opening 1150 and at least one protrusion may be snapped into a channel in the tool opening to secure the locking insert in the implant and inhibit any further rotation of the connecting drive rod 1141.

Although not shown, it is contemplated that the implant 1100 and the expansion assemblies 1130 are configured to allow for independent rotation. Therefore, if the two expansion assemblies are not rotated simultaneously then the top member 1120 may be angled relative to the base member 1110 because of the resulting difference in length of the two expansion assemblies 1130. This functionality would be used to address angular deformities that may be encountered intraoperatively.

Figure 72:
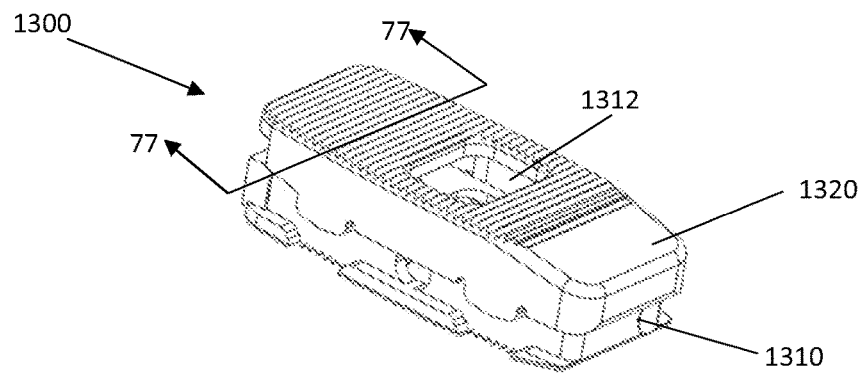
FIG. 72 is a lateral perspective view of another embodiment of a unilateral, vertical expandable interbody fusion device in a fully extended position, in accordance with an aspect of the present invention.
Figure 73:
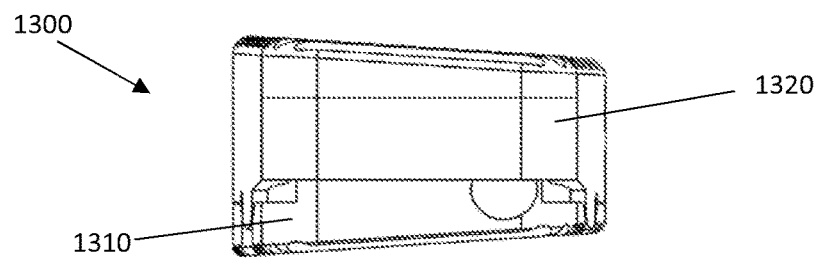
FIG. 73 is an end view of the interbody fusion device of FIG. 72 in a retracted position, in accordance with an aspect of the present invention.
Figure 74:
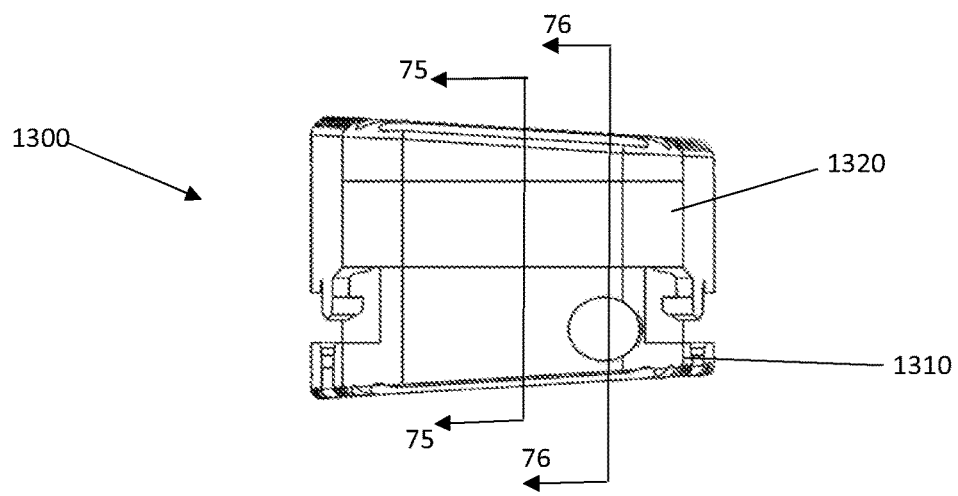
FIG. 74 is an end view of the interbody fusion device of FIG. 72 in a fully extended position, in accordance with an aspect of the present invention.

Referring now to FIGS. 72-77, another example unilateral, vertical expandable interbody fusion device 1300 is shown. The device 1300 includes at least one moveable top or superior member 1320 and a base or bottom member 1310. The top member 1320 may be detachably coupled to the base member 1310. The device 1300 is similar to the devices 600, 700, and 800 described in greater detail above although device 1300 may have an alternative exterior shape. The device 1300, as seen in FIGS. 72-74, has a generally trapezoidal geometry with various configured long sides to facilitate insertion and bone coverage. Although it would be understood by one skilled in the art that other outside shaped configurations may be used. For example purposes, the long sides are slightly arcuate although it is contemplated that other geometrical shapes may also be used in the construct. The device 1300 may have a tapered or angled bullet tip end on both the top member 1320 and base member 1310 for facilitating insertion into the space between the superior and inferior vertebral bodies.

Figure 75:
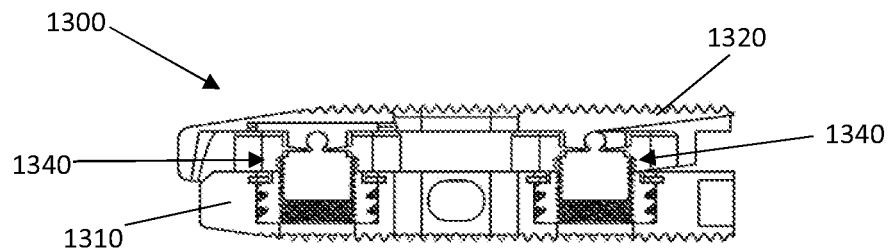
FIG. 75 is a cross-sectional view of the implant shown in FIG. 74 as viewed along section line 75-75, in accordance with an aspect of the present invention.
Figure 76:
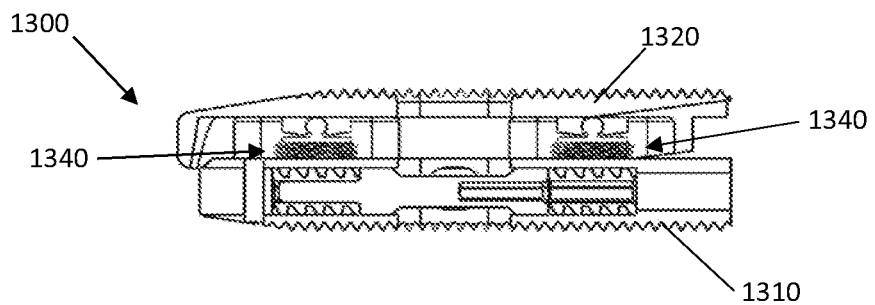
FIG. 76 is a cross-sectional view of the implant shown in FIG. 74 as viewed along section line 76-76, in accordance with an aspect of the present invention.
Figure 77:
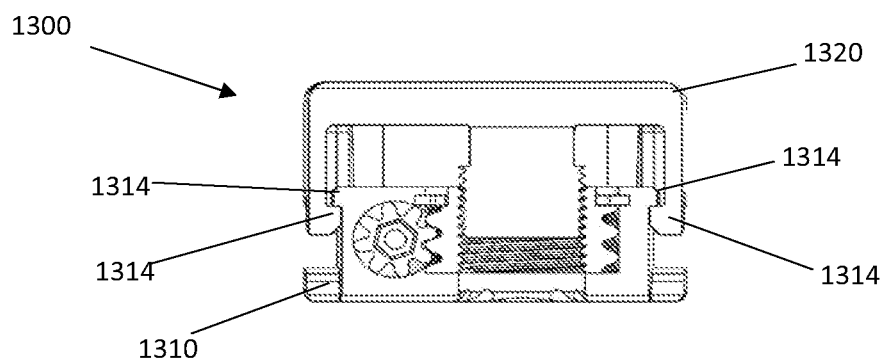
FIG. 77 is a cross-sectional view of the implant shown in FIG. 72 as viewed along section line 77-77, in accordance with an aspect of the present invention.

As seen in FIG. 72, the device 1300 may also include at least one through central opening 1312, of the type described above with reference to opening 612 of implant 600 and for brevity sake will not be described again. The device 1300 may also include an expansion mechanism 1340, as shown in FIGS. 75-76, such as, any one of expansion mechanisms 640, 740, or 840 as described in greater detail above. The top member 1320 and the bottom member 1310 may be of the type described above with reference to devices 600, 700, and 800. The top member 1320 and bottom member 1310 may also include corresponding lips 1314 to engage each other and prevent the top member 1320 from extending beyond the bottom member 1310.

The biocompatible materials used to fabricate the devices 100, 200, 300, 500, 600, 700, 800, 1100, and 1300 could include a myriad of metals, plastics, polymers and composites. Examples of these include PEEK, titanium and stainless steel.

Figure 78:
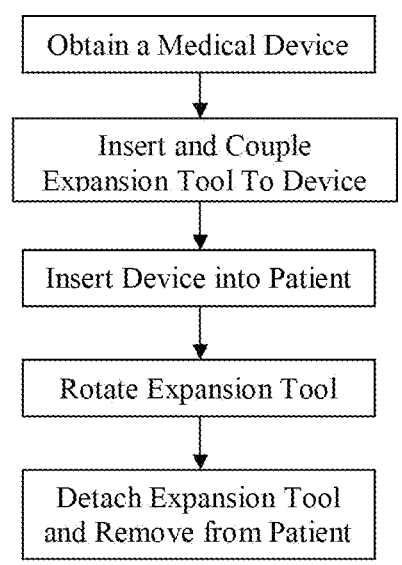
FIG. 78 depicts one embodiment of a surgical method for maintaining a space between two vertebral bodies in a spine, in accordance with an aspect of the present invention.

Referring now to FIG. 78, the example surgical method for using the interbody fusion devices 100, 200, 300, 500, 600, 700, 800, 1100, and 1300 is well known in the art, including the appropriate surgical exposure and dissection techniques. The method includes, obtaining the properly sized and configured device 100, 200, 300, 500, 600, 700, 800, 1100, and 1300 relative to the target vertebral end plates that will be opposing the superior and inferior surfaces 105, 205, 305, 505, 604, and 1105. An expansion/inserter tool, for example, tools 190, 290, 390, 590, or 900, is then inserted into an entry hole, for example, hole 302, 680, 1150 or through the housing 301 to secure any of the devices 100, 200, 300, 500, 600, 700, 800, 1100, and 1300 for insertion into the spine. For example purposes only, described herein is the technique as used in the insertion between two vertebral bodies to maintain the disc space there between. The devices 100, 200, 300, 500, 600, 700, 800, 1100, and 1300 are usually slid from a lateral or posterior-lateral direction into the target disc space.

Following positioning of the device 100, 200, 300, 500, 600, 700, 800, 1100, and 1300 within the disc space, the extension/expansion/insertion tool 190, 290, 390, 590, 900 is rotated causing the superior or top member 120, 220, 320, 520, 620, 1120, and 1320 to move away from the bottom or base member 110, 210, 310, 510, 610, 1110, and 1310 resulting in the overall height dimension of the device 100, 200, 300, 500, 600, 700, 800, 1100, and 1300 to increase or decrease, depending upon the direction of the rotation of the extension/contraction/expansion mechanism 140, 240, 340, 540, 640, 740, 840, 1140, and 1340. The user will stop rotating the extension/expansion tool 190, 290, 390, 590, 900 once optimum support is achieved relative to the inferior and superior vertebral bodies. The method may further include the step of detaching the extension/expansion tool 190, 290, 390, 590, 900 from the bottom or base member 110, 210, 310, 510, 610, 1110, 1310 and removing the instrument from inside the living body.

It should be understood by those skilled in the art that the surgical method described herein may also include alternatively, using modular bone contacting plates or surfaces which have been coupled in some manner to an alternative embodiment of the bottom/base member 110, 210, 310, 510, 610, 1110, 1310 or top/superior member 120, 220, 320, 520, 620, 1120, 1320 to accommodate various clinical deformities or bone growth coatings. For the devices 200, 500, 600, 700, 800, 1100, and 1300 the angular deformities may be addressed by independent expansion or retraction of the two expansion assemblies 230, 530, 629 and 630, 729 and 730, 829 and 830, 1130 to create an angled bone contacting surface 205, 505, 604, 1105 of the superior member 220, 520, 620, 1120, 1320 relative to the base member 210, 510, 610, 1110, 1310.

Although the example embodiments have been depicted and described in detail herein, it will be apparent to those skilled in the relevant art that various modifications, additions and substitutions can be made without departing from its essence and therefore these are to be considered to be within the scope of the following claims.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

What is claimed is:

1. An interbody fusion device, comprising:
a base member including an outer bone contacting surface configured to interface with a bone;
a top member detachably coupled to the base member and cooperatively forming a cavity with the base member, the top member including an outer bone contacting surface configured to interface with a bone;
an expansion mechanism disposed in the cavity, wherein the expansion mechanism includes a first assembly having a first gear ring, a first threaded rod defining a longitudinal axis and threadably coupled to the first gear ring such that the first threaded rod is axially translated along the longitudinal axis when the first gear ring is rotatably driven, a first load head pivotally coupled to a top end of the first threaded rod and engaged with the top member, and a first support member that secures the first gear ring within a portion of the base member, wherein the first support member is a snap ring.

2. The interbody fusion device of claim 1 wherein the first load head includes a channel formed therein and the first threaded rod having a cylindrically shaped pivot member formed on the top end and inserted in the channel of the first load head.

3. The interbody fusion device of claim 2 further comprising a recess formed in an inner surface of the top member and configured to mate with the first load head, where the inner surfaces opposes the bone contacting surface.

4. The interbody fusion device of claim 3 wherein the recess includes a rectangular shape with a longitudinal axis extending along a longitudinal axis of the top member.

5. The interbody fusion device of claim 1 wherein the top member includes an opening in the bone contacting surface through which bone graft material can be inserted into the cavity.

6. The interbody fusion device of claim 1 wherein the base member defines a hole in which the first gear ring is rotatably supported.

7. The interbody fusion device of claim 1 wherein the first ring gear ring includes a plurality of substantially vertical depression arranged circumferentially on an outer surface and configured to mate with teeth of a worm gear disposed on an end of an expansion tool.

8. The interbody fusion device of claim 1 wherein the expansion mechanism further includes a second assembly having a second gear ring, a second threaded rod defining a longitudinal axis and threadably coupled to the second gear ring such that the second threaded rod is axially translated along the longitudinal axis when the second gear ring is rotatably driven, a second load head pivotally coupled to a top end of the second threaded rod and engaged with the top member, and a second support member that secures the first assembly within the cavity.

9. The interbody fusion device of claim 8 further comprising a connector driving rod configured at a proximal end to receive an expansion tool and drivably coupled at a distal end to the second gear ring of the second assembly.

10. The interbody fusion device of claim 8 wherein the first load head and the second load head cooperatively operate to allow the top member to tilt in relation to base member when the first assembly and the second assembly are extended to different lengths.

11. The interbody fusion device of claim 1 wherein the top member defines a channel sized to receive the base member, one or more tabs protruding inwardly into the channel from an inner surface of the top member and one or more notches formed in the outer surface of the base member and sized to receive a corresponding tab.

12. The interbody fusion device of claim 1 wherein the outer bone contacting surface on the base member and the outer bone contacting surface on the top member each include a plurality of teeth-like protrusions formed thereon.

13. An interbody fusion device, comprising:
a base member including an outer bone contacting surface configured to interface with a bone;
a top member detachably coupled to the base member and cooperatively forming a cavity with the base member, the top member defines a channel sized to receive the base member and including an outer bone contacting surface configured to interface with a bone;
one or more tabs protruding inwardly into the channel from an inner surface of the top member;
one or more notches formed in the outer bone contacting surface of the base member and sized to receive a corresponding tab; and
an expansion mechanism disposed in the cavity, wherein the expansion mechanism includes a first assembly having a first gear ring, a first threaded rod defining a longitudinal axis and threadably coupled to the first gear ring such that the first threaded rod is axially translated along the longitudinal axis when the gear ring is rotatably driven, a first load head pivotally coupled to a top end of the first threaded rod and engaged with the top member, and a first support member that secures the first gear ring within a portion of the base member,
wherein the first support member is further defined as a snap ring.

14. The interbody fusion device of claim 13 wherein the first load head includes a channel formed therein and the first threaded rod having a cylindrically shaped pivot member formed on the top end and inserted in the channel of the first load head.

15. The interbody fusion device of claim 14 wherein the top member includes an opening in the bone contacting surface through which bone graft material can be inserted into the cavity.

16. The interbody fusion device of claim 15 wherein the base member defines a hole in which the first gear ring is rotatably supported.

17. The interbody fusion device of claim 16 wherein the first gear ring has a plurality of substantially vertical depressions arranged circumferentially on an outer surface and configured to mate with teeth of a worm gear disposed on an end of an expansion tool.

18. The interbody fusion device of claim 17 wherein the expansion mechanism further includes a second assembly including a second gear ring, a second threaded rod defining a longitudinal axis and threadably coupled to the second gear ring such that the second threaded rod is axially translated along the longitudinal axis when the second gear ring is rotatably driven, a second load head pivotally coupled to a top end of the second threaded rod and engaged with the top member, and a second support member that secures the first assembly within the cavity.

19. The interbody fusion device of claim 18 further comprising a connector driving rod configured at a proximal end to receive an expansion tool and drivably coupled at a distal end to the second gear ring of the second assembly.

20. The interbody fusion device of claim 19 wherein the first load head and the second load head cooperatively operate to allow the top member to tilt in relation to base member when the first assembly and the second assembly are extended to different lengths.

21. The interbody fusion device of claim 13 wherein the outer bone contacting surface on the base member and the outer bone contacting surface on the top member each include a plurality of teeth-like protrusions formed thereon.

* * * * *